United States Patent
Svensen et al.

(10) Patent No.: US 12,023,136 B2
(45) Date of Patent: Jul. 2, 2024

(54) METHOD AND SYSTEM FOR ABNORMALITY DETECTION

(71) Applicant: Saltor Pty Ltd, Forde (AU)

(72) Inventors: Paul Svensen, Forde (AU); Chan Yeoh, Forde (AU); Philip Wilson, Thorneside (AU)

(73) Assignee: Saltor Pty Ltd, Forde (AU)

( * ) Notice: Subject to any disclaimer, the term of this patent is extended or adjusted under 35 U.S.C. 154(b) by 786 days.

(21) Appl. No.: 17/250,077

(22) PCT Filed: May 29, 2018

(86) PCT No.: PCT/AU2018/050520
§ 371 (c)(1),
(2) Date: Nov. 19, 2020

(87) PCT Pub. No.: WO2018/218286
PCT Pub. Date: Dec. 6, 2018

(65) Prior Publication Data
US 2021/0307621 A1 Oct. 7, 2021

(30) Foreign Application Priority Data

May 29, 2017 (AU) ............... 2017902032
Dec. 22, 2017 (AU) ............... 2017279806

(51) Int. Cl.
*G06V 40/00* (2022.01)
*A61B 5/00* (2006.01)
(Continued)

(52) U.S. Cl.
CPC ........ *A61B 5/02055* (2013.01); *A61B 5/0002* (2013.01); *A61B 5/015* (2013.01);
(Continued)

(58) Field of Classification Search
CPC ... A61B 5/02055; A61B 5/0002; A61B 5/015; A61B 5/02416; A61B 5/1118;
(Continued)

(56) References Cited

U.S. PATENT DOCUMENTS 6,309,342 B1   10/2001   Blazey
7,027,621 B1 *  4/2006   Prokoski .............. G06V 40/165
                                                    340/576
(Continued)

FOREIGN PATENT DOCUMENTS

AU      2017279806 A1   12/2018
WO   WO 2008/064431 A1   6/2008
(Continued)

OTHER PUBLICATIONS

International Search Report and Written Opinion of International Searching Authority for Application No. PCT/AU2018/050520, dated Jul. 27, 2018 (10 pages).

*Primary Examiner* — Van D Huynh
(74) *Attorney, Agent, or Firm* — NIXON PEABODY LLP

(57) ABSTRACT

A method, including:
receiving observation data from one or more data-capturing devices, the observation data representing a presence of an individual;
processing the observation data to generate identity data representing the identity of the individual, and to detect at least one physiological characteristic or behavioural characteristic of the individual;
retrieving behavioural profile data of the individual based on the identity data; and
comparing the detected characteristic to at least one expected characteristic represented by the behavioural profile data of the individual to identify an abnormality of the individual.

18 Claims, 22 Drawing Sheets

(51) Int. Cl.
*A61B 5/01* (2006.01)
*A61B 5/0205* (2006.01)
*A61B 5/024* (2006.01)
*A61B 5/11* (2006.01)
*A61B 5/1171* (2016.01)
*G06V 40/16* (2022.01)
*G06V 40/20* (2022.01)

(52) U.S. Cl.
CPC ........ *A61B 5/02416* (2013.01); *A61B 5/1118* (2013.01); *A61B 5/1171* (2016.02); *G06V 40/174* (2022.01); *G06V 40/20* (2022.01); *G06V 40/28* (2022.01); *A61B 2503/00* (2013.01)

(58) Field of Classification Search
CPC ... A61B 5/1171; A61B 2503/00; A61B 5/024; A61B 5/1176; A61B 5/165; A61B 5/18; A61B 5/7267; A61B 2576/00; G06V 40/174; G06V 40/20; G06V 40/28; G06V 10/82; G06V 40/172; G06V 20/52
See application file for complete search history.

(56) References Cited

U.S. PATENT DOCUMENTS

| | | | |
|---|---|---|---|
| 8,725,311 | B1 | 5/2014 | Breed |
| 10,325,510 | B2 * | 6/2019 | Jain .......................... G09B 5/14 |
| 2011/0169603 | A1 | 7/2011 | Fithian |
| 2014/0006326 | A1 * | 1/2014 | Bazanov .................. G06N 5/02 706/46 |
| 2014/0205984 | A1 * | 7/2014 | Chapman ................ G09B 5/14 434/308 |
| 2014/0247343 | A1 * | 9/2014 | Chen ..................... H04N 5/272 348/135 |
| 2015/0113636 | A1 | 4/2015 | Forbes |
| 2015/0366518 | A1 | 12/2015 | Sampson |
| 2016/0225048 | A1 | 8/2016 | Zoldi |
| 2017/0039876 | A1 * | 2/2017 | Alyuz Civitci .......... G09B 7/00 |

FOREIGN PATENT DOCUMENTS

| | | | | |
|---|---|---|---|---|
| WO | WO 2015/114554 | A1 | 8/2015 | |
| WO | WO-2015114554 | A1 * | 8/2015 | ............. G06Q 20/12 |
| WO | WO 2016/126867 | A1 | 8/2016 | |
| WO | WO 2016/135069 | A1 | 9/2016 | |

* cited by examiner

Poor    Good    Excellent

METHOD AND SYSTEM FOR ABNORMALITY DETECTION

CROSS-REFERENCE TO RELATED APPLICATIONS

This application claims priority to and the benefit of International Application No. PCT/AU2018/050520, filed May 29, 2018, which is incorporated by reference in its entirety.

TECHNICAL FIELD

The present disclosure generally relates to a method and system for abnormality detection, e.g., for detecting physical or behavioural abnormalities of a person.

BACKGROUND

Various monitoring devices have been used for monitoring people's behaviour and activities.

For example, surveillance cameras are commonly used for monitoring an indoor or outdoor area to record behaviour occurring in that area. Thermographic cameras such as infrared cameras have been installed in some public places, e.g., airports, ports and terminals, for monitoring body temperatures of passengers, in order to minimise public health risks such as the spread of infectious diseases.

Some of these devices may compare extracted behavioural or physical features of a target person with predetermined ranges representing predetermined "normal" behavioural or physical features.

However, as the behavioural and physiological characteristics may vary among different individuals, and may vary for the same person from time to time, the accuracy and reliability of these devices may be unsatisfactory for certain applications. An exemplary application is the monitoring of students within a learning environment, such as a school.

It is desired to address or ameliorate one or more disadvantages or limitations associated with the prior art, or to at least provide a useful alternative.

SUMMARY

In accordance with the present invention, there is provided an abnormality determination system for determining an abnormality of an individual within a learning environment, including:
  a monitor, including one or more imaging devices, said imaging devices configured to generate imaging signals; and
  at least one abnormality detection server device, including:
    a communications interface to receive data;
    at least one computer processor to execute program instructions; and
    a memory, coupled to the at least one computer processor, storing program instructions for execution by the at least one computer processor to automatically:
    receive imaging signals from the monitor;
    process the imaging signals to generate imaging data;
    process the imaging data to detect the individual, and to generate corresponding identity data representing the identity of the individual; and
    identify an abnormality of the individual based on:
      physical detection data representing the detection of a physical characteristic of the individual from the imaging data, and a corresponding physical profile of the individual; or
      behavioural detection data representing the detection of a behavioural characteristic of the individual from the imaging data, and a corresponding behavioural profile of the individual, and
      context data representing a context of the detected behavioural or physical characteristics within the learning environment.

The present invention also provides an abnormality determination method for determining an abnormality of an individual within a learning environment, including:
  receiving imaging signals from a monitor including one or more imaging devices, said imaging devices configured to generate the imaging signals;
  processing the imaging signals to generate imaging data;
  processing the imaging data to detect the individual, and to generate corresponding identity data representing the identity of the individual; and
  identifying an abnormality of the individual based on:
    physical detection data representing the detection of a physical characteristic of the individual from the imaging data, and a corresponding physical profile of the individual; or
    behavioural detection data representing the detection of a behavioural characteristic of the individual from the imaging data, and a corresponding behavioural profile of the individual, and
    context data representing a context of the detected behavioural or physical characteristics within the learning environment.

The present invention also provides a system, including:
  one or more data-capturing devices configured to generate observation data, the observation data representing a presence of an individual; and
  at least one abnormality detection device, including:
    a communications interface to receive data;
    at least one computer processor to execute program instructions; and
    at least one memory, coupled to the at least one computer processor, storing program instructions for execution by the at least one computer processor to automatically:
    receive observation data from the one or more data capturing devices;
    process the observation data to generate identity data representing the identity of the individual, and to detect at least one physiological characteristic or behavioural characteristic of the individual;
    retrieve, from a profile management device, behavioural profile data of the individual based on the identity data; and
    compare the detected characteristic to at least one expected characteristic represented by the behavioural profile data of the individual to identify an abnormality of the individual.

The present invention also provides a method, including:
  receiving observation data from one or more data-capturing devices, the observation data representing a presence of an individual;
  processing the observation data to generate identity data representing the identity of the individual, and to detect at least one physiological characteristic or behavioural characteristic of the individual;
  retrieving behavioural profile data of the individual based on the identity data; and
  comparing the detected characteristic to at least one expected characteristic represented by the behavioural profile data of the individual to identify an abnormality of the individual.

BRIEF DESCRIPTION OF THE DRAWINGS

Some embodiments of the present invention are hereinafter described, by way of example only, with reference to the accompanying drawings, wherein.

DETAILED DESCRIPTION

Described herein is a system that records biometric data of a person and analyses it in respect of the person's own biometric history. Unlike existing systems which can only measure results against pre-set parameters, the system described herein collects data against a specific individual, builds up their own biometric profile, and uses it as the benchmark for analysis and abnormality detection.

The term "normal" used in this disclosure is intended to refer to a situation that is pre-defined as acceptable, for example, a value is within a pre-determined acceptable range.

An example of a system 100 for abnormality detection will now be described with reference to FIG. 1.

In this example, the system 100 includes at least one monitor 110, abnormality detection server 120 including at least one electronic processing device, and a biometric profile management system server 130.

Figure 1:
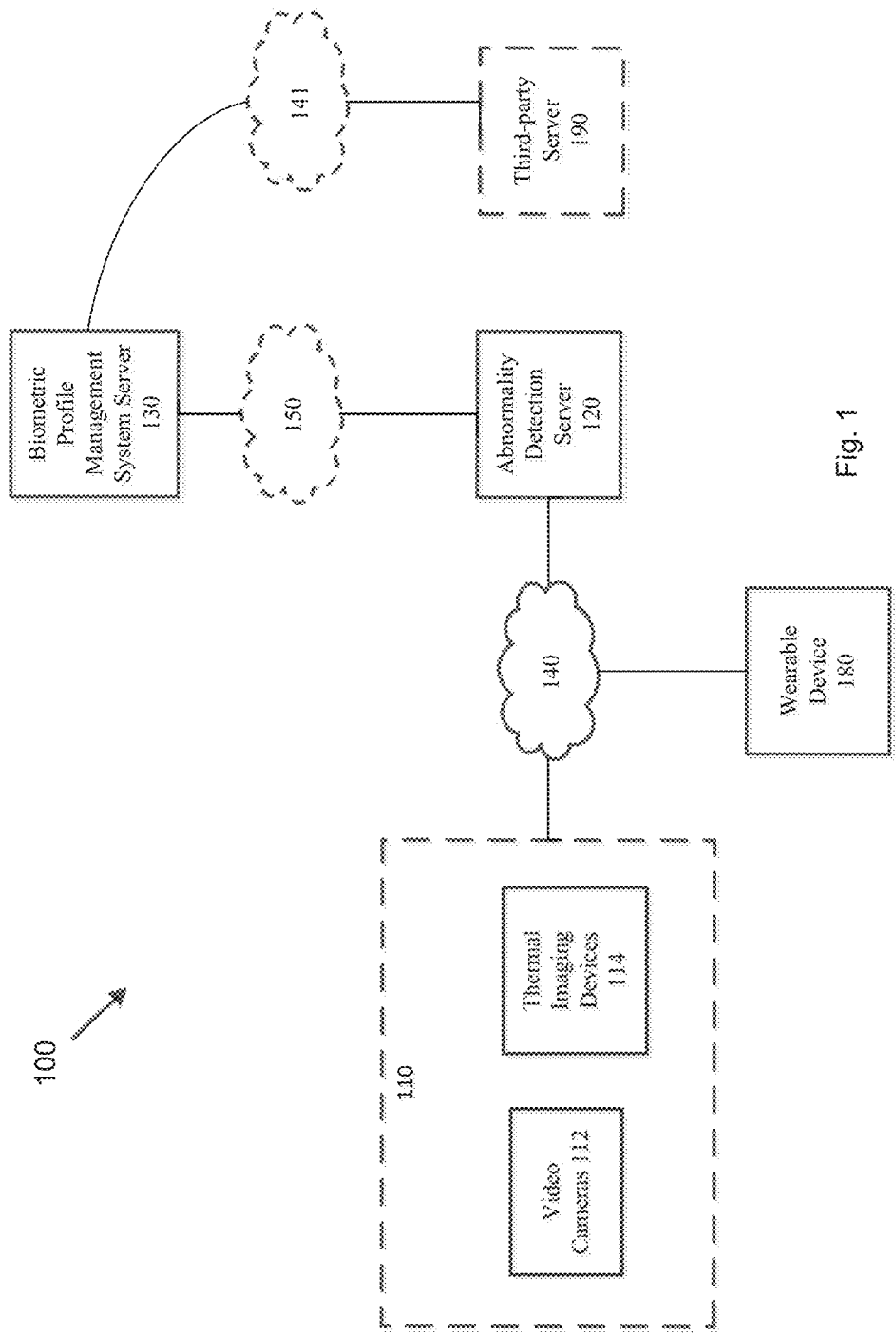
FIG. 1 is a schematic diagram of an example of a system for abnormality detection.

As shown in FIG. 1, the monitor 110 includes one or more video cameras 112 for capturing video signals, and one or more thermal imaging devices 114 for capturing thermal imaging signals including a series of thermal images that are associated with the video signals captured by the video cameras 112.

The video cameras 112 may be, for example, an RGB (red/green/blue) video camera. The thermal imaging devices 114 may be an infrared camera.

The video cameras 112 and the thermal imaging devices 114 are in communication with the abnormality detection server 120 via one or more communication networks 140.

The video signals and the thermal imaging signals acquired by the video cameras 112 and the thermal imaging devices 114 are sent, via the one or more communication networks 140, to the abnormality detection server 120 for processing. Using the received video signals and the thermal imaging signals, the abnormality detection server 120 detects at least one individual (e.g., a person) from the video signal, and detects at least one biometric characteristic of that individual. The abnormality detection server 120 generates biometric detection data representing the detected biometric characteristic.

The biometric characteristic detected by the abnormality detection server 120 may include one or more physiological characteristics, for example any one or more of the following:
a) body temperature;
b) heart/pulse rate;
c) breathing pattern; and
d) pupil dilation.

The biometric characteristic detected by the abnormality detection server 120 may alternatively include one or more behavioural characteristics, for example any one or more of the following:
a) facial expression;
b) body movement; and
c) gesture.

Alternatively, the biometric characteristic detected by the abnormality detection server 120 may include both physiological characteristics and behavioural characteristics.

The biometric profile management system server 130 stores one or a plurality of biometric profiles. Each biometric profile includes information generated based on a specific person's biometric history, e.g., the biometric characteristic of that person detected previously.

The biometric profile management system server 130 is in communication with the abnormality detection server 120, e.g., direct communication, or via one or more communication networks 150. In some embodiments, the abnormality detection server 120 and the biometric profile management system server 130 may be integrated into a single device.

After detecting the biometric characteristic of a person and generating the biometric detection data accordingly, the abnormality detection server 120 retrieves the biometric profile of the person from the biometric profile management system server 130, and identifies an abnormality of the individual based on the biometric detection data and the biometric profile of the person.

In addition to the video cameras 112 and the thermal imaging devices 114, in some embodiments, the monitor 110 may include other data-capturing devices configured to generate data that represents a presence of the individual in an environment in which the system 100 is deployed. For example, the data capturing devices may include biometric sensors that measure other biometric features of a person, for example, fingerprint, voice, face, predefined body motion, electrical capacitance tomography, and/or body weight.

In some embodiments, the monitor 110 further includes a face detector, which detects faces and sends the detection result to the abnormality detection server 120. The face detector may be integrated with the video cameras 112 and/or the thermal imaging devices 114 as a single device. Alternatively, the face detector may be a separated device.

Alternatively, instead of having an independent face detector, the abnormality detection server 120 may include a face detection module for detection of faces using video signals acquired by the video cameras 112. The face detection module may be a hardware module, or a software component within the video cameras 112.

The face detection performed by the face detector or the abnormality detection server 120 may use known facial recognition techniques, wherein:
 (a) it may enable faces to be identified from a distance and the face image to be stored;
 (b) it may identify a person in real time;
 (c) it may detect from one to at least 120 faces per frame (to allow monitoring a group of people simultaneously, for example a whole class of students);
 (d) it may be platform-independent;
 (e) it may automatically detect head, face (including facial expressions), hands (including hand gestures), eyes, nose and mouth;
 (f) it may have the ability to measure photo images in compliance with international standards, such as the International Civil Aviation Organization (ICAO) standard; and
 (g) the recognition may be independent of vantage point, facial expression, glasses and/or facial hair.

In some embodiments, the abnormality detection server 120 may further be in communication with at least one third-party server 190, via one or more communication networks 141. The analysis or detection results generated by the abnormality detection server 120 can be sent to the third-party server 190 for further uses. For example, the third-party server 190 may be a school administration system, or an on-board purchasing system of a cruise ship.

Figure 2:
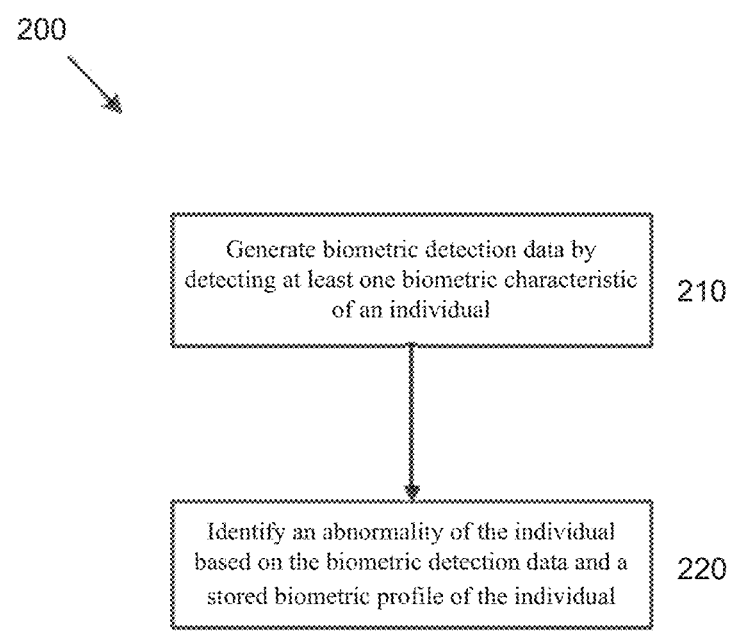
FIG. 2 is a flow chart of an example of a method for abnormality detection.

An example of a method 200 executed by the abnormality detection server 120 for abnormality detection will now be described with reference to FIG. 2.

The method 200 includes:
 a) generating biometric detection data by detecting at least one biometric characteristic of an individual (Step 210); and
 b) identifying an abnormality of the individual based on the biometric detection data and a stored biometric profile of the individual (Step 220).

The generation of the biometric detection data (Step 210) includes:
 a) receiving from the monitor 110:
  (i) video signals; and
  (ii) thermal imaging signals including a series of thermal images that are associated with the video signals;
 b) identifying the individual using the video signals; and
 c) generating the biometric detection data of the individual based on the thermal imaging signals.

The monitor 110, including the video cameras 112 and the thermal imaging devices 114, may be installed in suitable places for monitoring individuals of interest, e.g., people entering a building, location or room, passengers boarding a ship, or students in a classroom.

An exemplary process of identifying the individual and recording his/her thermal images includes:
 (a) in the video signals acquired by the video cameras 112, using skeletal tracking to detect when a new person has entered the field of view and follow them until they leave;
 (b) for each frame of the video signal in which the person is in the field of view, checking their orientation to determine whether it is one of the best frames (e.g., a frame that has an unobstructed view of the person, and the person is facing the camera);
 (c) for each of the best frames, recording the corresponding thermal images acquired by the thermal imaging devices 114 at the same time point;
 (d) once the person is out of the field of view, storing the best frames of the video signal (or relevant portions of the frames).

In this way, thermal images associated with a person are obtained, and can be used for detecting the biometric characteristic of that person.

As described hereinbefore, the biometric characteristics may include one or more physiological characteristic, such as body temperature, heart/pulse rate, breathing pattern, and/or pupil dilation.

In some embodiments, the biometric characteristic includes body temperature and heart rate, which can be detected based on the thermal images of a person.

The abnormality detection server 120 generates biometric detection data based on the detection results. For example, the biometric detection data may include values representing a person's body temperature, heart rate, and number of steps. In some embodiments, the system may receive additional inputs from a wearable device 180 worn by the person being monitored. The wearable device 180 may provide the abnormality detection server 120 with additional information, e.g., values representing the person's heart rate and number of steps, associated with information representing the person's identity.

With reference to FIG. 1, in some embodiments the wearable device 180 is a wrist band that is wearable by individuals within the monitoring environment (e.g. students in a school, or workers in a factory, or residents in a nursing home), and that may provide functionality based on the implementation of the system in that environment (e.g. the ability to replace the seaPass card on a cruise ship). In some embodiments, the wearable device 180 can be loaded with a software application which interfaces with the abnormality detection server 120.

The abnormality detection server 120 then retrieves the biometric profile of the person from the biometric profile management system server 130, and uses the biometric detection data and the biometric profile to determine whether there is an abnormality of the person (Step 220).

The biometric profile includes information representing a person's individuality in biometric characteristics that may be different from others. When detecting an abnormality, a person's biometric detection data is not only referred to a standard, representing what is normal for all target individuals, but also what is normal for that particular person, as indicated by their biometric profile. The system only identifies an abnormality if the detection result is outside an acceptable range for that particular individual.

For example, when measuring a person's heart rate, if the result is compared against a pre-set range representing what is normal for all individuals, an alert may be triggered even when the detected heart rate is acceptable for the particular person. In contrast, according to embodiments provided herein, the person's own biometric profile is also referred to when determining whether there is an abnormality. This may reduce the probability of false alert; thereby increasing the accuracy of abnormal detection.

As described hereinbefore, each biometric profile includes information generated based on a specific person's biometric history, e.g., previously detected biometric characteristic of that person.

In some embodiments, the biometric profile of a person is built and updated over time by the system using the detected biometric characteristic of the person.

The biometric profile may include biometric deviation data, representing a deviation of the biometric characteristic of the individual from the biometric characteristic of a group of individuals.

The biometric reference data may be obtained by:
a) detecting the biometric characteristic of a plurality of individuals; and
b) averaging the detected biometric characteristic of the plurality of individuals.

For example, the group of individuals may include all students in a classroom. When the biometric characteristic to be detected is body temperature, the system may detect the body temperature of each student in the classroom, and calculate an average body temperature, which can subsequently be used as the biometric reference data. This may reduce the effect of ambient temperature variations due to seasonal changes or air-conditioning, and thereby increase the accuracy of the detection of abnormal body temperature.

Using the biometric reference data, the abnormality detection server 120 may generate a relative biometric characteristic value of the person based on: the biometric detection data, the biometric deviation data, and the biometric reference data.

The relative biometric characteristic value may then be prepared with a predetermined threshold. If the relative biometric characteristic value exceeds the predetermined threshold, the abnormality detection server 120 may determine that an abnormality exists.

For example, when the system is detecting abnormal body temperature for students in a class room, the condition for an abnormality can be defined as:

(an individual student's body temperature−average body temperature of the whole class−the individual student's temperature deviation stored in his/her biometric profile)>a predetermined threshold ("Formula A")

In some embodiments, other statical measures of the body temperature of the class may be used in addition to or instead of the average body temperature to indicate the central tendency. The statical measures may include, for example, medians or modes of the body temperatures of the class.

Further, before the calculation using Formula A, the detected body temperatures may be checked by the system so that noise or poor readings may be filtered out. This may be performed, e.g., by comparing the detected body temperature value with a predetermined range of body temperature values.

In some embodiments, the biometric detection data may include a plurality of body temperature values, each representing the temperature of a predetermined body part.

The body temperatures values may include, for example, a head temperature value and a hand temperature value.

The difference between head temperature and other parts of the body may be referred to as the "relative body temperature". The difference between the temperatures of the head and other parts of the body may be different when experiencing a fever compared to strenuous physical activity.

When using the relative body temperature, the condition for an abnormality can be defined as:

(an individual student's relative body temperature− the individual student's relative body temperature stored in his/her biometric profile)>a predetermined threshold ("Formula B")

There may be different pre-selected threshold values when the relative body temperature is calculated based on the temperature of different parts of the body.

This detection based on the relative body temperature (or based on multiple temperatures) may be used in conjunction with or separate from the detection of a single body temperature according to the hereinbefore-described Formula A. This arrangement may reduce or eliminate false positives in the abnormality detection. Alternatively, instead of the detection based on a single body temperature, the detection of relative body temperature may be used by the system as the standard for abnormality detection.

Other biometric characteristics, e.g., heart rate of the person, may also be used to reduce or eliminate false positives, for example, the condition for an abnormality can be defined as:

(an individual student's heart rate−average heart rate of the whole class−the individual student's heart rate deviation stored in his/her biometric profile)>a predetermined threshold ("Formula C")

or (an individual student's heart rate−the individual student's heart rate stored in his/her biometric profile)>a predetermined threshold ("Formula D")

This may be used in conjunction with or separate from the detection based on a single body temperature according to Formula A, and/or the detection based on multiple temperatures according to Formula B.

As described hereinbefore, a person's biometric profile is built and updated over time, i.e., the abnormality detection server 120 updates the biometric profile stored in the biometric profile management system server 130 based on the biometric detection data. In some embodiments, the server 120 sends the biometric data to the biometric profile management system server 130 to update the stored biometric profile based on the biometric detection data.

For example, a student's body temperature deviation from the average body temperature of the class, which is stored in the student's biometric profile, may be updated using an exponentially weighted moving average ("EWMA") defined as:

$$NewAvg = a*X + (1-a)*OldAvg \quad \text{("Formula E")}$$

where a is a weighting parameter between 0 and 1 that represents the degree of weighting decrease, and X is the new value.

The parameter a may change depending on one or more predetermined factors, for example:
(a) level of confidence of facial recognition;
(b) level of confidence in skeletal tracking; or
(c) time information.

For example, the parameter a may be given a greater value when the biometric detection data is obtained with a higher level of confidence of facial recognition or higher level of confidence in skeletal tracking, and may be given a lesser value when a longer time has passed since last update, so that older values which are more likely to be out of date are given lower weights.

Further, different biometric characteristics may have different values of parameter a. On some occasions, different types of measurements may have different degrees of accuracy or different levels of confidence. Accordingly, having a different parameter a for each different biometric characteristic may allow a person's biometric profile to be updated with a higher accuracy.

Further, the abnormality detection server 120 may receive a user input indicating whether the result of the abnormality detection is correct. Accordingly, the abnormality detection server 120 may use this user input to update the biometric profile.

For example, if the abnormality detection server 120 detects a false abnormality, a user may make an input indicating that the result is a false abnormality. The abnormality detection server 120 may, for example, update the biometric detection data stored in the biometric profile with a decreased weight, for instance by giving the parameter a of Formula E a smaller value, e.g., 0.

As another example, if the abnormality detection server 120 detects an abnormality, and a user input indicates that the flagged anomaly has been confirmed by a supervisor, the abnormality detection server 120 may update the biometric detection data stored in the biometric profile with an increased weight, e.g., by giving the parameter a of Formula E a greater value.

Further, the system may be trained by receiving feedback data indicating the health condition of the individuals being monitored. For example, in a training period, each individual being monitored may be requested to provide feedback indicating their health condition, which may be input into the system for updating their biometric profile. The feedback may be automatically obtained by retrieving information from a third-party system or database, e.g., a medical system having health information of the monitored individuals. In some embodiments, the feedbacks may be provided by having the individuals make a gesture (e.g., thumb up) or use other body language to inform the system whether they are healthy and feeling well. The gesture or body language may be captured by the monitor, and detected and recognized by the system.

Figure 3:
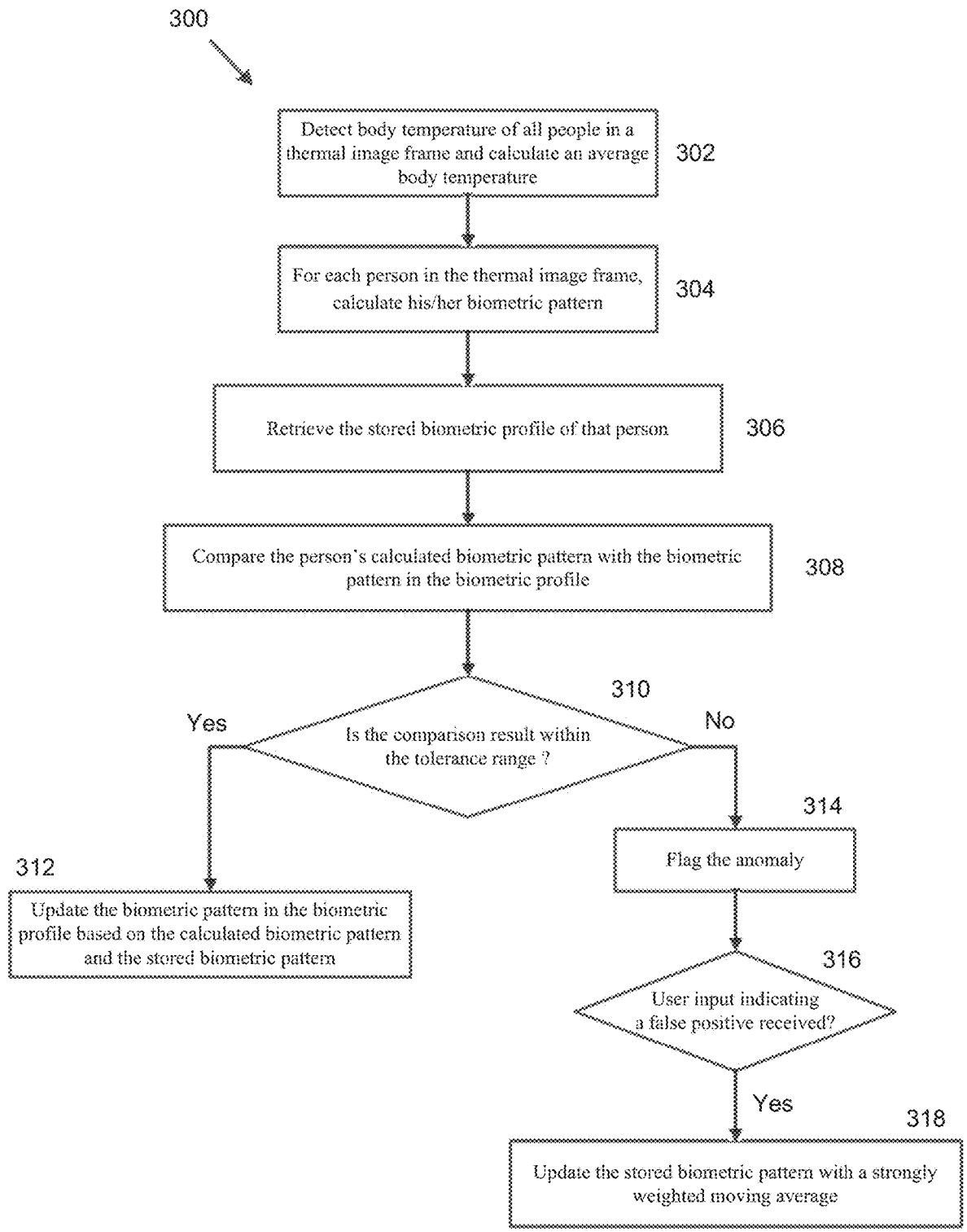
FIG. 3 is a flow chart of an exemplary working process of a server device in the system of FIG. 1.

An exemplary working flow of the abnormality detection server 120 for abnormality detection is shown in FIG. 3. In this example, each biometric profile may include a person's:
(a) deviation of body temperature from the average of the average body temperature of the relevant group;
(b) relative temperature between body parts (e.g., head to hand variation); and
(c) heart rate.

These biometric characteristics may be referred to together as the person's "biometric pattern".

As shown in FIG. 3, the exemplary working flow includes:
(Step 302) detecting body temperature of all people in a thermal image frame and calculating an average body temperature;
(Step 304) for each person in the thermal image frame, calculating his/her biometric pattern;
(Step 306) retrieving the stored biometric profile of that person;
(Step 308) comparing the person's calculated biometric pattern with the biometric pattern in the biometric profile;
(Step 310) checking whether the comparison result is within the tolerance range;
(Step 312) if the comparison result is within the tolerance range, updating the biometric pattern in the biometric profile based on the calculated biometric pattern and the stored biometric pattern;
(Step 314) if the comparison result is outside the tolerance range, flagging the anomaly;
(Step 316) checking whether a user input indicating a false positive has been received; and
(Step 318) if the user input indicating that the flagged anomaly is a false alarm, updating the stored biometric pattern with a decreased weight.

Biometric characteristics of a person may vary over time in a day or in different seasons, and may vary depending on the activity of the person prior to the detection. For example, a person's body temperature may increase after a meal, and may increase after exercise.

Accordingly, in some embodiments, the biometric profile may include a plurality of biometric patterns, each biometric pattern including:
a) information representing a person's individuality in biometric characteristics that may be different from others; and
b) time data indicating a time when the biometric characteristics are detected.

The time data may include, for example, an absolute time such as a clock time.

Alternatively or additionally, the time data may include a relative time, e.g., whether these biometric characteristics are detected: before a predetermined activity, during a predetermined activity, or after a predetermined activity.

Correspondingly, when receiving the video signals and the thermal imaging signals from the monitor 110, the abnormality detection server 120 also obtains detection time information when these signals are acquired by the monitor 110, and generates detection time data accordingly. The detection time data can be included in the biometric detection data.

Based on the detection time data, the abnormality detection server 120 selects one biometric pattern from the plurality of biometric patterns that has a time data corresponding to the detection time data, and uses the selected biometric pattern in identifying the abnormality. The information in the selected biometric pattern can be used in the same manner as the detection based on the biometric profile without time data as describe hereinbefore. Alternatively, in another example, the abnormality detection server 120 may calculate a biometric pattern based on the plurality of biometric patterns that have time data, by giving different biometric patterns different weights, wherein the biometric pattern having a time data corresponding to the detection time data has a or the highest weight.

In addition to time information, other information may be used to generate or modify biometric patterns. For example, season, weather, temperature, the individual's activity prior to detection (which may be obtained, e.g., by utilising a school timetable), may be used for modifying the biometric pattern used for abnormality detection. In some embodiments, a table may be stored and maintained by the system, indicating how different additional factors (e.g., time, season, weather, temperature, and/or previous activity) affects each biometric characteristic, e.g., by indicating how much each biometric characteristic in a biometric pattern should be modified based on each factor.

As an example, the biometric characteristics detected by the system may include: the body temperature, the temperatures of different body parts, and the heart rate; and each biometric pattern in the biometric profile may include:
 (a) deviation of the person's body temperature from the average of the average body temperature of the relevant group;
 (b) relative temperature between body parts (e.g., head to hand variation);
 (c) heart rate; and
 (d) time data (e.g., shortly after physical activity, shortly after a meal, other time).

In some embodiments, each person's biometric profile may include three of such biometric patterns: a normal pattern, an after-meal pattern and an after-sport pattern. In some other embodiments, each person's biometric profile may include a plurality of biometric patterns, each being associated with a combination of multiple additional factors (e.g., time, season, weather, temperature, and/or previous activity), wherein the system compares the conditions at the time of detection to select a biometric pattern that best matches the conditions, or to calculate a biometric pattern based on the similarities between the conditions at the time of detection and the additional factors associated with each biometric pattern, e.g., a biometric pattern having factors more similar to the conditions at the time of detection is given a higher weight.

The number of biometric patterns included in the biometric profile may vary in different applications.

After building a biometric pattern, and using a weighted average to maintain its relevance, any significant deviation from the pattern of any or all characteristics may indicate a change in health or other personal condition.

As described hereinbefore, the biometric profile of an individual may include one or more behavioural characteristics, for example any one or more of the following:
 a) predetermined body movements;
 b) predetermined gestures; and
 c) predetermined facial expressions.

The predetermined body movements may include, for example, one or more of the following:
 a) walking;
 b) running; and
 c) falling down.

The predetermined gestures may include, for example, one or more of the following:
 a) scratching;
 b) hitting/striking;
 c) nodding;
 d) hand raising;
 e) waving;
 f) thumbs up; and
 g) thumbs down.

The predetermined facial expressions may include, for example, one or more of the following:
 a) smiling;
 b) frowning;
 c) eyes closed; and
 d) crying.

The system may detect these behavioural characteristics using movement detection, gesture detection, and/or expression detection techniques.

Subsequently, abnormalities can be identified based on the detected behavioural characteristics of a person and the person's biometric profile.

The system may allow a user to select which behavioural characteristics are to be detected, and may allow the user to define other gestures that are to be detected.

For example, a user may define that striking and hitting are abnormal behaviours in a classroom, and the detection of striking or hitting leads to an alert to be triggered by the system.

Similar to the detection of physiological characteristics, the biometric profile of each person may include information representing a person's individuality in the selected behavioural characters that may be different from others.

For example, some individuals may have higher frequencies of scratching or frowning, which would be recorded in the biometric profile to indicate that high frequencies of these behaviours are normal for these individuals.

The same process of detecting abnormalities in physiological characteristics as described hereinbefore also applies to the detection of abnormalities in behavioural characters.

In some embodiments, the biometric characteristics detected by the system include both physiological characteristics and behavioural characteristics. Accordingly, the system may identify in parallel abnormalities based on physiological characteristics and behavioural characteristics. Alternatively, the detected physiological characteristics and behavioural characteristics may be used in conjunction by the system to detect the abnormality.

For example, the system may detect that a person is doing a strenuous physical activity, such as running. The system may then determine that, if an increase in body temperature is detected after that activity, it should not be taken as an abnormality.

In some embodiments, the stored biometric profile of a person may further include facial features of the person, which can be used for facial recognition.

The abnormality detection server 120 may perform a facial recognition process in detecting the biometric characteristics of a person, so as to find the corresponding biometric profile.

An exemplary facial recognition process may include:
 a) for each stored frame, conducting facial recognition; and
 b) if the facial recognition results in a match to facial features in an existing biometric profile, associating the detected biometric characteristics with that biometric profile.

In some embodiments, the matching result may be checked or reviewed by a human staff. For example, a plurality of identified photos may be displayed in one page on a screen to allow the human staff to skim through to efficiently confirm whether the recognition results are correct, and to identify any incorrect result.

The corresponding biometric profile can then be used for the detection of whether an abnormality exists. The detected biometric characteristics may further be used for updating this biometric profile, e.g., using an exponentially weighted moving average.

If a face is identified in the frame but no matching set of facial features is found, the system may create a new biometric profile based on the detected biometric characteristics, and store the facial features in this biometric profile. In some embodiments, the faces that are not matched may be checked by a human to decide whether a new biometric profile needs to be created.

Alternatively, the facial features may be stored in a separate document, with each set of facial features associated with a unique identifier, whereby each biometric profile is also associated with one of the unique identifiers, to allow a corresponding biometric profile to be retrieved based on the facial recognition result.

This allows the system to monitor biometric characteristics of a plurality of people and distinguish the biometric profile of one person from another.

In some embodiments, the result of the facial recognition may further be used for recording attendance, embarkation/disembarkation control, and/or authority control.

For example, an exemplary attendance recording process may include:
(a) for each person captured in the stored frames, checking their facial image against stored set of facial features associated with expected attendees, by using high level of confidence (or low level of tolerance);
(b) if a person is absent or there are unrecognised stored frames, matching the unrecognised frames with the absentees, by using a lower level of confidence (or high level of tolerance);
(c) if all expected attendees are recognised or all frames have been recognised, the process is complete;
(d) flagging a recognition anomaly if there are unrecognised frames and absentees left; and
(e) if the flagged anomaly has been manually matched by a supervisor, updating the recognition parameters with a strongly weighted moving average.

In this way, by using the same monitor device 110, the abnormality detection server 120, and the biometric profile management system server 130, the system 100 can be used for recording attendance, so that no additional device is required.

Similarly, as described in further detail hereinafter in the "Examples of Implementation", the system can be used for embarkation/disembarkation control, and/or authority control.

When an abnormality is detected, the system may trigger a notification, e.g., an alert or alarm, to notify the relevant staff.

For example, an audio alarm or a visual alert may be triggered if a student in a classroom is detected to have a potential health issue. Alternatively, a notification message may be sent to a relevant teacher or a doctor of the school, to allow further examination of the student. The system may allow the user to configure the notification of abnormality, e.g., by setting different notifications for different levels of severity.

As described hereinbefore, in some embodiments, the abnormality detection server 120 may further be in communication with at least one third-party server 190, via one or more communication networks 141. Communication can occur via a direct link between the third-party server 190 and the abnormality detection server 120, or via an intermediary device (such as the biometric profile management system server 130). The analysis or detection results generated by the abnormality detection server 120 can be sent to the third-party server 190 for further use.

For example, the third-party server 190 may be a school administration system, to which the detection results of potential health issues or abnormal behaviours of students may be sent for school administration purpose.

In some embodiments, the result of abnormal detection may be used for controlling authorization of a predetermined activity. The predetermined activity may include, for example, purchasing alcohol, driving a vehicle, or entering a specified area.

For example, if the system detects that a customer at a bar is intoxicated based on the customer's biometric characteristic detected, the system may generate a notification or alert to notify the bar tender, or to reject a purchase transaction in a payment system that is associated with that customer.

As another example, if a passenger is having a potential health issue, e.g., the passenger having a significantly high body temperature, the system may not authorise the passenger to pass an automatic check-in gate.

Referring back to FIG. 1, in practice, the communications networks 140, 150, and 141 providing communication between the monitor 110, the abnormality detection server 120, the biometric profile management system server 130, and the third-party server 190 may take any appropriate form of wired or wireless networks, including but not limited to mobile networks, private networks, such as an 802.11 network, the Internet, local area networks (LANs), WANs, as well as via direct or point-to-point connections, such as Bluetooth or near field communication (NFC) connections. The communications networks 140, 150 and 141 may include different networks. Alternatively, the communications networks 140, 150 and 141 may be a single network that provides onward connectivity between different components of system 100.

Figure 4:
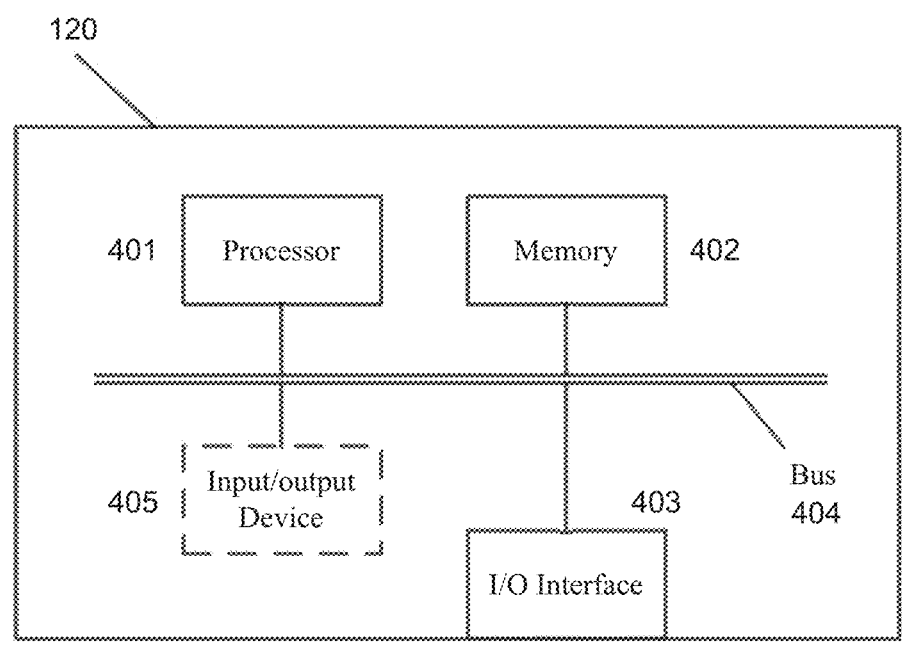
FIG. 4 is a block diagram of an example of the server device.

An exemplary structure of the abnormality detection server 120 is shown in FIG. 4.

In this example, the abnormality detection server 120 includes at least one processor 401, a memory 402, and an external input/output interface 403, interconnected via a bus 404. In some examples, the abnormality detection server 120 may additionally include an input/output device 405, such as a keyboard and/or a display. In this example, the I/O interface 403 can connect the abnormality detection server 120 to peripheral devices and/or networks, including other servers, devices, and local or remote databases. Although a single I/O interface 403 is shown, this is for the purpose of example only, and in practice multiple interfaces using different communication protocols (e.g., Ethernet, serial, USB, or wireless) may be provided.

In use, the processor 401 executes machine-readable instructions stored in the memory 402 to perform at least part of the process described hereinbefore for abnormality detection. The machine-readable instructions may include one or more software components 410 (as described in further detail hereinafter), and may be executed in a suitable execution environment, such as an operating system environment.

Accordingly, it will be appreciated that the abnormality detection server 120 may be formed from any suitable processing system, such as a suitably programmed computer system, PC, web server, or network server. The machine-readable instructions can be embodied in non-transitory computer-readable storage media, e.g., a hard drive.

Figure 5:
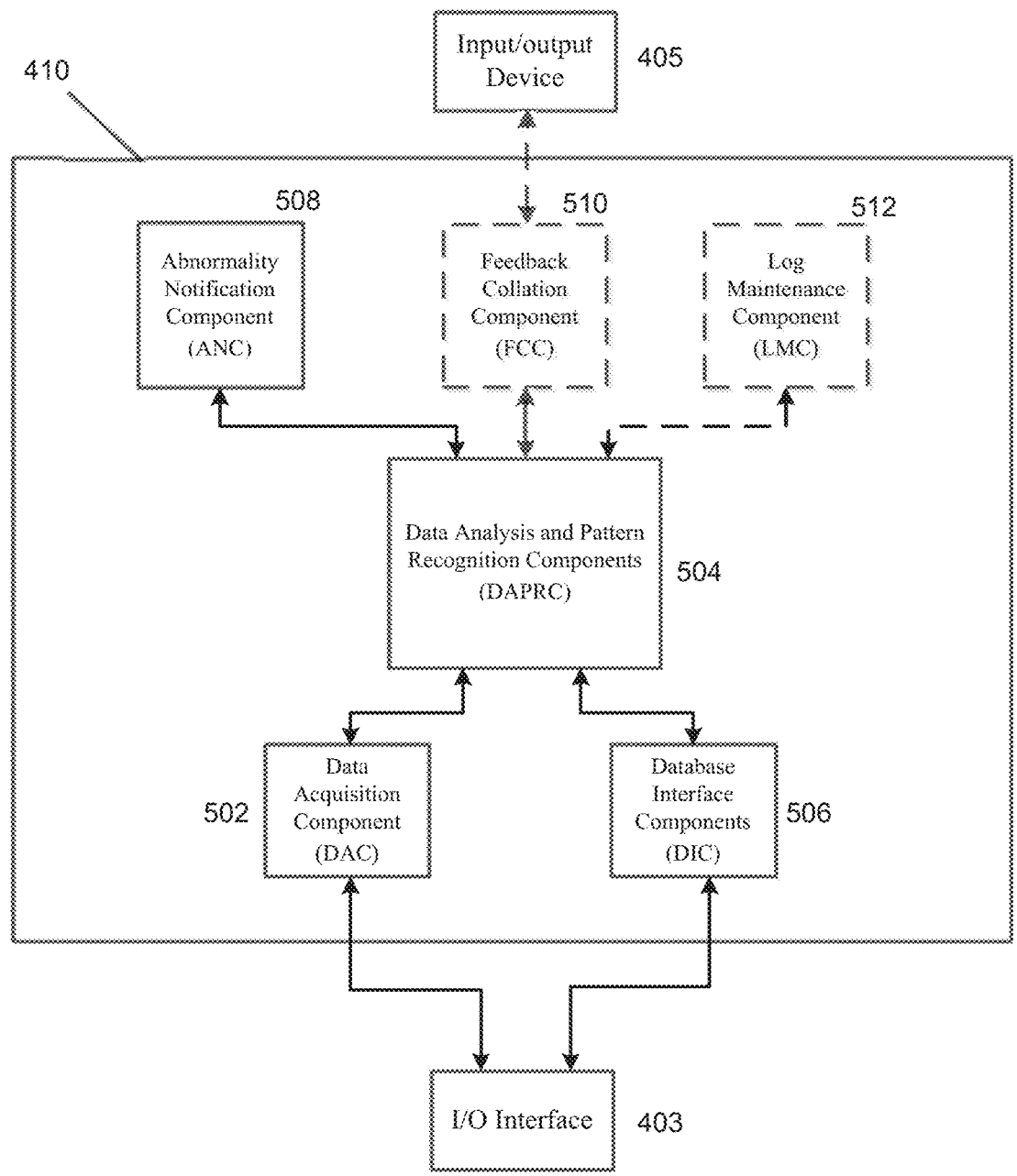
FIG. 5 is a block diagram of exemplary software components of the server device.

An example of the software components 410 included in the machine-readable instructions is shown in FIG. 5.

The software components 410 may include:
a) a data acquisition component (DAC) 502;
b) a data analysis and pattern recognition components (DAPRC) 504;
c) a database interface components (DIC) 506;
d) an abnormality notification component (ANC) 508; and
e) a feedback collation component (FCC) 510.

The DAC 502 controls the collection of data received from the monitor 110 via the I/O interface 403 of the abnormality detection server 120. In addition to the DAC 502, the software components 410 may allow adding new data acquisition components to adapt to additional input signals, for example, adding inputs from additional sensors.

The collected data is sent from the DAC 502 to the DAPRC 504 for analysis, and for recognition of biometric characteristics and patterns, for example:
a) recognise a person in the video data;
b) recognise a known or unknown person in the video data;
c) detect biometric characteristic of a person;
d) detect biometric characteristic of each person in a group; and
e) calculate an average biometric measurement for the group;

Further, the DAPRC 504 accesses the database in the biometric profile management system server 130 through the DIC 506, to build, retrieve and maintain the biometric profiles. Based on the data collected from the DAC 502 and the biometric profile retrieved using the DIC 506, the DAPRC determines whether an abnormality exists.

In addition to the database systems storing the biometric profiles, the DIC 506 may also provide access to other databases, for example, a database for maintaining records of the abnormal detection history, and/or a database for storing the received raw data for a predetermined period of time.

When an abnormality is detected, the DAPRC 504 reports the abnormality to the ANC 508, which may trigger an alert or alarm. The ANC 508 communicates the abnormality or other detection results (which may include predefined "events") reported by DAPRC 504 to additional event subscribers, that will respond to those detection results or events.

The FCC 510 monitors whether a feedback in relation to the detection result has been received. If a user input indicating a false detection is received, the FCC 510 may report this to the DAPRC 504, which may then update the biometric profile stored in the database accordingly, via the DIC 506.

As described herein, the following are performed by the DAPRC 504:
a) receiving data from DAC 502;
b) analysis of received data and detecting biometric characteristics;
c) retrieving biometric profiles via DIC 506;
d) identifying abnormalities;
e) reporting abnormalities to ANC 508; and
f) receiving feedback from ANC 508 and updating biometric profiles via DIC 506 accordingly.

In some embodiments, the abnormality detection is performed in real time, and the result may be sent in real time through a network (e.g., the internet or any other suitable type of network). In some other embodiments, the abnormality detection is performed in a decoupled mode, whereby data are not received in real time. In the decoupled mode, the DAPRC 504 may maintain an internal or external log of timespans and data segments that have been parsed and processed, wherein the data segments may be subtyped by the type of biometric characteristic. This may be used for post-processing of data. The internal or external log may be maintained via a log maintenance component (LMC) 512.

Figure 6:
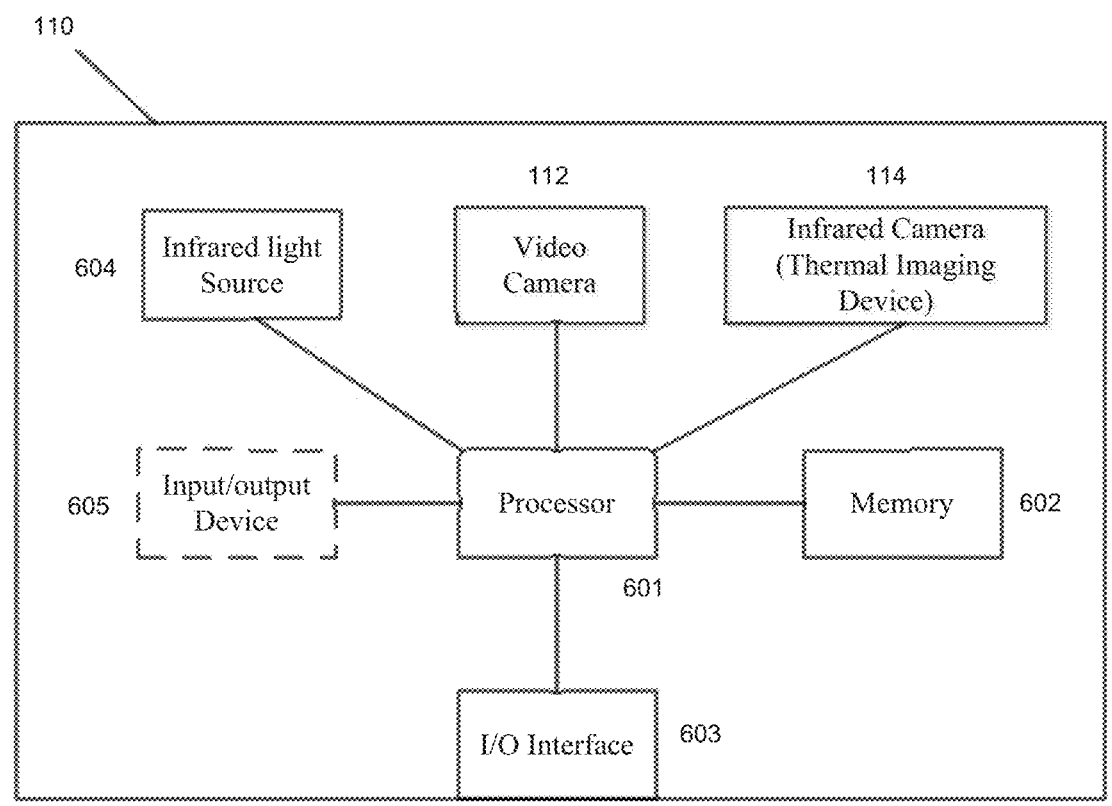
FIG. 6 is a block diagram of a monitor in the system of FIG. 1.

An exemplary structure of the monitor 110 is shown in FIG. 6.

In this example, the monitor 110 includes at least one processor 601, a memory 602 such as a flash memory, an I/O interface 603, an infrared light source 604, the video cameras 112, and the thermal imaging devices 114 in the form of infrared cameras. In some examples, the monitor may additionally include an input/output device 605, such as a display, one or more LED lights, and/or one or more buttons. The input/output device 605 may further include one or more audio input/output devices. In this example, the I/O interface 603 can connect the monitor 110 to peripheral devices and/or networks, such as sending the video signals captured by the video cameras 112 and the thermal imaging signals captured by the infrared camera 114 to the abnormality detection server 120. Although a single I/O interface 603 is shown, this is for the purpose of example only, and in practice multiple interfaces using different communication protocols (e.g., Ethernet, serial, USB, HDMI, wireless) may be provided.

In use, the processor 601 executes machine-readable instructions stored in the memory 602 to control the infrared light source 604 to emit infrared radiation, and control the video cameras 112 and the infrared camera 114 to capture video signals and thermal imaging signals respectively. The processor 601 may perform pre-processing to the captured signals before sending them to external devices through the I/O interface 603. Alternatively, the signals may be sent as raw data by the processor 601 to external devices through the I/O interface 603.

As described hereinbefore, in some embodiments the monitor 110 may include other sensors in addition to the video cameras 112 and the thermal imaging devices 114, e.g., additional biometric sensors that measure other biometric features of a person, such as: fingerprint, voice, face, predefined body motion, electrical capacitance tomography, and/or body weight.

In addition, also described herein is at least one non-transitory computer-readable storage media having computer-executable instructions embodied thereon for abnormality detection, wherein when executed by at least one electronic processing device, the computer-executable instructions cause the electronic processing device to perform:
a) generating biometric detection data using detection signals generated by at least one monitor, the biometric detection data representing at least one biometric characteristic of an individual; and
b) identifying an abnormality of the individual based on the biometric detection data and a stored biometric profile of the individual.

EXAMPLES OF IMPLEMENTATION

Some exemplary applications of the provided method and system will be described as follows.

[Application 1: Schools]

There may be shortcomings with existing methods and systems for monitoring individuals, and detecting abnormalities affecting those individuals, in a learning environment such as a school or university. Existing systems typically compare one or more detected physical or behavioural features of an individual (i.e., a student or other person within the learning environment) with pre-determined reference values (or normal values) for that individual. This process is non-contextual in that it does not account for behaviours or physical traits that are consequences of activities specific to the learning environment.

For example, an elevated body temperature may be an indication that an individual has an illness. However, it may also be detected in a healthy individual who is, or has recently, engaged in vigorous physical activity (e.g., by participating in a gym class). Accurate abnormality detection requires context-specific behavioural and physical modelling in order to distinguish between a deviation in physical and/or behavioural characteristics that are representative of an underlying abnormality of the individual, and deviations that are a consequence of the individual's interaction with, or existence within, the learning environment. This is particularly significant in schools since the individuals being monitored typically engage in behaviours that are not commonly exhibited outside of the learning environment. For example, individuals may exhibit gestures, such as hand raising, and/or particular facial expressions based on their participation in class activities. When deployed within the school environment, conventional abnormality detection methods and systems may interpret these behaviours erroneously.

The embodiments described herein include an abnormality detection system (ADS) and process for detecting abnormalities affecting individuals within a school, or a similar type of learning environment. The abnormalities detected can be physical, such as the presence of an illness or physical condition, or psychological such as, for example, ADHD or anxiety. Embodiments of the abnormality detection system include a monitoring apparatus (also referred to as a "monitor"), with one or more imaging devices configured to generate imaging data representing video and thermal images of a school environment, such as a classroom or play-area, that is frequented by the individuals to be monitored (referred to herein as a "monitoring area"). The imaging data is transferred over a communications network to a server device configured to execute an abnormality detection application (ADA) which receives and processes the imaging data to determine whether there is an abnormality associated with the individual.

Abnormality detection is performed based on biometric information of the individual, including a physical profile and a behavioural profile of the individual, and on contextual information in relation to the individual and/or learning environment at the time of the abnormality assessment. The abnormality detection system (ADS) described herein includes an abnormality detection server device (i.e. a detection server) that is configured to interface with one or more devices, including a biometric profile management system (BPMS) device and individual computing workstations deployed throughout the school (referred to herein as "terminals"). On the detection of an abnormality affecting an individual, the detection server is configured to generate abnormality alert data representing an alert message in respect of the abnormality, and to transmit the alert to the BPMS. When accessed by the appropriate person, such as for example a teacher or welfare officer operating a terminal, the alert message informs the person of the existence of the abnormality.

In the described embodiments, the monitoring apparatus includes three imaging devices, each configured to produce imaging data that is used by the detection server to detect the presence of an individual, identify the individual based on predetermined identity data, and detect particular physical characteristics (such as a thermal signature or heart rate) and behavioural characteristics (such as gestures or facial expressions) that the individual is exhibiting. Individuals that are monitored by the system are referred to hereinafter as "students"; however, the skilled addressee will appreciate that the system may perform abnormality detection for other persons who are not students with respect to the school or learning environment.

The monitoring apparatus is in the form of a camera array which is configured to generate imaging signals representing images of individuals within the monitoring area. Other embodiments of the ADS can include multiple monitoring apparatuses, for example where each is deployed within a different classroom (i.e., monitoring area), in order to extend the abnormality detection capabilities of the system. The cameras of each monitoring apparatus can be physically separated and can operate independently from one another for the purpose of generating the imaging signals. In other embodiments, the cameras are part of an integrated image detection hardware device, such as for example, a Kinect, Flir, Face++, Verilook or Oxehealth device. The image detection hardware device can include individual cameras which are specifically configured for gesture-based human-computer interaction, such as the Intel RealSense 3D cameras or their consumer variants (e.g. the Razer Stargazer and the Creative BlasterX Senz3D).

In the described embodiments, the physical profile of each student includes a temperature profile which represents the nominal temperature characteristics of the student. Thermal signature data is detected for a student, and is compared to their temperature profile data in order to determine the presence of a potential abnormality associated with a raised or lowered temperature. The comparison also involves the use of context data, as obtained from the BPMS or other data source. For example, in the described embodiments, the context data can include an indication of the types of learning activities being undertaken by the individuals at the location, or a state representing the highest degree of physical activity which the individual has engaged in within a particular time period (e.g. within the past hour). This context data can be used in conjunction with biometric information of one or more individuals within the learning environment. For example, an increase in detected temperature values may not necessarily be considered to represent an abnormality if the students are, or have recently been, participating in a particular class where physical exertion is required (such as a gym class).

The physical profile also includes a heart rate profile for the student representing their nominal heart rate levels. The heart rate and temperature profiles can include multiple models corresponding to different contextual states. For example, the heart rate profile can include distinct models for: i) a "resting state" which represents the heart rate of the student when they have not undertaken vigorous physical activity (e.g., when sitting at a desk); and ii) a "high activity" state which represents the heart rate of the student when they are engaged in physical activity (e.g., during gym class).

The behavioural profile of each student contains data representing the tendency of the student to engage in particular behaviours, including exhibiting particular gestures and facial expressions. The detection server is configured to detect gestures and facial expressions that are specific to the school environment (e.g., hand raising), and other gestures and expressions (e.g., frowning, eye movements, etc.). The detected gestures can include "user-defined" gestures that are customised and/or configured specifically for the system (as described below). The detection of a behavioural abnormality involves: i) the detection of a gesture and/or facial expression exhibited by the student; and ii) matching the occurrence of the gesture and/or facial expression to the behavioural profile of the student. The ADS is configured to utilise context data in determining the existence of an abnormality based on detected gestures and/or facial expressions and the behavioural profile. For example, a deviation in the level of class participation of the student (e.g. as measured by the frequency with which the student exhibits particular behaviours, such as hand-raising, within a time period) from the level indicated as normal in their behavioural profile may indicate an abnormality or extraneous issue, unless there is a contextual basis for the lack of participation (such as when the class is currently sitting a test or exam).

In the described embodiments, context data includes environmental attributes representing the properties of the physical environment of the school, and specifically of the location in which the monitoring apparatus is deployed, and activity data representing particular activities which the monitored students are engaged in. Context data can be determined based on learning-environment specific data provided to the abnormality detection server from the BPMS, either automatically or on request. This ensures that the context for interpreting detected physical and behavioural characteristics remains accurate over time.

In other embodiments, context data may be determined by the abnormality detection server during an initial configuration or setup phase, such as in implementations where no significant changes to this information are expected over time. The biometric data and the context data are stored within a data storage device of the ADS, such as a profile database.

In some embodiments, the ADS is configured to dynamically update the biometric data, including the physical and behavioural profile data, of each student based on monitoring and abnormality detection activities performed over a period of time. The system can be configured to perform updates to the profile data selectively based on the result of the biometric data collection process and the comparison of the collected data with the student's existing profile data. That is, updates to the profile data of a student can be made in respect of collected physical and/or behavioural data that is considered to be normal for the student, or that is, at least, within a particular tolerance range relative to those nominal values.

For example, if a student's heart rate was detected as being sufficiently high to constitute a physical abnormality, then the system can be configured to marginalise the physical detection data representing this value during the update process (i.e., the detected heart rate values will not be used to update the student's physical profile in this case).

In some embodiments, the detection server is configured to generate update report data reporting the physical and/or behavioural characteristics of one or more students to the BPMS. The report information can be viewed at a terminal by the appropriate personnel. The detection server can be configured to transmit additional data to the BPMS, including data representing the attendance of individual students, and/or particular critical behaviours or physical characteristics detected for the one or more students (as described herein). The data is transmitted in real-time and is processed by the BPMS, such as, for example, to manage attendance records for particular classes. In some configurations, the attendance data transmitted to the BPMS include an identifier of a student detected to be entering or leaving the monitored location (e.g., a unique student ID value), and an indication of the time when the student enters or leaves the location.

The ADS can be configured to maintain a set of critical physical characteristics and/or behaviours that, when detected with respect to a student, cause the detection server to transmit a critical event message to the BPMS. In some embodiments, the ADS can be configured to provide critical event messages to one or more terminals of the school directly.

The critical characteristics may be physical or behavioural traits that warrant immediate action, such as to prevent a student exhibiting these traits from causing harm to themselves or others. The critical characteristics and behaviours can be defined globally (i.e., those characteristics and behaviours that are considered critical for each student monitored), and individually where the critical characteristics and behaviours may differ for each student.

For example, the presence of particular physical characteristics (e.g., increased heart rate) may trigger a critical event notification (or "alert") for a student with a medical condition, but not for other students. The ADS can also be configured to generate a critical event alert if a student exhibits a particular behavioural characteristic (e.g., striking or hitting another student).

The abnormality detection system and process described hereinafter may advantageously provide a platform for detecting abnormalities affecting school students which:
  a) monitors students within a pre-determined location using a monitoring apparatus consisting of imaging devices configured to generate video and thermal signals, and where the imaging data generated from the signals allows the identification of particular students and the capture of their physical and behavioural characteristics;
  b) maintains physical and behavioural profile information for each student, where the information from each profile is used to determine the existence of an abnormality affecting a student when compared with detected physical and behavioural patterns;
  c) interfaces with existing biometric profile management systems to provide an indication of determined abnormalities in real-time, such that appropriate persons can take action to ensure the safety and well-being of students within the environment; and
  d) determines abnormalities based on a consideration of both the biometric profile of each individual student, and contextual information indicating a particular context of the student's behaviour or physical characteristics within the learning environment.

Figure 7:
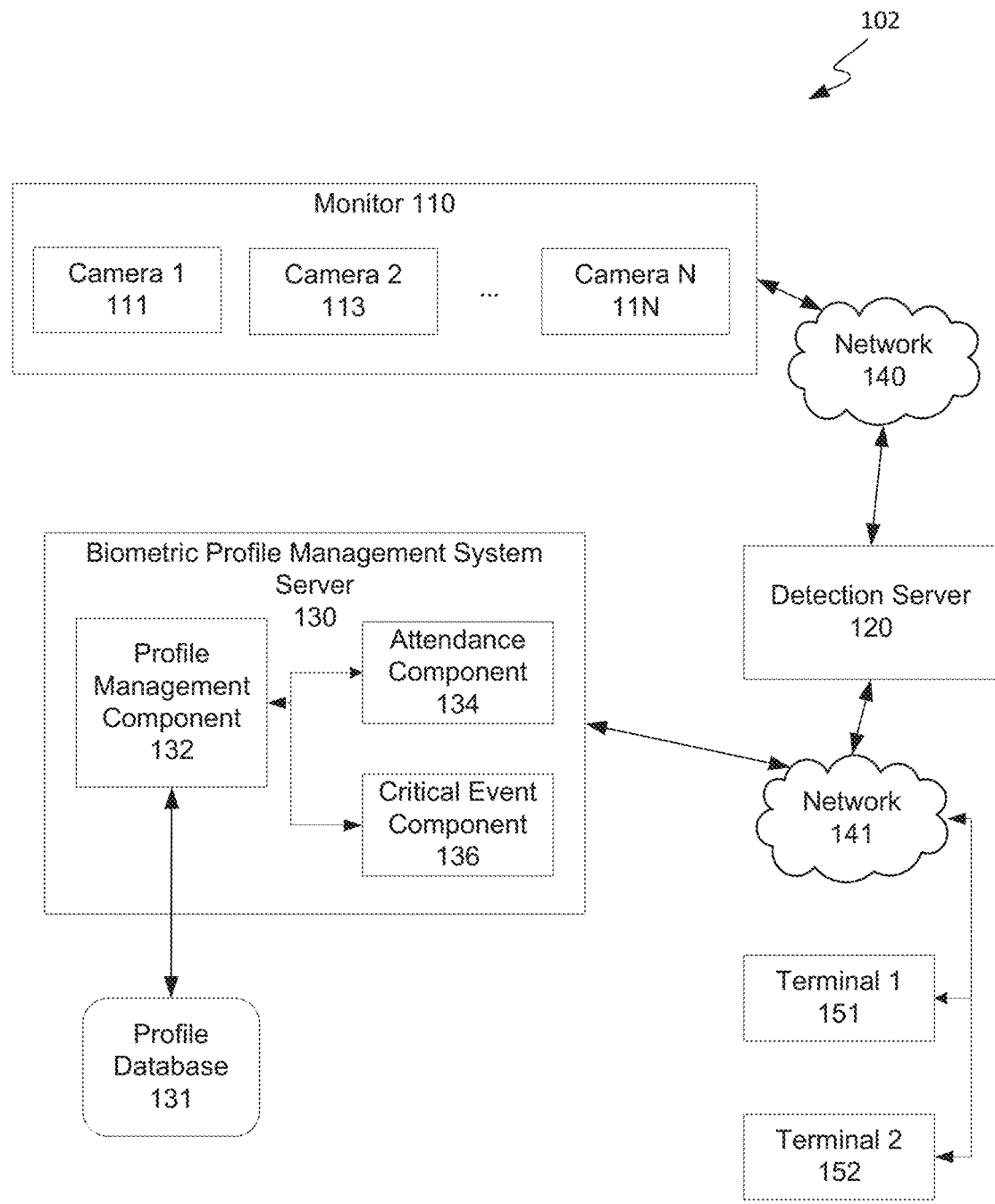
FIG. 7 is a schematic diagram of an example of a system for abnormality detection for use in a learning environment.

FIG. 7 illustrates an exemplary implementation of the ADS 102, including a monitor 110 with camera devices 111, 113 . . . 11N, an abnormality detection server 120 (also referred to as a "detection server 120" to avoid confusion with the ADS 102), a biometric profile management system server 130 and a corresponding profile database 131, and workstation terminals 151 and 152. Cameras 111, 113 . . . 11N include at least one video camera for capturing video signals, and a thermal imaging device for capturing thermal imaging signals, including a series of thermal images that are associated with the video signals, as described hereinbefore. Monitor 110 is deployed such as to generate video signals representing a video feed that covers a predetermined monitoring area within the learning environment (e.g., the inside of a classroom, or a strategic point on the premises).

Monitor 110 can be configured specifically for the learning environment, such as to maximise the field of view of the video cameras over the monitoring area. For example, in some implementations the monitor 110 is placed in a position at the front of a classroom (the monitoring area being the inside of the classroom) allowing the feed that is generated to cover every person in the room, including the teacher. In the described embodiments, monitor 110 is a single standalone device, where cameras 111, 113 . . . 11N include at least three cameras that are configured as follows:
  a) Camera 1—generates video signals at a frame rate and resolution enabling the detection server 120 to detect individuals (e.g., students), and to employ facial recognition technology to identify students entering and leaving the monitoring area; and
  b) Cameras 2 and 3—generate video signals at a frame rate and resolution enabling the detection server 120 to measure the biometric (i.e., physical and behavioural) characteristics of the students in the monitoring area. Specifically, camera 2 operates to obtain vital medical information on each student, including body temperatures (head and torso) and heart rate. Camera 3 captures movements on an ongoing basis, and is configured to generate video signals which allow the detection of behaviours, such as gestures, motion, or holding unknown objects (such as a weapon).

Monitor 110 transmits imaging signals to the detection server 120 via a communications network 140. Detection server 120 is a server device of the kind described hereinbefore, and with the software components 410 illustrated in FIG. 5. A Data Acquisition Component (DAC) receives imaging signals from the monitor 110 and produces corresponding imaging data. The imaging data generated is in the form of a data stream indicating a position (x,y) and a value specific to the signal generated by the particular camera. For example, the data generated for camera 1 can include the co-ordinates of each pixel (x,y) along with a colour value, while for camera 2 the data can include the co-ordinates (x,y) and a corresponding temperature value. A mapping operation is performed by the DAC to resolve the data values generated for each of the cameras 111, 113, . . . 11N in the event that the cameras do not operate at the same resolution. For example, if the video data from camera 1 has a resolution of 1920×1080 pixels and the thermal data from camera 2 has a resolution of 800×600 pixels, the DAC would resolve each set of (x,y) co-ordinates obtained from camera 1 to the corresponding (x,y) values obtained from camera 2.

The DAC also maintains physical and behavioural profile data for each student, and learning-environment specific data, as received from the BPMS server 130 (as described hereinafter). A Data Analysis and Pattern Recognition Component (DAPRC), uses the raw data obtained by the DAC to compare detected data with corresponding profile data, and to determine the existence of an abnormality based on this comparison and on context data representing a context of the detected characteristics.

The DAPRC maintains an internal log of timespans and data segments that have been parsed and processed, subtyped by pattern type.

Examples of the data flow between the DAC and DAPRC are as follows:
  a) Case 1—performing facial recognition to identify an individual within the monitoring area includes:
    (i) Motion detected by monitor 110;
    (ii) DAC receives a video stream signal from camera 111;
    (iii) DAC processes the received video stream signal to produce video data;
    (iv) DAC receives an infrared stream signal from cameras 112;
    (v) DAC processes the infrared stream signal to produce infrared data;
    (vi) DAC generates a data acquisition event and transmits the event to the DAPRC;
    (vii) DAPRC receives the data acquisition event;
    (viii) DAPRC performs facial recognition using the video data;
    (ix) DAPRC recognises a face and raises subject identified event to the biometric profile management system server 130;
    (x) DAPRC receives identification request for time segment;
    (xi) DAPRC performs identification, and if recognition is over 94%, the DAPRC raises a subject-identified event to the biometric profile management system server 130, and additionally to any other systems that are configured to utilise the recognition information such as school administration systems or medical systems;
    (xii) DAPRC performs identification, and if recognition is under 46%, the DAPRC raises a manual-identification-required event to the biometric profile management system server 130; and
    (xiii) DAPRC receives a Face Manually Identified event from another subsystem (such as an I/O device) for a timespan, and updates the identity manager (i.e. for the purpose of registering the identification of the individual based on the manual identification event).
  b) Case 2—processing the thermal signature of an individual:
    (i) Motion detected by monitor 110;
    (ii) DAC receives an infrared stream signal from cameras 112;
    (iii) DAC processes the infrared stream signal to produce infrared data;
    (iv) DAC generates a data acquisition event and transmits the event to the DAPRC;
    (v) DAPRC receives the data acquisition events (Video/IR);
    (vi) DAPRC determines the infrared signature for the group;
    (vii) DAPRC recognises a deviation of the individual from the signature; and
    (viii) DAPRC raises a deviation from normal IR signature event.

Biometric profile management system (BPMS) server 130 is a system that allows school management applications to interact with it through Schools Interoperability Framework (SIF) or web API, such as a school administration system (SAS) application. The BPMS server 130 includes: a profile management component 132 configured to manage data associated with students (such as biometric data) and other individuals associated with the school (e.g., parents and staff); an attendance component 134 configured to manage the attendance of students with respect to the monitoring area; and a critical event component configured to store data relating to critical event detection and notification.

The detection server 120 is configured to communicate with the biometric profile management system server 130 and terminals 151, 152 via communications network 141. The communications networks 140 and 141 can be local or wide area networks (as described hereinbefore), or a combination of a plurality of different local or wide area subnetworks. In some embodiments, detection server 120 communicates with monitor 110, the biometric profile management system server 130 and terminals 151, 152 via a single communications network, or through direct connections between the respective devices, mitigating the need for data transmission over a communications network.

Profile management component 132 is configured to communicate with a profile database 131. The profile database 131 stores data within one or more tables, or similar data structures, which are accessed via a database management system (DBMS) of the profile management component 132. In the described embodiments, the DBMS uses SQL language to query the database 131, which is implemented as an object-oriented database in the described embodiments. Data stored within the profile database 131 includes:

a) Identity data representing the identity of individuals associated with the school, including students, parents and staff, including data representing the name, address, phone number, student/staff ID number, and facial characteristics (i.e., parameters of respective facial feature models for each individual);

b) Biometric data representing the physical and behavioural profiles of students, or other individuals, for whom abnormalities are to be detected by the detection server 120;

c) Logging data representing a record of the arrival and/or departure of students relative to particular monitoring areas, expressed as a "logging event" (e.g., including an indication of the monitoring area, an identifier of the logged student, an indication of whether the logging event is an arrival or departure, and a date-time value representing the time of the event); and d) Learning environment specific data, representing properties of the school that may be interpreted to determine the context of particular detected physical or behavioural characteristics (e.g., timetable data providing an indication of the class or session being undertaken in the monitoring area at particular times throughout the day).

The detection server 120 is configured to: transmit, to the BPMS server 130, an indication of the identity of the individual; transmit, to the BPMS server 130, an indication of an abnormality identified for the individual; and receive, from the BPMS server 130, context data representing a context for detected behavioural or physical characteristics of the individual.

The profile management component 132 is configured to retrieve data from the profile database 131, process the retrieved data in conjunction with reporting data received from the detection server 120 (as described hereinafter), and store updated data in the database 131. In the described embodiments, the profile management component 132 is configured to transmit particular data to the detection server 120, including identity, biometric and learning-environment specific data, during an initial system configuration phase. In some embodiments, student management data is stored within the profile management component 132 of the BPMS server 130. In other embodiments, student management data is not stored locally within the BPMS server 130, and the profile management component 132 operates as a pass-through to allow the ADS 120 to access and update the database 131. The profile management component 132 can also be configured to access the student management data from the database 131, and to transmit the data to the detection server 120 dynamically at predetermined times (such as during the configuration phase), or in response to an update request by the server 120.

Reporting data received by the BPMS server 130 is processed to determine information including:

a) The present occupancy of students within the monitoring area, based on the detection of a student arriving at, or departing from, the area. For example, a group of students may attend an external venue for part of the school day or a student may have to be excused from the classroom to attend a medical appointment. Arrival or departure information within the reporting data is transmitted from the profile management component 132 to the attendance component 134. Attendance component 134 generates corresponding logging event data for storage in the profile database 131, and can transmit the logging data to one or more of the terminals 151, 152 in real-time if required such that the school staff are informed of exactly who is on the premises (e.g., in the case an emergency, etc.);

b) Attendance within the learning environment during predetermined times.

Profile management component 132 can be configured to generate attendance report data based on the logging information received within the reporting data. For example, in the case where the monitored area is a classroom, at the start of each period the teacher can select the appropriate class (from a timetable module in the SAS application, as executed within the profile management component 132). The profile management component 132 will generate the attendance report data in respect of the correct class. The attendance report can be generated in respect of a predetermined period (e.g., one full teaching day), and/or selected classes which were undertaken within the monitoring area; and c) Alerts in respect of any abnormality detected by the detection server 120. An alert is determined when a critical physical characteristic and/or behaviour is detected with respect to a student. Data representing the detection of a critical physical characteristic and/or behaviour for a student (referred to as a "critical event") is transmitted to the critical event component, which is configured to generate corresponding critical event messages of a predetermined form (e.g., an email or Short Message Service text message). The profile management component 132 can be configured to record the occurrence of a critical event by generating corresponding critical event record data, and storing this data in the profile database 131.

Figure 8:
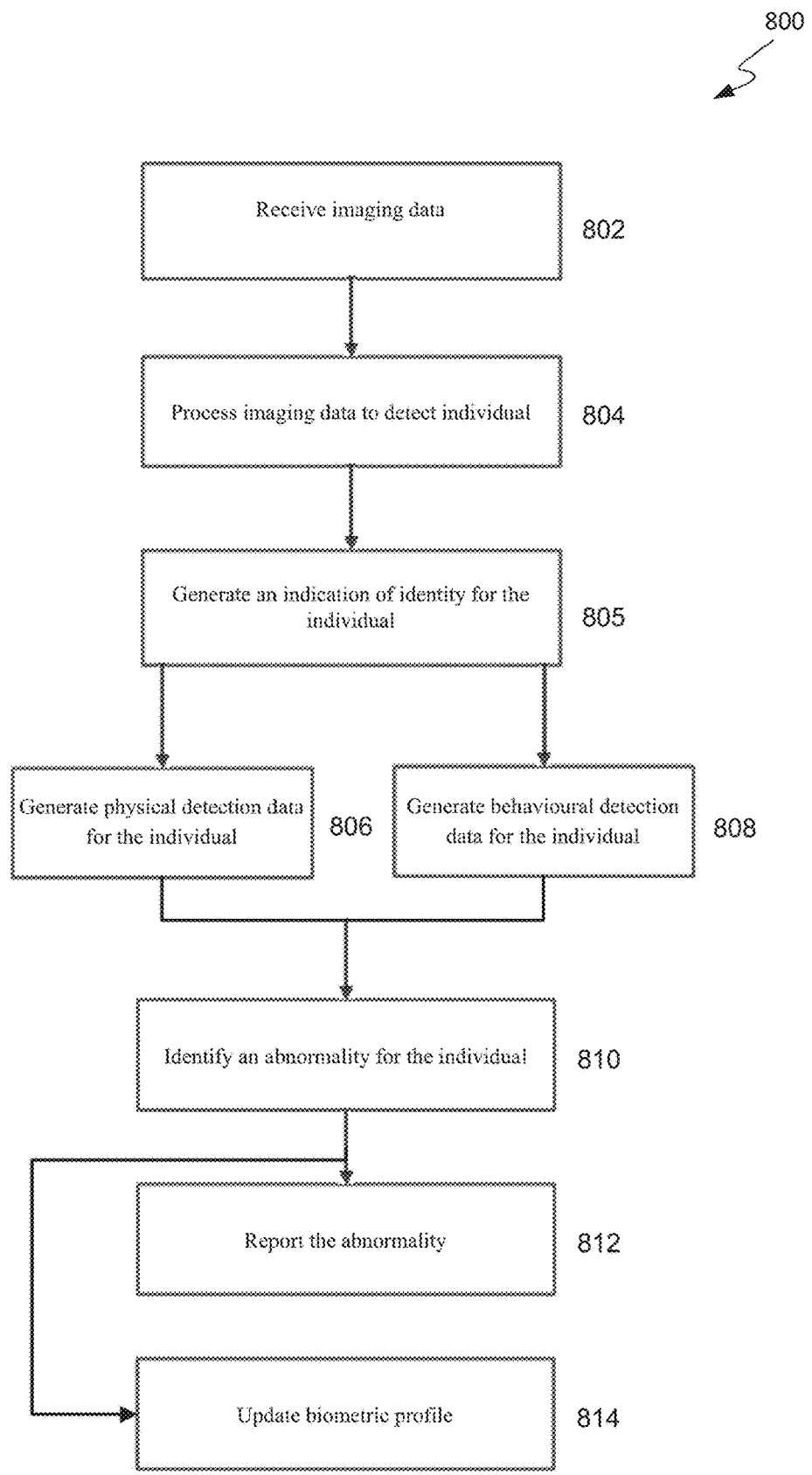
FIG. 8 is a flow chart of an example of a method for abnormality detection of a server device in the system of FIG. 7.

FIG. 8 illustrates a process 800 executed by the detection server 120 for determining an abnormality of an individual within a learning environment, including: receiving imaging signals from the monitor 110; processing the imaging signals to generate imaging data; processing the imaging data to detect the individual, and to generate corresponding identity data representing the identity of the individual; and identifying an abnormality of the individual based on at least one of:

a) physical detection data representing the detection of a physical characteristic of the individual from the imaging data, and a corresponding physical profile of the individual; and b) behavioural detection data representing the detection of a behavioural characteristic of the individual from the imaging data, and a corresponding behavioural profile of the individual, and c) context data representing a context of the detected behavioural or physical characteristics within the learning environment.

The detection server 120 is configured to execute an application which includes: the initialisation of ADS 102 system hardware devices; a monitoring step loop; a recognition step loop (run at a lower priority, or when the system is idle); an attendance step loop (triggered by a timer); a detection process step (triggered by a timer); and a stop/shut down sequence. The monitoring, recognition, attendance and detection steps are performed iteratively in order to conduct the abnormality detection process 800 illustrated in FIG. 8.

At step 802, the DAPRC of the abnormality server 120 receives imaging data generated by the DAC (as described hereinbefore). The imaging data is generated from imaging signals produced by the monitor 110.

At step 804, the imaging data is processed to detect the presence of the individual, and to determine an identity of the individual. Cameras 111, 113, . . . 11N are configured to use skeletal tracking to detect when a person enters the field of view and to follow them until they leave. In the described embodiments, the Microsoft Kinect skeletal detection and tracking algorithm is implemented as the skeletal tracking routine, and is configured to perform the detection of up to six users in the field of view of a camera sensor, and to track skeletal motion for up to two of those users. The imaging data include one or more frames of the respective video signals produced by the cameras 111, 113 . . . 11N. For each of the one or more frames where the individual is in the field of view, the DAPRC is configured to check the individual's orientation to determine the best frames (e.g., unobstructed view, facing the device). For each of the best frames, the DAPRC extracts one or more features representing the detected biometric (i.e., physical or behavioural) characteristics as described hereinafter. Once the individual is out of the field of view, the DAPRC stores the frames (or relevant portions of the frames).

Identification of the individual involves the execution of a facial recognition process on each stored frame. Facial recognition is performed by extracting a set of facial features from the stored frame data, and comparing the extracted features to facial model data representing the unique facial characteristics of each individual enrolled within the BPMS. Facial model data is included within the identity data of each individual, as maintained by the profile database 131 and transmitted to the detection server 120 (as described hereinbefore). The facial recognition process is performed by the detection server 120 using facial model data stored within the detection server 120 (as received from the BPMS server 130 or otherwise), in conjunction with imaging data generated for detected individuals, as described hereinbefore. That is, the ADS can be configured to use both facial model data and thermal imaging data during the recognition process in order to distinguish between two individuals with similar facial characteristics (such as identical twins). If the extracted facial features and imaging data match to those of an individual (to a sufficiently high level of confidence, as described hereinbefore), then the DAPRC generates an indication of the identity of the individual based on the corresponding identity data. In the described embodiments, the identity of the individual is represented by their unique student (or staff) ID number.

At steps 806 and 808, the detection server 120 detects physical and/or behavioural characteristics of the identified student by generating biometric detection data (as described hereinbefore). For example, at step 806 the body temperature and/or heart rate of each student within the monitoring area may be detected. A physical anomaly is determined if the detection data values do not match to the corresponding biometric profile data for the individual (as described hereinbefore).

In the described embodiments, the physical detection data values represent physical characteristics including:
 (a) Heart rate;
 (b) Head temperature; and
 (c) Body temperature.

Figure 9:
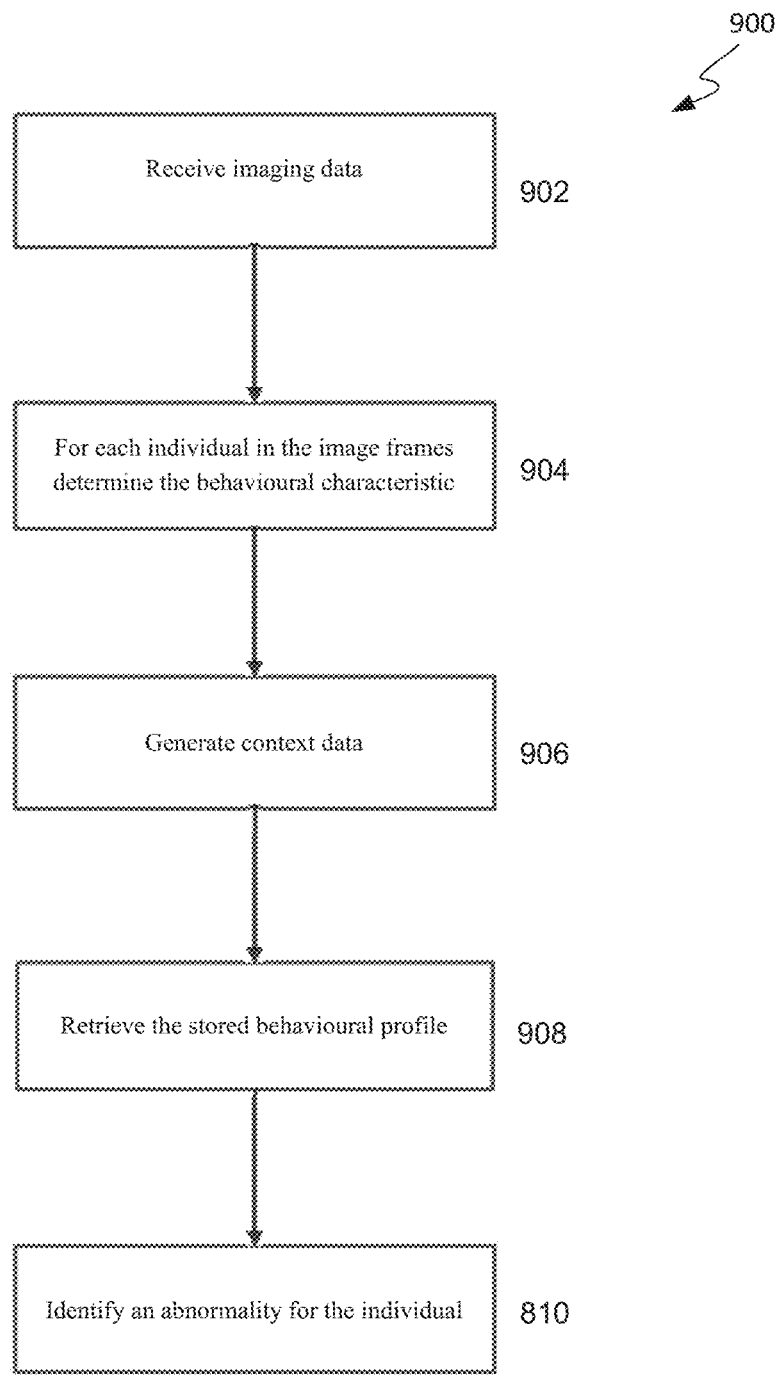
FIG. 9 is a flow chart of an example of a working process of a server device in the system of FIG. 7.

FIG. 3, as described hereinbefore, illustrates an exemplary process 300 by which physical detection data is generated to assess the body temperature of a student. FIG. 9 illustrates an exemplary process 900 for determining: 1) a behavioural characteristic (e.g., a gesture or expression) being exhibited by the individual; and 2) whether the exhibited characteristic constitutes an abnormality. Determining the exhibited behavioural characteristic includes: processing the behavioural detection data to determine that the behavioural characteristic is one of a behaviour type including: a gesture; and a facial expression; comparing the behavioural detection data to one or more behavioural characteristic models of the determined behaviour type; and selecting a particular behavioural characteristic based on a result of the comparison.

In the described embodiments, the behaviour characteristics are specific to the learning environment and include:
 for the gesture behaviour type: (i) Head-scratching (i.e., where the individual scratches their head a set number of times during a defined time period); (ii) Hitting/striking; (iii) Nodding; (iv) Hand-raising; (v) Waving; and (vi) Thumbs up/down; and
 for the facial expression behaviour type: (i) Smiling; (ii) Frowning; and (iii) Crying.

The aforementioned gestures (i)-(vi) are pre-defined by the abnormality detection application executing on the server 120. In some embodiments, the ADS 102 can be configured to detect behavioural characteristics corresponding to other gestures that are customised according to the particular implementation of the system (referred to as "user-defined" gestures). This allows the end users of the ADS 102 to define and store their own gestures, using a gesture modelling software application. For example, where students are prone to using their mobile phones during class, the gestures peculiar to that activity could be defined and stored enabling the system 102 to detect mobile phone use by students within the monitoring area. In another example, a "spinning" gesture can be defined as the spinning of an individual's forefinger in a circular motion. This spinning gesture can be interpreted as an indication that the individual desires the teacher to speak up (i.e. raise his or her voice), and allows the individual to express this desire without needing to raise their hand and wait for the teacher to ask them what they want. The gesture modelling software application creates the user-defined gestures using one or more known gesture creation algorithms, such as the 'User-Defined Gestures for Surface Computing' algorithm by Wobbrock et al., as published in the Proceedings of the 2009 SIGCHI Conference on Human Factors in Computing Systems.

With reference to the process 900 (as shown in FIG. 9) for determining a behavioural characteristic of a student, at step 902 the DAPRC of the abnormality server 120 receives imaging data generated by the DAC (as described hereinbefore). The imaging data is generated from imaging signals produced by the monitor 110.

Figure 10:
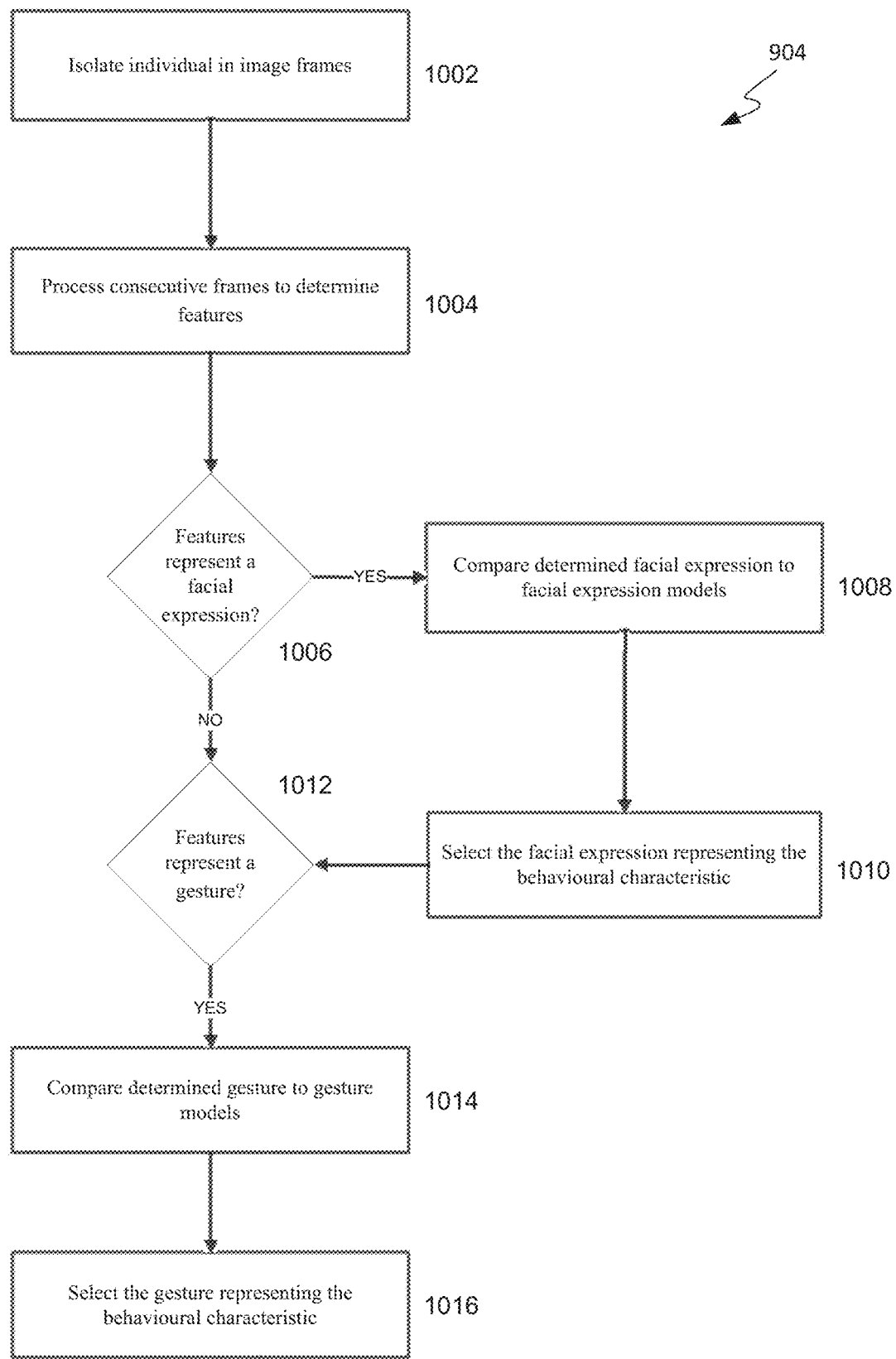
FIG. 10 is a flow chart of an example of a method for detecting a behavioural characteristic of the process of FIG. 9.

At step 904, the DAPRC determines whether a behavioural characteristic is detected over a set of the best frames of the imaging data, where the best frames are determined as described hereinbefore. FIG. 10 illustrates the process of determining the particular characteristic exhibited by the individual. At steps 1002 and 1004, the DAPRC isolates the individual within the frames of the imaging data and processes the frames to extract particular features that are relevant to the determination of behavioural characteristics. For example, in the case where the individual raises their hand, the features can include the trajectories of particular regions of the individual's hand.

The features are extracted from particular regions of the image data which are identified during a pre-processing stage (e.g. the areas corresponding to the hands and face of an individual). The extracted features are analysed to determine the presence of a facial expression or gesture (or both) (i.e., at steps 1006 and 1012 respectively). In the described embodiments, expression and gesture recognition and tracking is performed using an integrated algorithm, such as for example by the method proposed by Pateraki et al. in 'An integrated approach for visual tracking of hands, faces and facial features' as published in Proceedings of the 2011 IEEE Workshop on Measuring and Understanding Human Movements and Emotions. If the individual's behaviour is determined to represent a facial expression, then a comparison is performed between the extracted features and one or more facial expression models of the individual (i.e., at step 1008). The facial expression models are represented by facial characteristic data of the corresponding identity data of the individual. At step 1010, the DAPRC selects the facial expression of the best matching model as a detected behavioural characteristic.

If the behaviour represents a gesture, then a comparison is performed between the features and one or more gesture models (i.e., at step 1014). In some embodiments, the detection server 120 is configured to utilise individual specific gesture models. For example, each student may have their own corresponding set of trained gesture models to represent the behaviour of the student when performing the gesture (as described below). In other embodiments, a set of global gesture models can be defined such that the determination of the gesture (or corresponding "action class" as described herein below) involves a classification process that is independent of the identity of the individual for whom the characteristic is being determined. In this case, each gesture model may be a global model based on a large scale training data set (e.g., a universal background model (UBM) using training data from all students). At step 1016, the DAPRC selects the gesture corresponding to the best matching model as a detected behavioural characteristic.

The detection server 120 is configured to allow the detection of gesture and facial expression behaviours that are simultaneously exhibited by an individual. For example, a student may (i) raise their hand while (ii) simultaneously frowning, and the detection server 120 is configured to detect the two behaviours as distinct actions (i.e., at steps 1010 and 1016, as described hereinbefore).

To determine whether the exhibited behavioural characteristic (as detected in step 904) constitutes an abnormality, at step 906 the DAPRC uses context data representing a context of the detected behavioural characteristic within the learning environment. The DAPRC is configured to process learning environment specific data, as received by the detection server 120 from the BPMS server 130, to determine context data relevant to the identification of an abnormality. For example, the context data can include an indication of the class or session being undertaken in the monitoring area when the behavioural characteristic was detected.

Behavioural Event Generation

According to one implementation of the system, behavioural characteristic detection, as performed during the processes 800 and 900 described above, involves the generation of behavioural event data representing particular actions (such as gestures) and/or emotions (as determined, for example, from facial expressions) of an identified individual. Abnormality server 120 includes a behavioural event generation subsystem which processes data gathered from detection devices (e.g. cameras) of the monitor 110 to generate action and emotion events representing instances of specific gestures and facial expressions exhibited by individuals that are monitored by the system.

The action and emotion event data generated by the behavioural event generation (BEG) subsystem is stored in an action and emotion database, which contains records representing instances of the action and emotion events that are observed by the system. Each event is associated with an individual who is identified by the BEG during the behavioural event determination process. The stored action and emotion events are processed to produce: i) action and event models (such as gesture models, and/or facial expression models, as described above); and ii) behavioural profile data representing the expected (or nominal) behaviour of an individual with respect to the history of actions and emotions that have been recorded for the individual over time. The action and emotion event models are utilised to perform action/emotion recognition (i.e. to determine whether an individual is exhibiting an action or emotion, such as a gesture or facial expression, and to classify that action or emotion), while the behavioural profile is used to perform abnormality recognition (i.e. to determine whether an abnormality exists when an action or emotion is observed for the individual).

The production and/or updating of the models and/or behavioural profiles can be performed during a dedicated training phase of the system. The training process can be performed offline during a training mode, in which the ADS 102 is configured to passively monitor individuals in the learning environment for the purpose of training action, event or behavioural models (i.e. rather than performing abnormality detection). Alternatively, or in addition, the ADS 102 can update the action and event models, and the behavioural profile, of individuals dynamically during operation of the system based on the event data produced by the BEG subsystem.

The BEG subsystem is invoked by the ADS 102 to process the video imaging data received from the monitor 110 (i.e. at step 802) by performing object and detection tracking procedures (as described below) to: identify the individual (i.e. steps 804); and generate one or more action or emotion events representing the observed behaviour of the individual (i.e. during the determination of the behavioural characteristic at step 904).

If an action or emotion (i.e. a "behavioural characteristic") is determined for the identified individual, then an abnormality detector subsystem is invoked to determine the existence of an abnormality (i.e. at step 810) by processing the determined action and/or emotion events in conjunction with the context information and the individual's behavioural profile (as generated and retrieved at steps 906 and 908 respectively).

Figure 11:
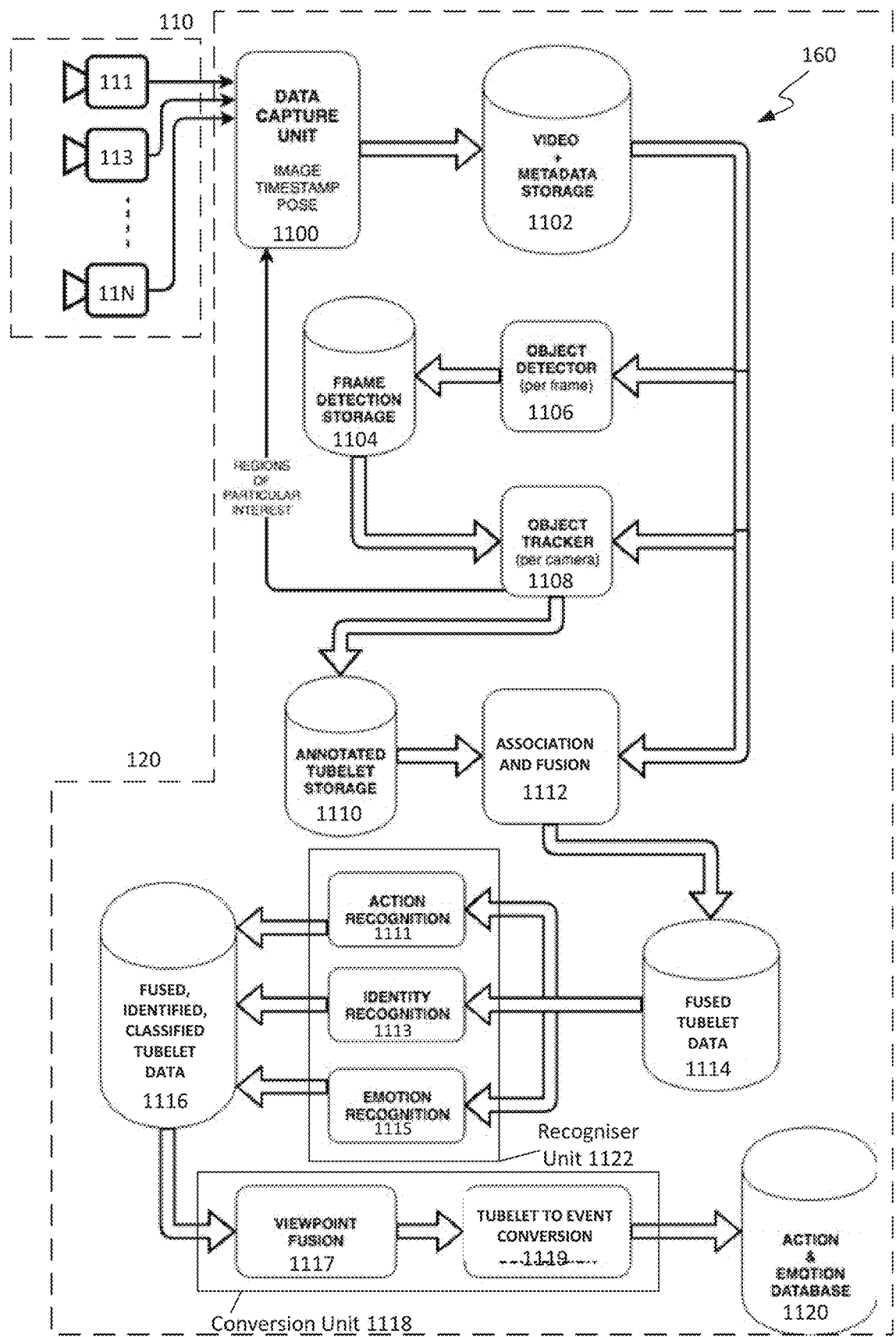
FIG. 11 is a schematic diagram of a behavioural event generation subsystem for the abnormality detection system of FIG. 7.

FIG. 11 illustrates an implementation of a BEG subsystem 160 according to the described embodiments. The BEG subsystem 160 is implemented within the detection server 120, and includes: a data capture unit 1100 which receives input from the monitor 110; a video and metadata storage unit 1102; object detector 1106 and object tracker 1108 units; a frame detection storage unit 1104; an annotated tubelet storage unit 1110; an association and fusion unit 1112 which produces fused tubelet data 1114; a recogniser unit 1122 which produces fused, identified and classified tubelet data 1116; a conversion unit 1118; and an individualised action and emotion database 1120 for storing action and emotion event data generated by the behavioural event generation subsystem 160.

Figure 12:
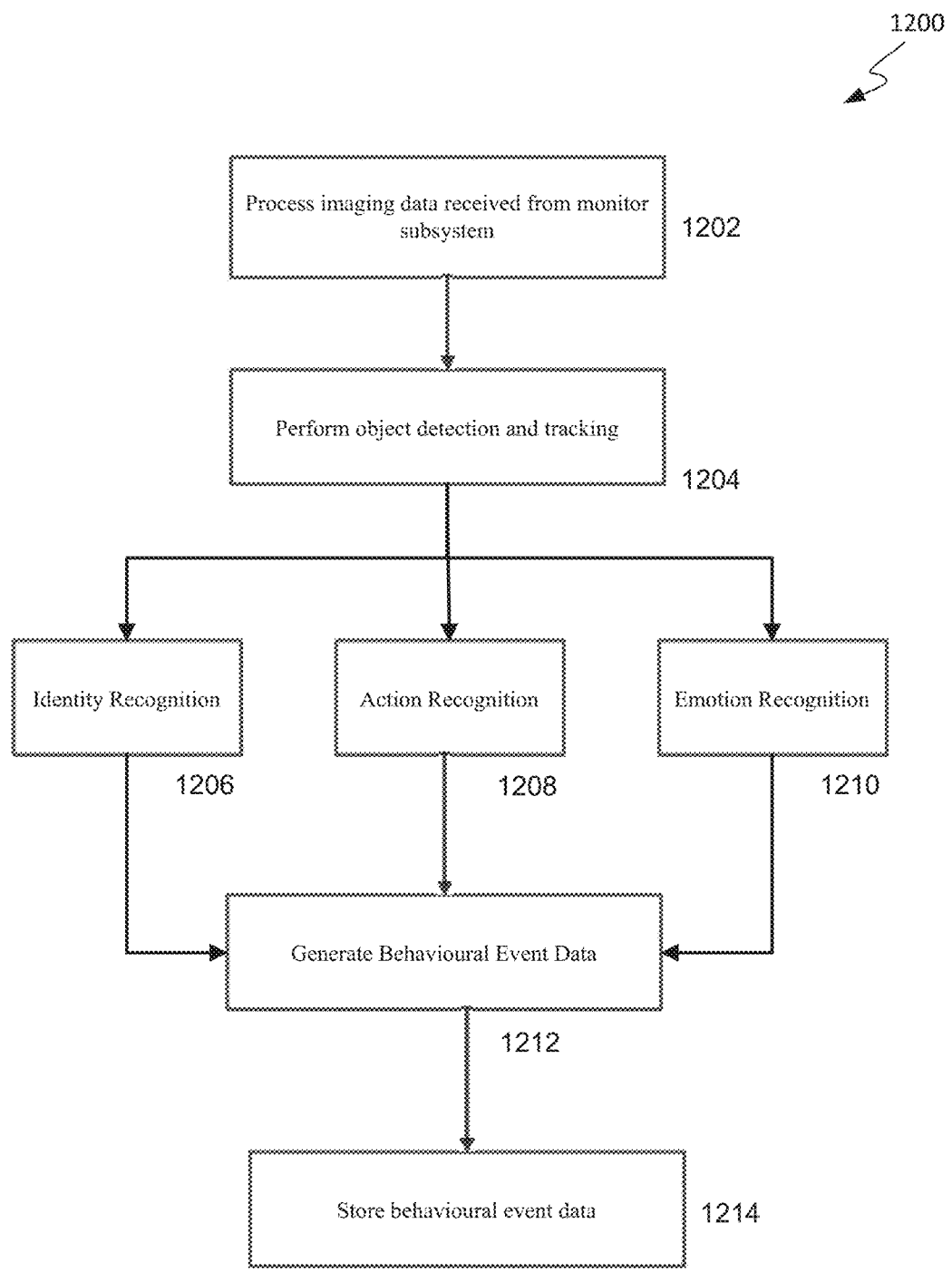
FIG. 12 is a flow chart of an example of a method for generating behavioural events of the behavioural event generation subsystem of FIG. 11.

FIG. 12 shows the process 1200 of operation of the described BEG subsystem 160, which involves: receiving imaging data in the form of a video signal from the monitor 110 (at step 1202); performing object detection and tracking on the received video signal (at step 1204); identifying the individual and the associated actions and/or emotions being performed or expressed by them (at steps 1206, 1208 and 1210); generating behavioural event data in the form of action and/or emotion events (at step 1212); and storing the generated behavioural event data in the action and emotion database 1120 (at step 1214).

As shown in FIG. 11, the data capture unit 1100 interacts with a number of detection devices of the monitor 110 to receive video imaging data. In the described embodiments, the detection devices are cameras 111-11N. The number of cameras N deployed within the monitor 110 can vary based on the size and layout of the monitoring environment, and the pixel resolution of individual cameras. In addition to covering the desired field of view of the monitoring area with regular RGB color space cameras, additional types of optical sensors such as thermal and multispectral cameras may be added to improve the range and orthogonality of data available for analysis and decision making.

In the described embodiments, all cameras share a common trigger signal which is used to enable synchronized image capture. This facilitates the fusion of data received from the cameras 111-11N when these cameras are deployed at separate locations (i.e. during the viewpoint fusion process performed by the conversion unit 1118).

With reference to FIG. 12, at step 1202 the data capture unit 1100 performs frame based processing of the received imaging data. For each captured image frame, the data capture unit 1100 generates video and metadata including: Image data, which is compressed using a format suitable for further analysis; Image meta-data, such as data representing exposure time to aid data normalisation and analysis; Timestamp data, representing the time of the capture of the data; and Camera ID data identifying the camera from which the raw imaging data was received. The generated data is stored in the video and metadata storage database 1102.

In some embodiments, the data capture unit 1100 also generates meta-data for each camera 111-11N, including the location of deployment of the camera, its orientation, its spectral range and one or more field of view parameters. The camera meta-data can be stored in the video and metadata storage database 1102 to facilitate the fusion of objects and events seen from multiple cameras at a later stage in the data processing pipeline.

The data capture unit 1100 processes the image data according to configurable capture and analysis parameters, such as for example the frame rate. This allows the data capture process to be customisable depending on the requirements of the application (e.g. accuracy in detection vs. minimising data storage). For example, in order to register brief actions such as blinking a relatively high frame rate is required (approximately 30 Hz).

To reduce storage and processing requirements for high frame rates, information about particular regions of interest in the video (such as faces) is fed from the object detector 1106 back to the capture unit. The cameras 111-11N can be therefore configured to capture data at a frame rate that is high enough to capture the briefest of events, such as blinking. While the data capture unit 1100 will receive all this data, it can be configured to only retain a fraction of the full set of frames (reducing the full-frame rate to well below 10 Hz), with the exception of particular regions of interest, as identified by the object detector 1106 based on the past few seconds of data. For these regions of interest, all camera frames are retained, and can later be used by the action recognition component to enable detection of brief events. In order to constrain computing requirements, the object detector 1106 and object tracker 1108 operate at the lower, sub 10 Hz frame rate.

In some embodiments, in order to further reduce data storage requirements, the BEG subsystem 160 can be configured to dynamically remove data from the video and metadata storage unit 1102 once the data has been used as required.

At step 1204, the object detector 1106 and object tracker 1108 unit process the video and meta-data stored in storage unit 1102. Note that in some embodiments, the video and meta-data produced by the data capture unit 1100 may be fed directly to the detector 1106 and/or tracker 1108 units, in addition to the storage unit 1102, in order to improve processing efficiency.

The object detector 1106 operates to process a single captured image frame of the video data and returns a set of detections. These detections estimate the location, size and class probability distribution of object instances within the image. Ideally a single detection is associated with every true object instance of interest.

The object detector unit 1106 can be implemented as one of a variety of different pattern classifiers, such as for example Convolutional Neural Networks (CNNs) which are trained on large, manually annotated datasets. A CNN object detector can be implemented as a two stage detector (such as DeNet and Mask RCNN), or as a single stage detector (such as RetinaNet). Two stage object detectors operate by first applying a CNN to estimate the likely regions in the image that may contain an object of interest (of any class). These regions are then classified into classes by a second CNN. A single stage object detector performs both localization and classification in a single step. Single stage detectors may offer advantages including ease of implementation and processing speed in comparison to two-stage detectors, but typically result in reduced localization performance.

Figure 13:
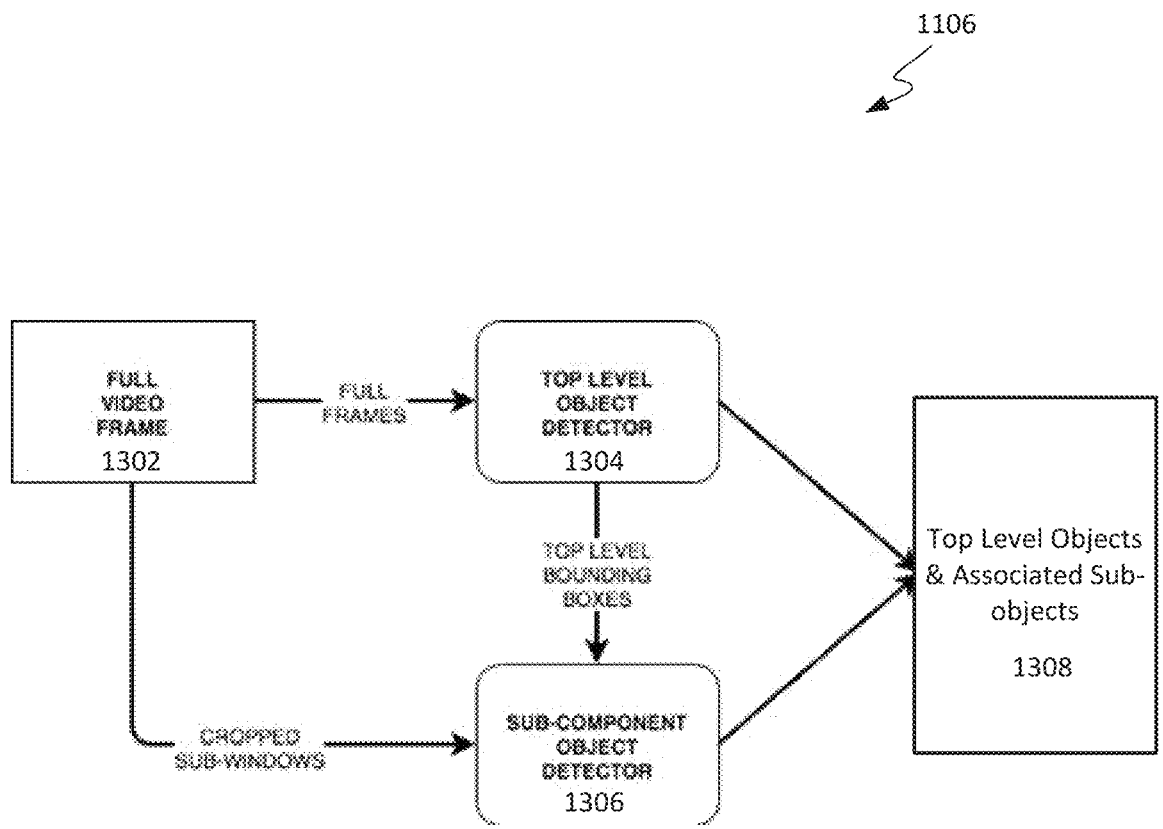
FIG. 13 is a block diagram showing the operation of an object detector unit of the behavioural event generation subsystem of FIG. 11.

In the described embodiments, a two-stage detector is implemented. In order to exploit transfer learning, the initial base CNN is pretrained on the very large image classification dataset ImageNet (which contains 1000 classes, and 1.2M Images). To improve performance, object detector 1106 is implemented as a cascade of 2 individual detectors, as illustrated in FIG. 13. Video frame data from the video and metadata storage unit 1102 is fed into a top level object detector 1304 which operates on a significantly downscaled camera frame (e.g., 1024×1024 pixels) and is responsible for detecting the bounding boxes of large and "high level" objects, e.g., people. These detected large objects are then cropped out from the original, high resolution camera frame and fed into a sub-component object detector 1306 which identifies the location of finer subcomponents (e.g., faces, hands, arms, etc.). The two sets of data produced by respective detectors 1304, 1306 are combined to form top-level object and associated sub-object data 1308 which is stored in the frame detection storage unit 1104 (e.g. within a database in the described embodiments).

The use of cascaded detectors offers performed benefits since the second detector 1306 can be run at full resolution on only cropped image regions instead of the entire frame. The preliminary, per frame, object hierarchy implicitly constructed by the cascade based object detector 1106 will also produce hierarchical clue data that is used in the association and fusion unit 1112 (described below).

The object detector 1106 is trained on a set of images which were manually annotated with bounding boxes indicating the location, size and class of specific objects of interest. When trained as part of an application of the abnormality detection system, these training images should be captured from environments in which the system is expected to perform (e.g. classrooms, etc) and must contain an annotation for every object instance in view. Typically, for acceptable performance 5-10K object instances must be annotated for each class of interest. Depending on the quality of the bounding box annotation sought, the time to annotate a single bounding box is typically in the order of 30 seconds.

Validation experiments have been conducted by researchers on a variety of similar detectors which utilise CNN based detection methods including DeNet, MaskRCNN and RetinaNet. Training was performed with the Microsoft Common Object in Context (MSCOCO) object detection dataset (see http://cocodataset.org) consisting of 120K training images from mostly natural scenes. Within each image all instances of an object belonging to a class of interest (80 classes) has a manually annotated bounding box. A total of ~900K object instances are labelled for training. The classes of interest include typical household objects, e.g., people, animals, cutlery, vegetables, sports items, vehicles, household appliances, etc.

Figure 14:
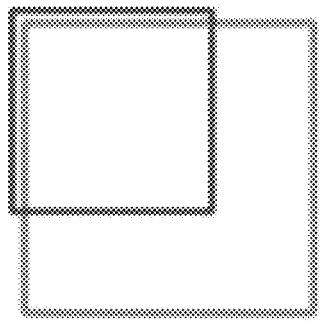
FIG. 14 is a diagram of results for an intersection-over-union (IoU) metric for validating the detection of the object detector of FIG. 13.
Figure 14:
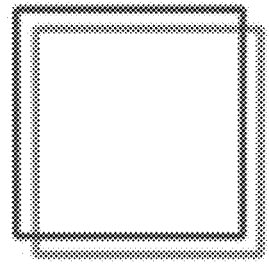
Figure 14:
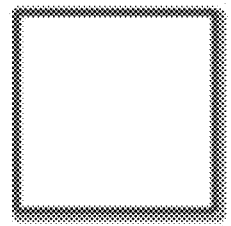

The detection performance was evaluated by calculating the mean average precision at a predefined intersection-over-union (MAP@IoU), and the intersection over union (IoU) values. MAP@ IoU is a metric providing an indication of how likely a detection produced by the detector is a true positive. Given a groundtruth instance, a true positive is defined as a bounding box which is both (a) classified as the correct groundtruth class, and (b) overlaps the groundtruth bounding box with an intersection-over-union (IoU) greater than a user specified value. The IoU value is a normalized metric indicating how well one bounding box overlaps another, an IoU of 1.0 indicates that the boxes overlap perfectly and 0.0 indicates no overlap (see FIG. 14). Note that once a groundtruth instance satisfies the criteria above it can no longer be associated with any other detections, therefore duplicate detections decrease the MAP@IoU metric. The primary metric with MSCOCO is the MAP@IoU [0.5:0.95] which is the MAP@IoU (described above) averaged over a range of IOUs from 0.5 to 0.95.

Results were obtained using a single Nvidia Titan X (Maxwell) GPU. The evaluation rate was also considered since it provides an indication of the cost of deployment and how long it will take the system to respond to an event (i.e. the latency). To aid in comparison all detectors used the same base Convolutional Neural Network (ResNet-101). Moving to larger, more complex neural networks (e.g. ResNext, (Aggregated Residual Transformations for Deep Neural Networks, https://arxiv.org/abs/1611.05431), NAS Net (Learning Transferable Architectures for Scalable Image Recognition, https://arxiv.org/abs/1707.07012)) may provide a moderate improvement to MAP at the cost of evaluation rate.

TABLE 1

MSCOCO results for DeNet, RetinaNet and Mask RCNN object detectors.

| Detector | Evaluation Rate | MAP@IoU [0.5:0.95] | MAP@IoU = 0.5 | MAP@IoU = 0.75 |
|---|---|---|---|---|
| DeNet | 24 Hz | 36.9% | 53.9% | 39.5% |
| DeNet | 11 Hz | 39.5% | 58.0% | 42.6% |
| RetinaNet | 11 Hz | 37.8% | 53.1% | 36.8% |
| DeNet | 5 Hz | 41.8% | 60.9% | 44.9% |
| RetinaNet | 5 Hz | 39.1% | 59.1% | 42.3% |
| Mask RCNN | 5 Hz | 39.8% | 59.6% | 40.3% |

The number of pixels occupied by an object in the image is another important design consideration, objects with fewer associated pixels are significantly more difficult to identify. For instance the MAP@IoU[0.5:0.95] for the 5 Hz DeNet Detector is 57.5% for large objects (area>9216 pixels), 45.0% for medium objects (1024 pixels<area<9216 pixels) and only 21.5% for small objects (area<1024 pixels) where area is the number of pixels the object occupies in the input image.

Good performance at high IoU's is desirable because it can significantly impact the performance of the object tracker unit 1008 detailed below. Utilizing fewer, more easily distinguished classes can significantly improve the detector performance, e.g., with Pascal VOC dataset (20 classes, 16.5K training images) the MAP@IoU=0.5 for DeNet is 77.1% @33 Hz. Based on these results the DeNet CNN provides improved performance when used within the cascade detector 1106 compared to RetinaNet and MaskRCNN.

With reference to FIG. 11, the object tracker unit 1108 performs multiple object tracking (MOT) on the detected object data of the frame detection storage unit 1104 in order to track the locations of multiple objects through time. Object tracking is performed in terms of "tubelets", each of which describes a sequence of bounding boxes through time (i.e. appearing in a sequence of consecutive video frames). Ideally, a single tubelet is associated with each object of interest.

In the described embodiments, MOT is achieved via a Detection Based Tracking (DBT) method. There are two major components to DBT, an affinity model and a data association method. A simple linear motion model is implemented for the affinity model in which it is assumed that objects travel in straight lines, with either a constant velocity or constant acceleration. This allows the estimation of the location of an object in a given frame based on its previous position and motion within prior frames. In this case the affinity is simply the distance from the predicted position to the detection hypothesis position. The object tracker 1108 is configurable to utilise either deterministic optimization or energy minimization for the data association method. In other embodiments, data association may be performed using advanced probabilistic methods.

Training of the object tracker 1108 can be performed with a relatively small set of videos (e.g. 10 videos, 2 min each) with per frame bounding box annotations and instance IDs for each object being tracked (as determined by the object detector 1106, as described above) to form a groundtruth. The groundtruth is used when manually optimizing the tracker parameters for best performance. Assuming the settings above this requires ~36K annotated frames, however the speed of the annotation process can be significantly increased by configuring the object detector 1106 to label the frames then performing manual verification to correct mistakes and associate instance IDs.

For the purpose of verifying the performance of the object tracker 1108 described herein above, training and validation detection experiments were conducted with the MOT challenge dataset (see https://motchallenge.net), which consists of people walking in outdoor environments. This dataset is particularly difficult because target individuals are often occluded by other people. The primary metric for the benchmark is the Multiple Object Tracking Accuracy (MOTA) value which combines the three major error sources: i) False positives, which are tubelet detections which do not overlap any groundtruth detections; ii) Missed targets, which are groundtruth detections with no associated tubelet detections; and iii) Identity switches, where a tubelet switches from tracking one object instance to another. Note that the metric of interest is very dependent on the particular application of the tracker.

Validation results indicated that tracking performance is highly dependent on the quality of the detections used (i.e. the output of the object detector 1106), including how well the object is localized in the image and the class distribution accuracy. The results also showed that by observing an object over many timesteps, the raw performance of the tracker 1108 can be improved since it can infer where an object should be located in a frame given where it was located in other frames, and, via similar means, provide a better estimate of its class distribution (this is supported by findings in Seq-NMS for Video Object Detection, see https://arxiv.org/abs/16020.08465).

With reference to FIG. 11, tubelet data output by the object tracker unit 1108 is annotated and stored in the annotated tubelet storage unit 1110 (which is a database in the described embodiments). The object tracking unit 1108 is configured to generate tubelets over relatively short time sequences (e.g., a few minutes), in order to improve system performance. The association and fusion unit 1112 processes the annotated tubelet data representing the short sequences and fuses these into longer sequences.

The association and fusion unit 1112 uses a similar method to the object tracking unit 1108, which includes an affinity model and data association methods, to fuse tubelets which are associated with the same instance. The main difference is that, instead of operating on detection hypotheses generated by the object detector 1106, the association and fusion unit 1112 uses tubelet hypotheses.

A detection hypothesis is a single bounding box and classification from a single frame generated by the object detector 1106. A tubelet hypothesis is a sequence of multiple detection hypotheses determined to be of the same object instance spread over multiple frames. In the described embodiments, the tubelet hypotheses are limited in length, e.g., 10 seconds in order to improve system performance. The association and fusion unit 1112 observes multiple "tubelet hypotheses" and attempts to link those which are associated with the same instance to create new tubelets that are potentially much longer than 10 seconds. It also creates a hierarchy where all the tubelets for a single person are grouped together, e.g. it might associate the hands, face and body of a single person together.

Figure 15:
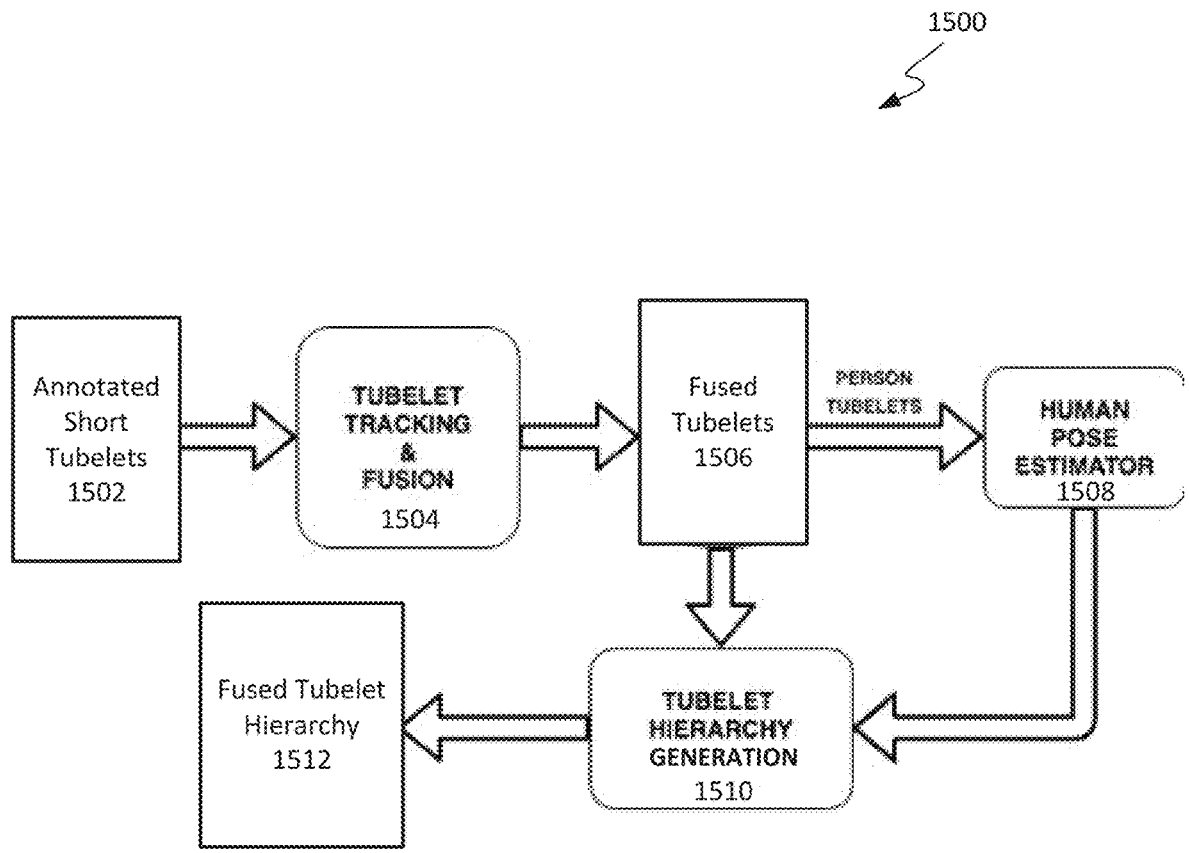
FIG. 15 is a block diagram showing the operation of an object tracker unit of the behavioural event generation subsystem of FIG. 11.

FIG. 15 illustrates a tubelet fusion and hierarchy construction process 1500 performed by the association and fusion unit 1112, which fuses the tubelets and builds a hierarchical model of the fused tubelets. Tracking and fusion is firstly performed (i.e. at step 1504) on the annotated short tubelet data 1502. For example, the object detector 1106 will attempt to detect potentially overlapping object classes such as person, face, arm, hand, bike, wheel etc. However, the object detector 1106 does not have an understanding of how its object classes are related and connected, and consequently produces short tubelets. The fusion component 1112 associates relates short tubelets to produce fused "long" tubelet data 1506.

In the described system, a "person" is the most important object which is to be detected and tracked by the system. In order to facilitate the association of tubelets classified as various body parts with the higher level tubelets classified as "person", the "person" tubelets are passed to a human pose classifier to estimate a pose associated with the tubelets (i.e. at step 1508). The pose estimator framework used in the described embodiments is OpenPose (see https://github.com/CMU-Perceptual-Computing-Lab/openpose), however the association and fusion unit may be configured to use other frameworks. The human pose estimation step 1508 will try to match a skeletal model to the image of a person and return the results as set of vectors that define a body pose.

Following human pose estimation for each detected person, the predicted location of the various body parts (faces, hands, arms etc) are matched to the location of nearby tubelets representing the corresponding classes (body parts) in order to generate a tubelet hierarchy (i.e. at step 1510). The partial, preliminary hierarchical information generated by the initial, two-level object detector 1106 is also taken into account at this stage to improve the robustness of object association and hierarchy construction. This process will, for example, allow for the association of eye tubelets with their corresponding face tubelets, and for the association of face tubelets with their parent body tubelets etc. This enables the construction of a fused hierarchical tubelet model 1512.

In the described embodiments, the fused tubelet data 1114 includes the tubelet hierarchy, associated image data and relevant features generated by the object detector. It contains all the information necessary for action recognition (as described below). In some embodiments, the features generated by the object detector 1106 are also stored in the frame detection storage unit 1104 and/or the annotated tubelet storage unit 1110. The type and form of the stored data may vary according to the implementation (e.g. to minimise computation time and/or storage requirements). However, all data required for action/emotion recognition is accessible using the tubelet as a reference irrespective of the storage implementation.

With reference to FIG. 11, the recogniser unit 1122 receives fused tubelet data 1114, and performs the identity recognition 1206, action recognition 1208 and emotion recognition 1210 steps of process 1200 depicted in FIG. 12. In some embodiments, processes 1206, 1208 and 1210 are performed sequentially, while in other embodiments the recogniser unit 1122 may be configured to execute the processes in parallel. Exemplary implementations of processes 1206, 1208 and 1210 as performed by the recogniser unit 1122 are described below.

Identity recognition is performed to identify a target person appearing within a fused tubelet as an individual monitored by the system (e.g. a student enrolled within the ADS 102). In the described embodiments, identity recognition is achieved via facial recognition. Factors influencing the accuracy of the facial recognition method implemented by the recogniser unit 1122 include: i) the number of unique individuals that potentially need to be identified; ii) the nature of the monitoring environment; iii) the size of the monitoring area; and iv) the number of frames which the target individual appears within (on average).

In relation to the above, for most implementations of the abnormality detection system described herein it can be assumed that:
 (i) the number of unique individuals that would need to be identified by a particular installation can be assumed to be fairly small (i.e. typically less than 100);
 (ii) the monitoring environment will generally be relatively static, with cameras in controlled locations and individuals mainly situated in a limited range of locations/positions;
 (iii) the surveyed area is of limited size and camera resolution can be adjusted to ensure imagery of adequate resolution can be collected for all locations of interest; and
 (iv) each individual will be seen in a large number of consecutive frames, consecutive tubelets and potentially from multiple viewpoints by multiple cameras. Combined with object tracking, tubelet association and viewpoint fusion, this will enable the use of statistical methods on top of per-frame identification to boost accuracy.

Given the above, the recogniser unit 1122 can be configured with a facial recognition module to perform facial recognition using a conventional recognition technique (e.g. Eyeris EmoVu), combined with data fusion and statistical averaging algorithms. This allows the BEG subsystem 160 to perform robust identification of pre-registered individuals present in the monitoring area. Depending on the facial recognition algorithm implemented, the recogniser unit 1122 may perform facial model training where a priori models are constructed for all individuals that require identification. This could involve, for example, students having their photo taken and added to the database of known individuals and the execution of a training algorithm on this database.

The input to the face recognition module consists of tubelets classified as containing human faces. A confidence measure for each individual image frame in the face tubelet is computed using a conventional face detector algorithm with support for confidence estimates. Alternatively, if using a face detector without support for confidence estimates, frames not detected as a face are assigned a confidence of zero.

The implemented facial recognition method is then applied to each frame in the face tubelet with a non-zero confidence value. The output of the face detector is, for each frame in the tubelet, an indication of a single individual, from the set of preregistered individuals, to whom the face in the frame corresponds.

The face recognition module assigns an identity to each particular tubelet based on the output of the face recognition algorithm. For each frame, the output is weighted by the confidence value assigned to that frame in the previous step, and the identity with the largest weighted sum is chosen as the identity of the particular tubelet. A normalised measure of identity confidence is saved for later use by the viewpoint fusion process (described below).

Action recognition is performed by the recogniser unit 1122 to label to a snippet (i.e., a number of consecutive video frames featuring the target individual) with a corresponding action class representing an action or emotion that is being performed, or exhibited, by the target individual. Conventional approaches to action recognition can be categorised as either: Two-Stream architectures approaches (Simonyan, Karen, and Andrew Zisserman, "Two-stream convolutional networks for action recognition in videos." Advances in neural information processing systems. (2014); Feichtenhofer, Christoph, Axel Pinz, and A. P. Zisserman, "Convolutional two-stream network fusion for video action recognition." (2016)) which use convolutional neural networks (CNNs) to incorporate both appearance and motion to recognize actions in a snippet; CNN+RNN Architectures (Donahue, Jeffrey, et al. "Long-term recurrent convolutional networks for visual recognition and description." Proceedings of the IEEE conference on computer vision and pattern recognition. 2015) which first extract informative features out of each frame of the snippet, then process all frames in a recurrent neural network (RNN) architecture to capture the long-term sequential dependencies between frames; and 3D Convolutional Neural Networks (Ji, Shuiwang, et al. "3D convolutional neural networks for human action recognition." IEEE transactions on pattern analysis and machine intelligence 35.1 (2013): 221-231; Tran, Du, et al. "Learning spatiotemporal features with 3d convolutional networks." Computer Vision (ICCV), 2015 IEEE International Conference on. IEEE, 2015) which process a stack of frames, ideally sequentially ordered, within a 3D CNN architecture.

The recogniser unit 1122 implements an action recognition module which is configured to recognise action classes including:
Hand gestures (e.g. raising, waving, clapping etc.);
Facial movements (e.g. frowning, smiling, blinking, speaking etc.); and
Body movements (e.g. standing up, sitting down, turning back etc.).

Pre-classification of each fused tubelet is performed to determine whether the tubelet contains a person, and if so the tubelet is processed by the action recognition module. In some implementations, the position of body parts and gestures also provides discriminative information for the action recognition module.

The action recognition module can be configured to utilise input information from a variety of different forms (or "modalities") to perform action detection and classification. These sources can include: 1) raw input frames; 2) feature maps from the initial object detector 1106; 3) tubelet data for tubelets labeled as "person"; and 4) the human body pose estimation information extracted during the tubelet hierarchy construction (i.e. at step 1508). Motion information is extracted from each snippet by computing the dense optical flow of consecutive frames in the raw video data.

In the described embodiments, the action recognition module is configured to receive input data including:
 (i) Features from video frames, which provide general appearance information about the whole action context. As an optimization specific to the proposed system, the lower resolution features used in the initial top level object detector 1304 are reused here.
 (ii) Features from optical flow as computed from the full frame video. Optical flow provides general motion information from the whole action context.
 (iii) Features from appearance feature maps inside the bounding box of the detected person. For this input, feature maps extracted from the higher resolution feature maps of the "sub-component" object detector 1306 are reused.
 (iv) Features from the motion feature maps inside the bounding box of the detected person. Motion feature maps are extracted from the full frame optical flow data of ii) above that lies within the bounding box of the detected person.

(v) Appearance feature maps extracted from within the bounding boxes of body parts associated with the detected person (as for (iii) above).

(vi) Motion feature maps extracted from within the bounding boxes of body parts associated with the detected person (as for (iii) above).

(vii) Skeletal frame outputs in vector format, extracted from the human pose estimation process (i.e. step 1508) for each frame in the action candidate snippet.

The video frame and optical flow features are extracted from a deep CNN (e.g., ResNet) which is pre-trained on both ImageNet and ActivityNet, and fine-tuned on a custom dataset tailored to the monitoring environment.

Figure 16:
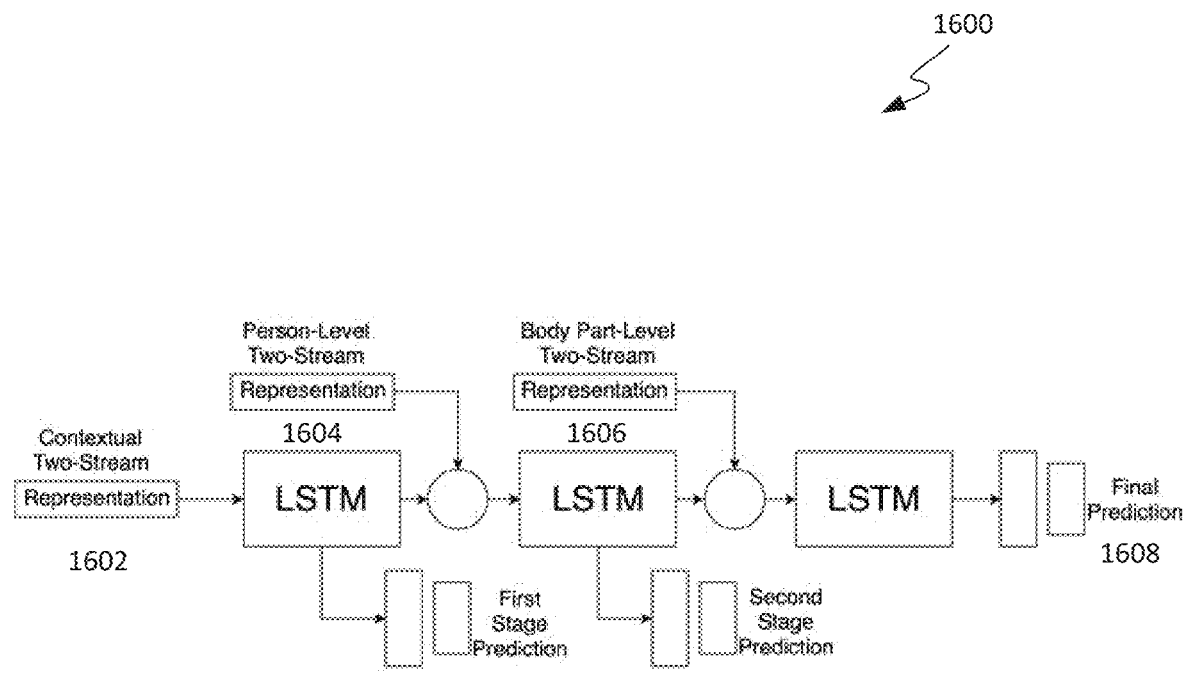
FIG. 16 is a block diagram showing a multi-stage Long Short-Term Memory (LSTM) Network for performing Action Recognition in accordance with the behavioural event generation subsystem of FIG. 11.

The action recognition module can be implemented according to a Multi-Stream Architecture to generate different levels of features. As shown in FIG. 16, the action recognition module 1600 includes: a Two-Stream network for contextual information 1602; a Two-Stream network for person-level information 1604; and a Two-Stream network for body part-level information 1606. Output of the last Two-Stream network will be crucial for determining human-related actions, while the first two Two-Stream networks provide useful hints about the motion scene and the people within it.

In the described embodiments, a three stage Long Short-Term Memory (LSTM) architecture (Aliakbarian, Mohammad Sadegh, et al. "Encouraging lstms to anticipate actions very early." Proceedings of the IEEE Conference on Computer Vision and Pattern Recognition. 2017) is used to connect the networks. LSTMs are chosen due to their suitability for modelling long term dependencies. This model first processes the context-aware features, which encode global information about the entire frame (output of first Two-Stream network 1602). The output of this first stage is combined with person-level features (output of second Two-Stream network 1604) to provide a refined prediction. Finally, the output of second stage is combined with body part-level information (output of third Two-Stream network 1606) to produce a final prediction 1608 of the human gesture-specific action. Note that, for more specific actions, such as human-object interactions or blinking, extra information can be added to another stage of LSTM. Note that, for blinking, we can still rely on estimated body pose and joints since there are two key-points for eyes.

The action recognition module is trained using a training data set of fixed-length snippets, where each snippet contains a single action. There are two stages of training, including: i) individual steam network training; and ii) LSTM level training. The first training stage involves training each of the Two-Stream networks for contextual representation, person-level representation, and body part-level representation respectively. In the described embodiments, this is achieved by fine-tuning a pre-trained ResNet classifier on frames of the action snippets. A conventional CNN training process is used, which is similar to the training processes employed to train a network for image classification using categorical cross-entropy loss function. The second training stage then involves training the multi-stage LSTM to utilise the trained two-steam networks for action classification.

The size of the training data set and the nature of the training data used to train the action recognition module can vary based on the accuracy needed by higher level analysis layers and the variability in the monitoring environments (if any) in which the system is deployed over. In a typical classroom application, it is expected that the action recognition module will benefit most from a training data set that includes a large amount of relevant, annotated data in order to accurately determine the parameters of the stack of networks. In the described embodiments, the training data set consists of several hundred varied and representative video snippets of each single action of interest (i.e. that can be recognised by the module). For other embodiments which perform recognition of a larger number of more complex action classes, a significantly larger training data set may be required (e.g. a set that includes well over a thousand snippets in each action class).

In some embodiments, the efficiency of the action recognition process may be improved by prefiltering the incoming "person" tubelets to discard the tubelets that contain little or no relevant actions. In the described embodiments, a first stage rejection mechanism is implemented using background subtraction to reject tubelets where no activity occurs. A second rejection stage is then performed to compute the optical flow sequence for the tubelet (which can be reused by the action recognition module in subsequently processing stages), which is used to apply a thresholding operation. A third rejection stage involves the use of a CNN that processes the sequence of image and optical flow frames associated with the threshold tubelet and classifies the snippets as containing an action or not containing an action.

The accuracy of the action recognition module, as represented by a Mean Average Precision (MAP) value, can be influenced by a variety of factors including, for example: the number of cameras in the monitor 110 (which may affect the ability to compensate for occlusion); the resolution of each camera 111-11N; the available computing resources of the detection server 120 on which the behavioural event generation subsystem 160 is executed; and the quality and quantity of the training data.

Validation experiments conducted on the large human motion database HMDB-51 dataset using the three-stage LSTM architecture classifier described above produced a recognition accuracy of approximately 80%. It is reasonable to expect that a similar level of accuracy can be achieved for implementations which are configured to recognise the set of actions described above (i.e. gestures, facial movements and body movements).

The validation experiments were conducted by running the action recognition module on snippets that contained an action that belongs to the expected set of actions (i.e. it does not properly account for false positives in the case of a snippets that don't contain any discernible actions, misclassification of actions that are not within the set of expected actions etc.). However, if classification is performed on snippets that contain no actions (i.e. "empty" snippets that have slipped through the prefilter) or only actions that the subsystem has not been trained to recognise, the accuracy may drop below 80%.

Based on the results of the validation experiments discussed above, the action recognition module can be expected to properly classify around 9 of 10 actual actions represented within active tubelets (given that the action represented by the tubelet is an action that is within the set of trained actions classes).

Emotion recognition is performed by the recogniser unit 1122 on tubelets which are determined to contain a representation of a human face. In the described embodiments, an emotion recognition module is implemented to execute a conventional emotion recognition algorithm that produces an indication of an emotion exhibited on the face of a target individual within the tubelet.

The emotion recognition module is trained using a publicly available dataset, such as the MMI Facial Expression Database (MMI Facial Expression Database, https://mmi-facedb.eu/) that contains video samples for six basic classes of emotions (happiness, sadness, anger, disgust, surprise, and fear). State of the art averaged class accuracy on this dataset is 78% when applied to video sequences containing well aligned, cooperative subjects (A Brief Review of Facial Emotion Recognition Based on Visual Information, http://www.mdpi.com/1424-8220/18/2/401/pdf). As for facial recognition, accuracy will drop significantly when the algorithms are applied to more varied, less constrained data. However, statistically useful results are likely to be obtainable by averaging classifications over multiple tubelets (and, if applicable, over imagery from multiple viewpoints).

Following the completion of the action 1208, identity 1206 and emotion 1210 recognition processes for a series of tubelets, the determined identity and classification data (including action and/or emotion classifications) is associated with each fused tubelet. The resulting data stream of fused, identified and classified tubelets 1116 is received by conversion unit 1118 (as shown in FIG. 11). The conversion unit 1118 firstly invokes a viewpoint fusion module 1117 which maps the tubelets into a common 3D space and fuses together tubelets which are associated with the same real world entity. For example, if an individual is visible in multiple cameras 111-11N of the monitor 110, then each camera 111-11N will generate its own tubelet and the viewpoint fusion module fuses these together. Identity confidence measures computed for each tubelet by the facial recognition module are used to create a final identity prediction.

Following viewpoint fusion, the conversion unit 1118 invokes the tubelet to viewpoint conversion module 1119 to convert the identified, classified tubelets into a high level representation suitable for long term storage and higher level analysis. This involves segmenting the tubelet into shorter snippets according to the actions detected by the action recognition module (as described above). Each snippet is then matched with the output of emotion recognition module (if any) to assign an indication of an emotion that is associated with the action. Matching is performed according to one or more matching criteria, such as for example timestamp information.

Following tubelet to event conversion, the conversion unit 1118 outputs the generated behavioural event data for each snippet. With reference to FIG. 12, the generated behavioural event data is stored in the action and emotion database 1120 (i.e. at step 1214). In the described embodiments, the behavioural event data includes: i) an identifier (ID) value which identifies the individual recognised within the snippet; ii) an indication of an action class representing the action performed by the identified individual (if applicable); iii) an indication of an emotion (or expression) representing the emotion exhibited by the identified individual (if applicable); and iv) a time duration of the snippet.

The behavioural event data is stored in the action and emotion database 1120 as a behavioural event record. Table 2 shows exemplary behavioural event records representing the stored behavioural event data. In this implementation, the database 1120 is configured to record timing information about the occurrence of the behavioural event, such as date and timestamp values, in addition to the event data features (i-iv) above. The records of the database 1120 are used to construct behavioural profile data for each individual monitored (i.e. during a behavioural profile training process, as described below).

TABLE 2

Example behavioural event records stored in database 1120.

| No. | Date | Timestamp | Duration (s) | Identity ID | Action | Expression |
|---|---|---|---|---|---|---|
| 11 | 2019 Apr. 1 | 14:34:56 | 8 | 23 | Picks up mobile device | Happy |
| 12 | 2019 Apr. 1 | 14:35:01 | 3 | 2 | Puts down book | Neutral |
| 13 | 2019 Apr. 1 | 14:35:20 | 4 | 0 | Walks to desk | N/A |
| 14 | 2019 Apr. 1 | 14:35:38 | 20 | 23 | Talks to (ID 0) | Surprised |
| 15 | 2019 Apr. 1 | 14:35:58 | 2 | 16 | Laughing | Happy |
| 16 | 2019 Apr. 1 | 14:36:12 | 5 | 23 | Leaves Surveyed Area | N/A |
| 17 | 2019 Apr. 1 | 14:41:47 | 4 | 16 | N/A | Confused |

With reference to FIG. 8, at step 810 the detection server 120 processes the detection data (i.e. the behavioural action and/or emotion events produced by the BEG subsystem), data representing the biometric profile of the student (for example, as retrieved by the DAPRC at step 908 for the detection of a behavioural characteristic), and the generated context data, to identify the presence of an abnormality of the individual (as described hereinbefore). Details of an exemplary action recognition subsystem which performs this function are included herein below.

Identifying an Abnormality from Behavioural Events

The generated behavioural event data is input into an abnormality recognition (AR) subsystem 170, as described below, which operates to recognise an abnormality by comparing long term trends of observed behavioural events, as represented by corresponding generated behavioural event data, to the appropriate behavioural profile of an individual.

Figure 17:
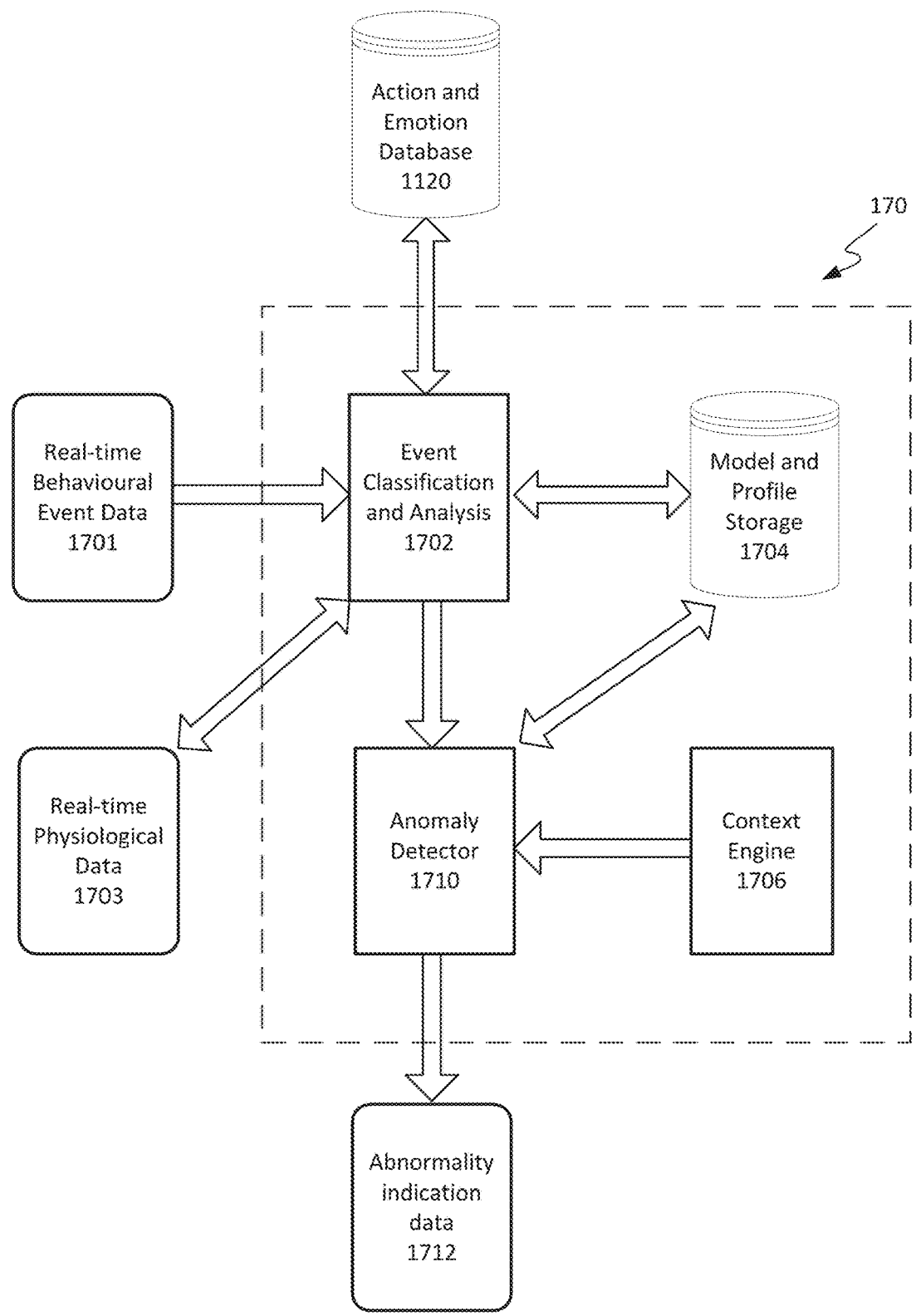
FIG. 17 is a schematic diagram of an abnormality recognition subsystem for the abnormality detection system of FIG. 7.

As shown in FIG. 17, the AR subsystem 170 includes an event classification and analysis unit 1702 which is in communication with a model and profile storage unit 1704 that maintains sets of high-level state models, and (individual specific) behavioural models (as described below). The AR subsystem 170 includes an anomaly detector unit 1710 which receives high-level state classification information generated by the event classification and analysis module 1702 (as described below) and context data from a context engine 1706 to determine the existence of an abnormality affecting an individual monitored by the system (as indicated by abnormality indication data 1712).

The event classification and analysis unit 1702 operates to process behavioural event data and produce activity state classifications based on particular sequences of events. The activity states represent high-level behavioural categorisations of an individual, as inferred from the behavioural events that are observed from monitoring the individual over time.

Figure 18:
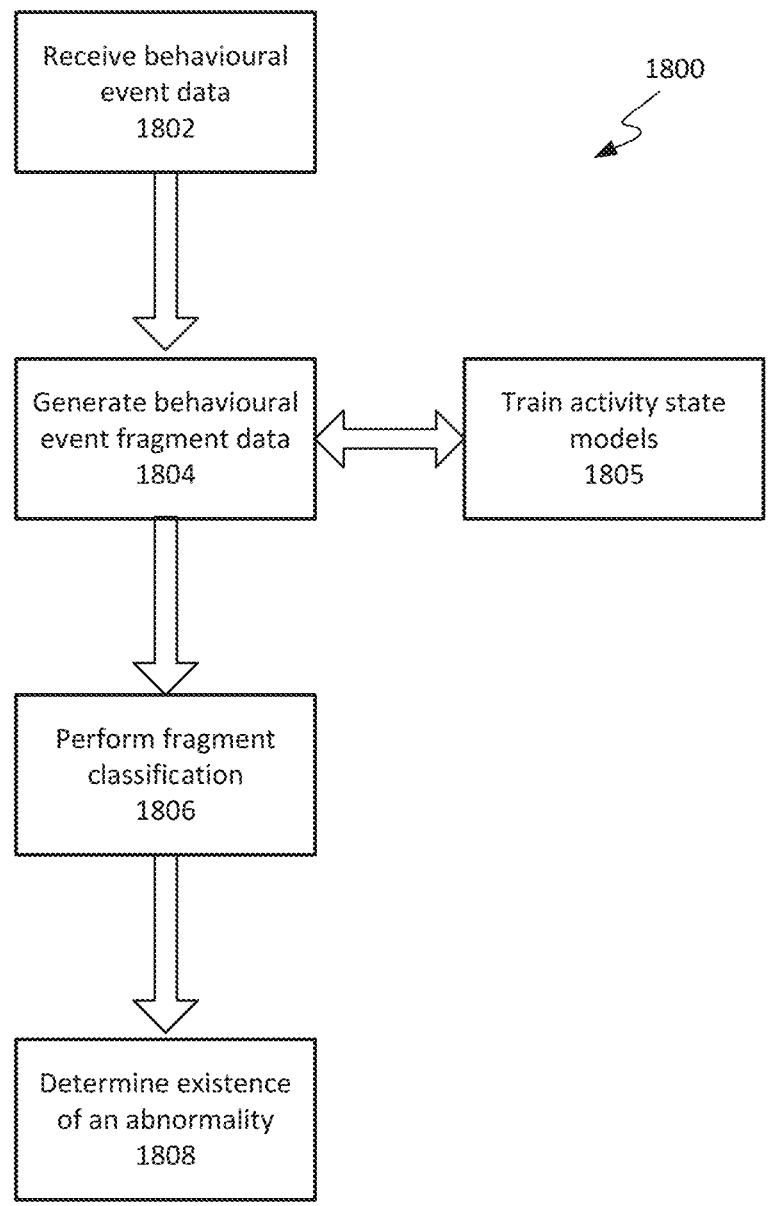
FIG. 18 is a flow chart of an example of a method for high-level behavioural categorisation and abnormality determination for an individual monitored by the system, as performed by the abnormality recognition subsystem of FIG. 17.

FIG. 18 illustrates the process 1800 by which the AR subsystem 170 performs high-level behavioural categorisation and subsequent abnormality determination for an individual monitored by the system. At step 1802, the event classification and analysis module 1702 receives behavioural event data generated by the BEG 160 representing instances of action and/or emotion events identified for a particular individual. The behavioural event data includes event data generated in real-time 1701 by the BEG 160 and event data stored in the action and emotion database 1120.

Behavioural Event Fragments

A sequencing process is applied to organise the behavioural event data based on the time of occurrence of each event to produce a series of event vectors $\{e_1, e_2, \ldots e_M\}$. Each event vector has elements representing the value of the time of occurrence of the event, the duration of the event, an indicator of the action and/or emotion class for the event.

At step 1804, the event classification and analysis unit 1702 generates event fragments $\{ef_1, ef_2, \ldots ef_P\}$ from the sequenced event vectors. Each behavioural fragment represents a collection of sequentially occurring behavioural events. In the described embodiments, overlapping sequential time windowing is used to form fragments from corresponding sets of considered behavioural events. One or more behavioural fragments are generated for each considered set by applying a fragment window of a fixed duration (e.g. 60 seconds) and overlap (e.g. 30 seconds) to each considered event set such as to generate a fragment that captures all corresponding events that occur within the window. In some embodiments, such as during model training (as described below), the considered set of behavioural events are the events which occur within a given observation window, which is of a predetermined size (e.g. 1 hour) and may be defined over a particular time period that has past (i.e. where the observation window is applied to process event data from entries stored in the action and emotion database 1120). In other embodiments, the observation window may be defined dynamically, such as to include event vectors generated from behavioural event data 1701 that is received in real time from the BEG 160.

Each behavioural fragment represents the behaviour exhibited by an individual over a continuous period of time (i.e. the duration of the fragment window) within the observation window. Since there may be a time gap between adjacent sequential behavioural events that are grouped to form a fragment, the event classification and analysis unit 1702 is configured to define a NULL event indicating that no action or emotion was detected (for a particular individual) over a specified time (i.e. between the event occurrence time and an end time defined as the occurrence time+the duration of the event). Each behavioural fragment can include one or more NULL events, such that the fragment covers the length of the fragment window.

Figure 19:
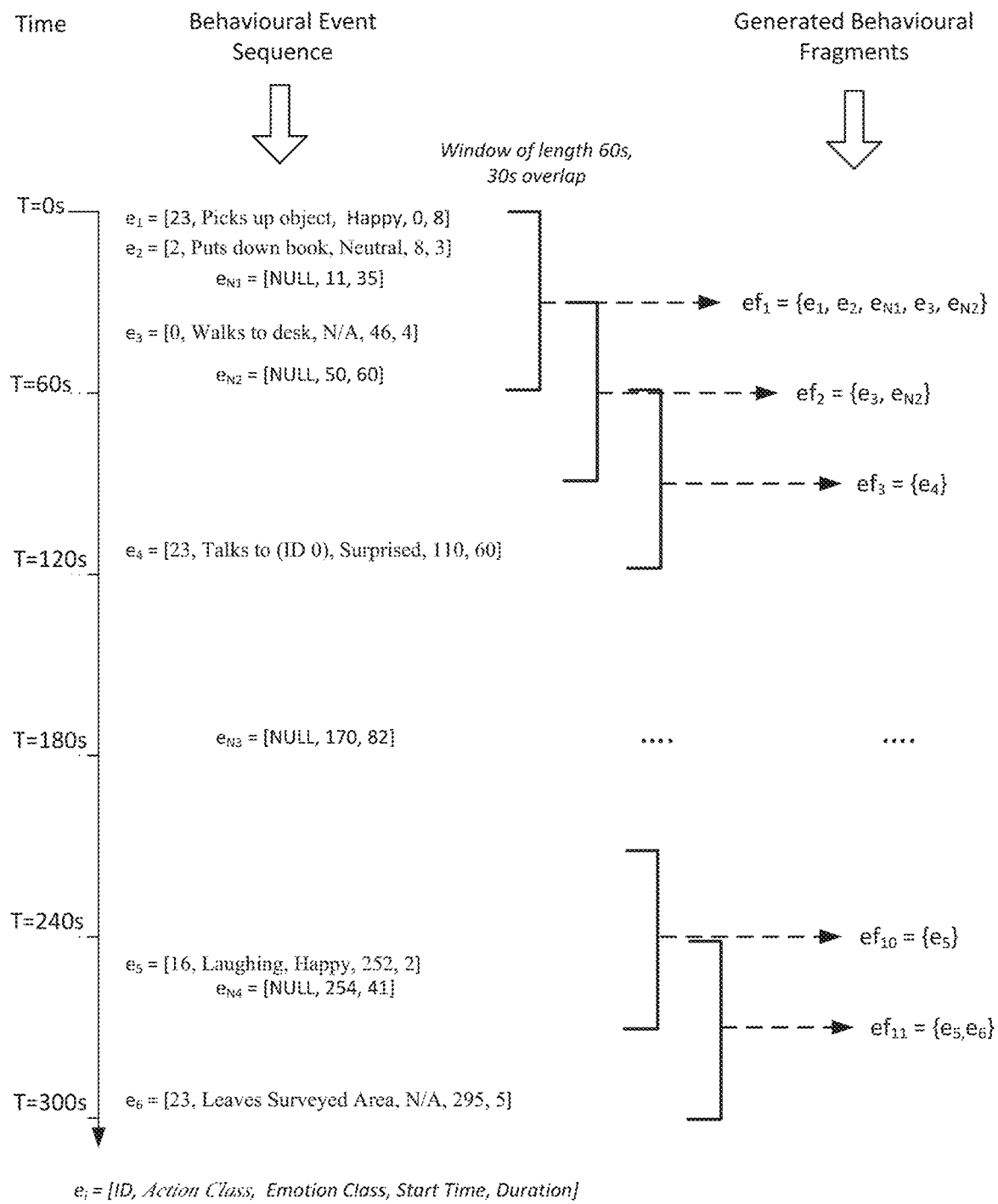
FIG. 19 is a schematic diagram showing an example of a behavioural fragment generation process performed by the abnormality recognition subsystem of FIG. 17.

FIG. 19 illustrates behavioural fragment generation for a set of action behavioural events $e_1$ to $e_6$ which occur over a 5 minute observation window. The fragment window size is set to 1 minute with a 30 second overlap, resulting in the generation of 11 fragments $f_1, \ldots, ef_{11}$. Each event is represented by data including an identifier (ID) of the individual, the action class, the emotion class, the event start time, and the event duration. As shown in FIG. 19, the event classification and analysis unit 1702 generates NULL events $e_{N1} \ldots e_{N4}$ to bridge the time gap between consecutively occurring action events $e_1$ to $e_6$ prior to grouping the action and null events that fall within each overlapping window.

The behavioural event sequencing and fragment generation processes (as performed in steps 1802, 1804) can be performed with events associated with any individual monitored by the system (i.e. when the subsystem operates in a training mode as described below), or specific to each individual. That is, by producing a series of behavioural fragments from the behaviour events logged by the BEG subsystem 160, the AR subsystem 170 is able to express the behavioural characteristics which are exhibited by each individual, or by the monitored population in general, over contiguous time intervals of arbitrary lengths.

In the described embodiments, fragment generation is also specific to the particular type of behavioural event(s) that is represented by the corresponding event data. Separate sets of fragments are generated for action events and emotion events based on behavioural event data which represents the occurrence of, at least, behaviour of the specified type. For example, fragment generation performed on the data represented by the records in Table 2 involves generating emotion behaviour fragments using records 11-17, but not records 13 and 16 (where only an action is represented).

Activity State Modeling and Fragment Classification

With reference to FIG. 18, at step 1806 fragment classification is performed in order to relate the generated behavioural fragments to one or more activity states, therefore providing a high-level categorisation of the behaviour of an individual based on their time sequential observed event behaviours. The event classification and analysis unit 1702 defines a set of activity states each corresponding to a high-level categorisation of particular action and emotion behaviour that is detected by the BEG subsystem 160. In the described embodiments, activity states are defined for action (i-iii) and emotion (iv-vi) type behaviours, including: i) physical; ii) personal interaction; iii) class participation; iv) positive emotion; v) neutral emotion; and vi) negative emotion.

The event classification and analysis unit 1702 maintains a set of activity state models for each activity state. Prior to classification, the activity state model parameters are trained on behavioural event fragments (i.e. at step 1805) from a training data set. In the described embodiments, supervised model training is performed using the training data set which includes fragments representing sequences of behavioural events associated with one or more individuals. That is, the activity state models are universal models (as opposed to individual specific models) which represent a generic high-level abstraction of event class actions or emotions over the whole population of monitored individuals.

Each fragment of the training set is labelled in relation to one or more of the activity state models via a transcription process. The labelling process varies based on the type of modelling performed and the corresponding classification technique employed. The transcription process can occur dynamically during the compilation of the training data. Specifically, the AR subsystem 170 can be operated in a training mode in which the event classification and analysis unit 1702 presents generated behavioural fragment data to a user of the system (such as a teacher) allowing the user to assign classification labels to the fragment indicating the extent to which the fragment is representative of one or more activity states.

For example, consider the action behavioural fragment ef1={e1, e2, e3, e4}, where e1=a "running across the room" action event from t=0 to 10s, e2=a NULL event from t=10s to 20s, e3=an "engaging in play" action event from t=20s to 180s, and e4=a "sitting in the corner" action event from t=180s to 300s. For a training process in which the assigned classification label is an indication of the activity state(s) to which the fragment corresponds, the teacher may transcribe the fragment as a sample of both the physical and personal interaction states.

In other embodiments, the event classification and analysis unit 1702 can be configured to operate in an automated training mode, in which behavioural fragments are automatically transcribed based on the data values of their constituent behavioural event vectors. Dynamic transcription can be configured by defining one or more rules for the association of behavioural event classes (as defined by the BEG subsystem 160) to corresponding activity states. For example, with respect to the example fragment ef1 above during automated training the unit 1702 may calculate that the subject of the fragment spent 3.33%, 53.33%, and 40% of the time performing each respective event action, and assign training labels (e.g. indicating the personal interaction activity state) to the fragment accordingly without user intervention.

In the described embodiments, event class to activity state association rules are expressed as a 2D class association matrix stored within a data module of the event classification and analysis unit 1702. The values of the class association matrix indicate a correlation between each event class and the activity states defined by the system. Other data structures may be used to store event class to activity state association data depending on the implementation.

The form and type of the activity state models can vary according to the fragment classification algorithm used in step 1806. In one possible implementation, each activity state model is represented by a conventional multilayer perceptron neural network (MLP-NN). Supervised network training is performed according to a "one vs all" approach in which the training data is dynamically partitioned into sample fragments which are indicative of the particular activity state (as determined by the labelling process), and those which are not. The number of internal nodes is chosen according to the implementation in order to balance the competing factors of recognition accuracy, and model storage requirements and recognition evaluation speed. The use of sigmoid based activation functions has been shown to provide improved performance, compared to binary step functions, when NNs are used in similar pattern classification tasks (such as image classification).

To train each model, the training data fragments are processed to determine the network parameters (i.e. the weights of the nodes) using standard techniques (such as, for example, back propagation). The feature dimensionality is fixed and equal to the product of the dimensionality of the behavioural event fragments and the behavioural event vectors (i.e. for each behavioural fragment, the raw concatenated event vector data is fed into the network as input). In this implementation, the activity state model data consists of a single trained NN for each of the states (i-vi) outlined above.

The event classification and analysis unit 1702 stores the activity model data (i.e. the NN parameter values according to the above described implementation) in the model and profile storage unit 1704. In the described embodiments, the model and profile storage unit 1704 is a database that is accessed by the event classification and analysis unit 1702 via a database management system. Model training is performed offline in a training mode, which is executed at least once prior to the monitoring of the individuals for the purpose of abnormality determination.

In an alternative implementation, statistical modelling is used to represent each activity state. For example, each activity state model can be represented by a set of Gaussian Mixture Models (GMMs) or Hidden Markov Models (HMMs). In such embodiments, the model set includes a discrete number L of submodels which define levels or degrees of the activity respective state. With L=3, each activity state is defined by a set of 3 submodels that correspond to 'high', 'moderate' and 'low' levels of the activity state. The parameters of each submodel are trained using conventional techniques, such as, for example, a form of expectation maximisation for GMM submodels. Training is supervised using transcribed fragment data which is labelled according to the activity state represented by the data, and with an indication of the degree of that state. For example, the action behavioural fragment ef1 described above may be labelled as belonging to the personal interaction activity state, and may be assigned a 'high' degree. Fragment ef1 would therefore be used as a training sample for the 'high' submodel of the personal interaction activity state model.

Figure 20:
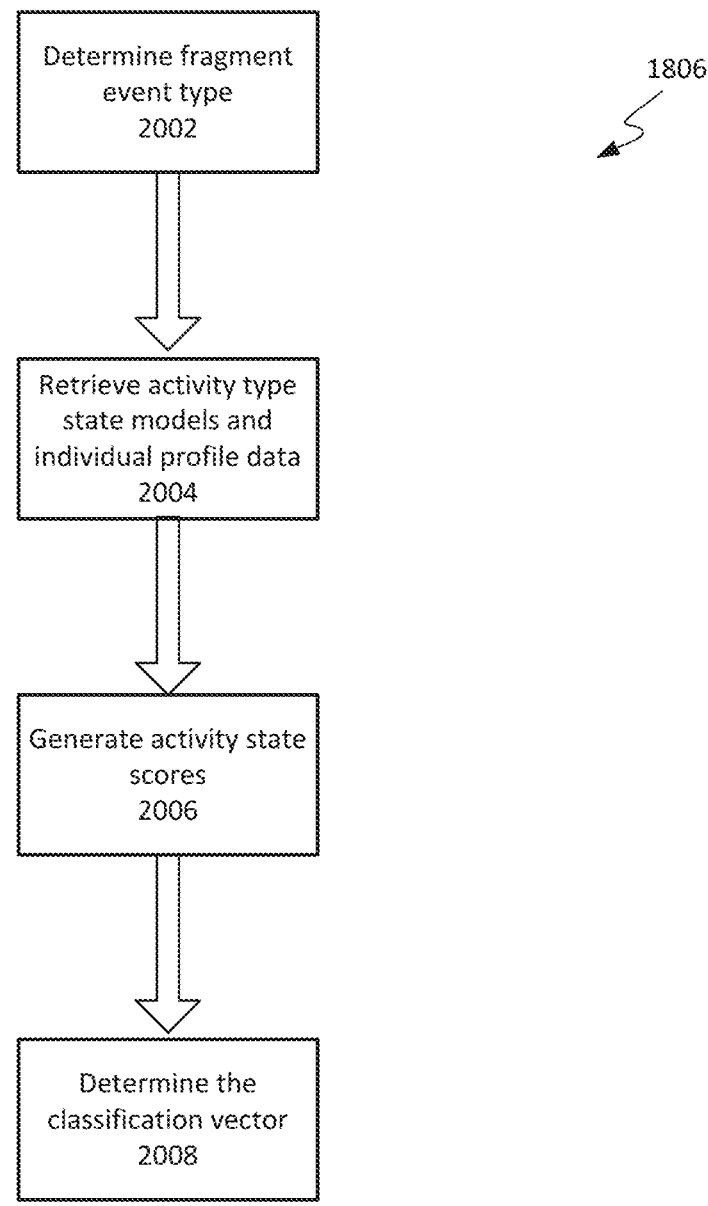
FIG. 20 is a flow chart of a method for performing behavioural fragment classification during the behavioural categorisation and abnormality determination process of FIG. 18.

Following model training, fragment classification is performed (at step 1806) on new behavioural event fragments that are generated by the event classification and analysis unit 1702 in order to translate the fragment (i.e. the time sequential action/emotion events) into a high-level activity representation. FIG. 20 summarises the fragment classification procedure as conducted by the event classification and analysis unit 1702. At step 2002, the fragment event type is determined as either being an action event type or an emotion event type. Based on the event type determination, at step 2004 the event classification and analysis unit 1702 retrieves the corresponding activity state model data from the model and profile storage unit 1704.

In the described embodiments, behavioural and emotion activity states are modelled separately such that the fragments which are applied to these models (i.e. during training or recognition) contain events of either an 'action' or 'emotion' type. Separating the activity state models allows the AR subsystem 170 to model actions and events independently, and allows for the abnormality determination process (discussed below) to proceed based on deviations detected from an individual's nominal actions and/or emotions. This can be advantageous when the amount of training data is limited for one type of behavioural event, but not the other.

For example, where there is ample training data representing action events but sparse amounts of data representing emotion events (at either the universal or individual specific levels), separation of the models allows for an accurate action model to be trained and for this model to be given higher weight in the abnormality determination processes (compared to the emotion models, which can be expected to be less accurate). The skilled addressee will recognise that, in other embodiments, it is possible to jointly represent the behavioural action and emotion features in a single model. In such embodiments, behavioural events would not need to be segregated for the purpose of producing distinct 'action' and 'event' fragments.

At step 2006, the fragment is classified against each activity state model to produce a set of activity state scores or classification values. Specifically, the classification of a candidate fragment results in the generation of single output value for each activity state. The form of the activity state scores varies depending on the type of classification method implemented. For implementations using MLP-NNs as the activity state models, the output value is a real number. For implementations using statistical classifiers, such as HMMs/GMMs, the output value is an indication of a discrete level corresponding to the activity state (e.g. indicating 'high', 'moderate' or 'low' as described above). In the described embodiments, the output values are concatenated to produce a fragment classification vector consisting of three values (one for each of the three action or emotion states, depending on the fragment event type).

At step 2008, the activity state scores are combined to produce the fragment classification vector as described above. The fragment classification vector for a behavioural event fragment represents the high-level categorisation of the fragment in the activity state space. For example, inputting the action behavioural fragment ef1 described above into each action activity state MLP-NN model produces a 3 dimensional fragment classification vector vef with higher relative scores for the physical and personal interaction states compared to the class participation state. From this classification vector, it can be inferred that the individual is exhibiting a reasonable level of physical activity, a high level of interactivity with fellow individuals, and a low level of class participation.

Determining an Abnormality

With reference to FIG. 18, at step 1808 fragment classification vector data produced from the classification of a fragment consisting of observed behavioural events exhibited by an individual (referred to as "observed activity state data") is processed by the anomaly detector 1710 to determine the existence of a behavioural abnormality associated with the individual. The anomaly detector 1710 receives the observed activity state data from the event classification and analysis unit 1702, in conjunction with data representing the nominal behaviour of the individual with respect to the relevant activity states. The anomaly detector 1710 matches the observed activity state data to the nominal activity data in order to determine whether an abnormality exists, as described below.

In the described embodiments, the nominal activity data is stored within a behavioural profile of the individual and includes nominal action and emotion models which model the normal, or expected, behaviour for the individual in terms of the activity states of each type (i.e. action and emotion). Unlike the activity state models used to produce fragment classification data, the nominal action and emotion models are individual specific. For example, consider the implementation described above involving action and emotion activity states (i-vi), and as deployed to monitor two students Johnny and Jane. Jonny has an extroverted personality and has attention deficit hyperactivity disorder. Accordingly, his behavioural profile includes a nominal action model which reflects that he typically exhibits a 'high' level for the physical activity and the personal interaction states. Jane is introverted but is otherwise energetic. Her behavioural profile includes a nominal action model which reflects that she typically exhibits a 'high' level for the physical activity state but a 'low' level for the personal interaction state.

The nominal action and emotion models have an input feature space corresponding to the components of fragment classification vectors (i.e. a dimensionality of 3 in the described embodiments), and are defined by parameter data according to the specific classification technique implemented by the anomaly detector 1710. A number of conventional pattern classification methods are suitable, such as NN based classifiers or statistical classifiers (e.g. GMMs/HMMs) as discussed above for universal activity state modelling. Supervised training is performed to determine the nominal action and emotion model parameters for each individual. The training data includes a set of fragment classification vectors which collectively represents the normal behaviour of the individual across the activity states of the given type (e.g. the degree of physical activity, personal interaction, and class participation for the action type). In the described embodiments the nominal models are trained by the event classification and analysis unit 1702 during a training mode of operation in which the subsystem receives input from a user (such as a teacher), similarly to that described above.

Figure 21:
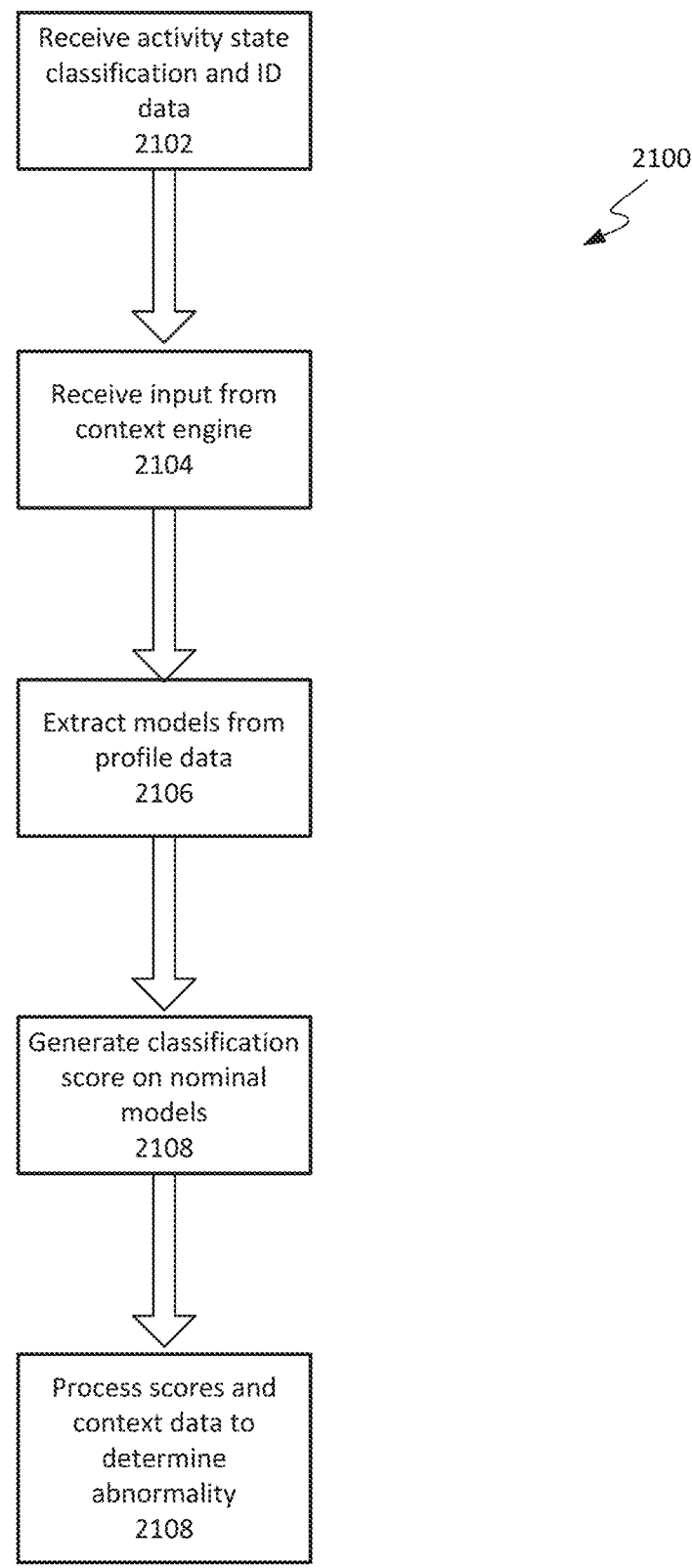
FIG. 21 is a flow chart of a method for determining the presence of a behavioural abnormality for an individual based on behavioural fragment classification, as performed by the abnormality recognition subsystem of FIG. 17.

FIG. 21 illustrates the process performed by the anomaly detector 1710 to determine the presence of a behavioural abnormality for an individual. At step 2102 the anomaly detector 1710 receives input data from the event classification and analysis unit 1702, including:
 (i) observed activity state data in the form of at least one fragment classification vector representing a high level characterisation of a sequence of behavioural action or emotion events exhibited by an individual (i.e. as represented by the fragment); and
 (ii) an identifier of the individual uniquely specifying that individual within the system.

The anomaly detector 1710 also receives input from the context engine 1706. Context engine 1706 defines and tracks conditions that are relevant to whether an abnormality may be affecting individuals monitored by the system. As described above, the conditions can include factors influencing the learning environment, such as the type of class or session being undertaken, and/or environmental factors (e.g. the ambient temperature within the environment). In the described embodiments, the context engine 1706 is configured to define the relationship between conditions of relevance (e.g. the type of class, weather conditions, whether an exam/test is being sat by the class, etc.) and the activity state levels which characterise an individual's behaviour (e.g. physical activity, personal interaction, class participation, etc.).

For example, the context engine 1706 may define a strong positive relationship between the type of class being a gym class and a 'high' level for physical activity. Data maintained by the context engine 1706 includes: i) condition specification data (e.g. 'Class type currently in progress'); ii) an indication of a present value for the condition (e.g. 'gym class'); and iii) condition modifier data indicating the affect that the present value of the condition has on each activity state.

The context engine 1706 determines the present value for the condition dynamically from condition notification data which can be received as input from the teacher, or from another subsystem. The condition modifier data is generated from an association table which maps each possible value of the condition to a corresponding effect for each activity state. For example, in some embodiments the modifier data may be a positive real number (0,□) that is used by the anomaly detector 1710 to weight the individual scores produced by the activity state classification data on the individual's nominal model (as described below).

At step 2104, the anomaly detector 1710 receives input from the context engine 1706 including, at least: condition specification data for conditions that are relevant to the monitoring environment; and condition modifier data indicating the affect that the present value of the event/condition has on each activity state. At step 2106, the anomaly detector 1710 retrieves, from the model and profile storage unit 1704, profile data of the identified individual. The nominal behavioural activity model data is extracted from the profile data.

Classification is performed for each fragment classification vector of the observed activity state data using the nominal action or emotion model of the individual. For each fragment classification vector, a set of matching scores are produced from the classification operation on the nominal model (which is the action model if the fragment is an action type fragment, or the emotion model if the fragment is an emotion type fragment). The matching scores are represented as a matching score vector of 3 components in the described embodiments (i.e. each component being the classification score obtained from one of the nominal action (or emotion) models).

At step 2108, the anomaly detector 1710 processes one or more of the generated matching score vectors in order to determine whether a behavioural abnormality exists. The matching score values are augmented by the context modifier data received from the context engine 1706. For example, in a case where the condition 'Class type currently in progress' has a value 'gym class' the condition modifier data may be applied to de-emphasise the matching score of the physical activity state model component (since it is expected that the physical activity of individuals in the environment will be elevated as a consequence).

Abnormality determination then proceeds by generating an overall matching score from the activity state component specific scores. The combination strategy used will depend on the classification technique implemented. For example, in the case of statistical classification an overall likelihood score $L(c|\lambda_a)$ can be produced from individual likelihood scores $\rho(c_1|\lambda_a) \ldots \rho(c_3|\lambda_a)$ by weighted summation (see FIG. 22).

The anomaly detector 1710 compares the calculated overall matching score to a corresponding matching threshold value, where the threshold represents the lowest overall classification score for the individual's observed behaviour to still be considered normal. The matching threshold value can be determined by the anomaly detector 1710 according to a desired confidence interval (e.g. such that scores fall below the threshold if they are outside of a 95% confidence interval of the corresponding model). Determination of the threshold value is configurable by a user of the AR subsystem 170 such as to control the level of sensitivity of the abnormality detection process. For example, it may be desirable to widen the interval of acceptable matching scores in implementations where the nominal models have been trained on sparse data, or where there are other factors which increase the difficulty of obtaining an accurate high-level behavioural classification for individuals (e.g. where there are many individuals to be monitored, and many action and/or emotion classes).

If the calculated matching score is below the threshold, then an anomaly is deemed to exist with respect to the particular fragment classification vector. In some embodiments, the presence of an anomaly for a single fragment classification vector is sufficient to determine that an abnormality is affecting the individual. In other embodiments, the determination of an abnormality requires the detection of anomalies for multiple fragment classification vectors spanning a predetermined time interval.

When an abnormality is determined, the anomaly detector 1710 generates abnormality indication data 1712 which indicates the occurrence of the abnormality to other subsystems of the ADS 102. In the described embodiments, the abnormality indication data 1712 includes: i) an indication of the individual affected by the abnormality (e.g. the individual's ID value); ii) an indication of the values of the behavioural activity states associated with the fragment(s); iii) a corresponding time period in which the abnormality occurred; and iv) condition specification data for any conditions that are relevant to the monitoring environment when the abnormality occurred.

Figure 22:
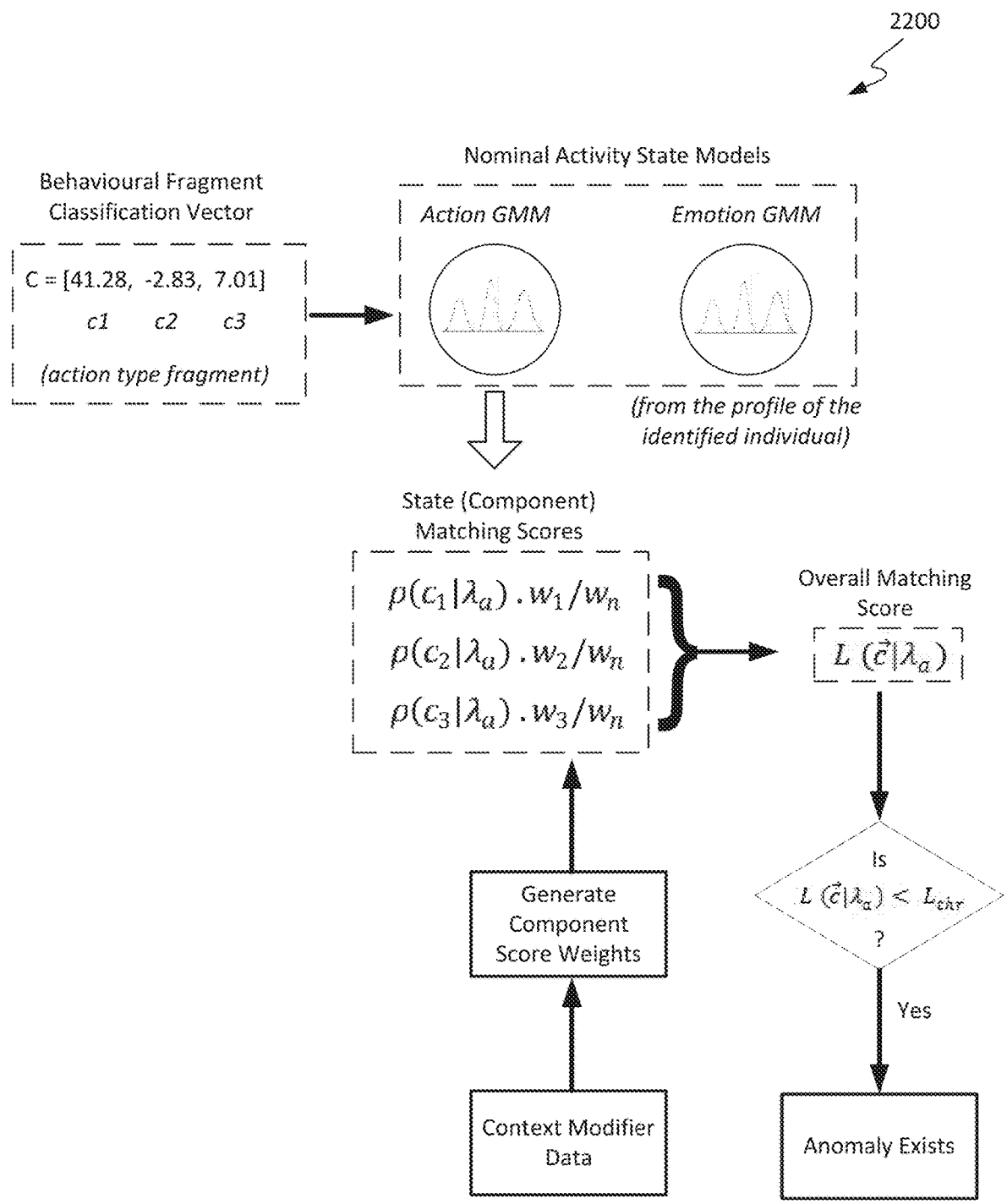
FIG. 22 is an example of performing behavioural abnormality determination with a particular implementation an anomaly detector of the abnormality recognition subsystem of FIG. 17.

FIG. 22 illustrates an example of the above described classification process for observed activity state data comprising a single behavioural classification vector $\vec{c}=\{c_1, c_2, c_3\}$ of the action type. For each individual, the nominal action and emotion models are GMMs $\lambda_a$ and $\lambda_e$ depicted with a single mixture per component, where the components $c_1, c_2, c_3$ correspond to the activity state values (e.g. the classification scores for the 'physical', 'personal interaction' and 'class participation' states for the action model). Classification of the vector $\vec{c}$ on the nominal action model $\lambda_a$ produces component level matching score vector $\{\rho(c_1|\lambda_a), \rho(c_2|\lambda_a), \rho(c_3|\lambda_a)\}$. The context modifier data is used to weigh each component of the matching score vector (i.e. likelihoods $\rho(c_i|\lambda_a)$, i=1 . . . 3) by a corresponding weighting factor $w_i/w_n$, where $w_n$ is a normalisation value (e.g. $w_n=\Sigma w_i$). The matching score vector components are summed to produce a total likelihood score $L\rho(\vec{c}|\lambda_a)$ for the classification of vector $\vec{c}$ on model $\lambda_a$, which is then compared to threshold value $L_{thr}$ for anomaly detection.

With reference to FIG. 17, in some embodiments the AR subsystem 170 is configured to receive physiological data 1703 representing physical characteristics of individuals monitored by the system. The physiological data can be in the form of physiological events representing changes in a physiological parameter of the individual (such as their head and/or body temperature). Windowing is applied to organise the physiological events into time contiguous sequences (i.e. physiological event fragments), as described above for the behavioural events.

The event classification and analysis unit 1702 is configured to provide the anomaly detector 1710 with observed physiological state data, which is produced by classifying physiological event fragments using pre-trained models for a set of physiological states. In the described embodiments, the physiological states include head temperature, extremity temperature (such as hands), and body temperature. The anomaly detector 1710 matches the observed physiological state data to a nominal physiological model of the identified individual to produce matching scores similarly to the process described above for the behavioural abnormality determination. An overall matching score is then calculated based on a physiological matching score vector, allowing a comparison to be performed between the calculated overall matching score and a threshold value.

Anomalies in the observed physiological state data can be detected based on the comparison result, and a (physiological) abnormality is determined when an anomaly is detected within at least a given fixed number of physiological fragment classification vectors, as described above for the processing of the behavioural data.

Generation of the observed physiological state data from the physiological fragment data may involve different processing steps compared to the generation of the observed behavioural activity state data. For example, in detecting the head and body temperature characteristics, the detection server 120 may compare detected values of the student's head/body temperature with an average head/body temperature of the class, and offset the deviation based on the student's biometric profile (according to the methods described herein hereinbefore). In some cases, a 2% difference in a child's temperature from the rest of the class after the offset may be taken by the system as insignificant, whereas a 5% difference after the offset may indicate a potential problem, and would therefore result in the determination of an abnormality.

The detection server 120 is also configured to detect differences in body temperature between different parts of the body, for example, between the hand and the head. A consistently high temperature throughout the body may be caused by a recent activity of the student, e.g., the student has been running, whereas a relatively higher temperature in the head may indicate illness. Accordingly, in some embodiments the server 120 may also be configured to trigger an alert (i.e. detect an abnormality) when the difference between the head temperature and the hand temperature exceeds a predetermined threshold, while ignoring an insignificant increase in the overall body temperature (in accordance with the critical event reporting processes described herein). This can be achieved, for example, by modelling the temperature differential as a separate physiological state variable in the above described processes.

Similarly, when detecting heart rate, an increased heart rate may be caused by the student's recent physical activity. The detection server 120 can compare the detected heart rate with the average heart rate of the whole cohort, and offset the deviation based on the student's biometric profile.

The heart rate may be detected for a continuous 15-second period simultaneously for a whole group of students. If the system fails to obtain a continuous 15-second heart rate of a particular student, it may start the detection process again for that student only, until a valid result is obtained.

In another example, the frequency of a child scratching his/her head may be detected as a behavioural characteristic (as described hereinbefore), and a high frequency of a student's head scratching against their regular pattern and an average frequency of the whole cohort may suggest a lice infection, and may be detected as an abnormality by the system. The system 102 may trigger an alert or send a notification to the teacher, to enable the affected student to be removed from the class (in accordance with the processes described herein).

As another example, a low frequency of hand-raising by a student, as compared to a frequency that is indicated as normal by the student's profile, may also be detected as an abnormality, subject to the determined context of this behaviour (as described hereinafter).

Selective Monitoring and Integration with Facilities

Further, in some embodiments the ADS 102 can be configured to perform monitoring and detection activities for one or more selected students. For example, by only detecting behavioural characteristics of these students, or detecting more behavioural characteristics of these students compared to the whole class. This may be used to monitor inappropriate behaviour of one or more particular selected students. In some embodiments, the system 102 may be configured to monitor more biometric or behaviour characteristics for selected students than other students.

The system 102 can also be configured to detect a student's interaction with other people based on predetermined behaviour characteristics. If it is detected that a student is spending more time alone than usual, the system 102 may identify a behavioural abnormality, and may send a notification to the relevant teacher or welfare officer regarding the abnormal behaviour to allow further investigation of the situation. Context data representing the student's environment may be used to determine whether the student's interaction (or lack thereof) with other people constitutes a behavioural abnormality.

For example, a lack of interaction representing the student spending more time alone than usual when the student is in a particular area where social activity is expected (such as a playground or a cafeteria) may result in the identification of an abnormality, while a lack of interaction detected in another area (e.g., a classroom) may not.

Further, the detection of the student's behavioural characteristics may be used in the detection of the student's physical characteristics. For example, the detection of heart rate may be started after the student has been seated.

In some embodiments, the detection of particular behavioural or physical characteristics is used for controlling one or more facilities of the school. For example, the detection server 120 can be configured to transmit detection event data to the BPMS server 130 when particular behavioural characteristics are detected. The BPMS server 130 can be configured to process the detection event data to perform particular functions in relation to the facilities, such as for example locking and/or unlocking doors adjacent to, or within, the monitoring area for students whose amount of physical movements is significantly lower than other students.

Contextual Rules and Abnormality Reporting

In identifying an abnormality (i.e., at step 810), the DAPRC can be configured to interpret one or more attributes indicated by the context data as rules, or conditions. For example, without considering the context data, a decrease in the frequency with which a student raises their hand during class, compared to the frequency of hand raising which is expected of the student based on their behavioural profile, may result in the identification of an abnormality (e.g., indicating the possibility of an issue, such as domestic troubles or bullying). However, an indication that the class or session being undertaken in the monitoring area is an exam or test can be interpreted as a condition which prevents the determination of an abnormality associated with the detected lack of class participation.

In other embodiments, the context data can be used during the comparison between the detection data and the corresponding biometric profile data (such as, for example, as an input to a pattern classification process). This allows a weight to be assigned to attributes indicated by the context data (such as the type of instruction being undertaken in the monitoring area—e.g., a regular class, or an exam), as opposed to using these attributes as rules or conditions which prevent or allow the identification of particular abnormalities.

The DAPRC can be configured to utilise the generated context data to determine one or more models of the student's biometric profile which are to be used to identify the abnormality (i.e., by comparison with the detected physical or behavioural characteristics). For example, the thermal model to be used for identifying an abnormality based on the detected thermal signature (i.e., "pattern") of a student can be determined from calendar or timetable data. Each student may have several thermal profile models depending on their previous classes and/or activities in the learning environment (e.g., a normal profile model, an after-lunch profile model, and an "after-sport" profile model). The number of required models may vary depending on the application.

At step 812, the detection server 120 reports the identified abnormalities to the BPMS. The DAPRC invokes the ANC to generate update report data for reporting the physical and/or behavioural characteristics of one or more students to the BPMS server 130. The reporting process of step 812 can be configured to occur as part of: a scheduled abnormality reporting process in which abnormalities that have been identified during a particular period of time (e.g., over the course of a school day) are processed and transmitted to the BPMS as a batch; and/or a dynamic abnormality reporting process in which the update report data is transmitted from the ANC to the BPMS server 130 in real-time (i.e., as an abnormality is identified for a student).

Scheduled reporting can be configured to occur over an arbitrary time period as required by the user of the ADS 102 (e.g., on a weekly and/or monthly basis). Dynamic reporting is performed for critical events (i.e., when a critical physical characteristic and/or behaviour is detected), such as those described hereinbefore.

The reporting process of the detection server 120 can also be configured to include attendance monitoring, which reports on the detection of the ingress and egress of each student in a class, for example based on facial recognition or other authentication techniques (as described hereinbefore). The detected ingress and egress information may be used by the LMC to register the students' attendance. The LMC stores data representing each student's basic identification information, as received from the BPMS server 130. Attendance event data is generated to represent the ingress and egress of each student in the monitoring area. The attendance data is transferred to the attendance module 134 of the BPMS server 130 during the reporting process, either as a scheduled and/or a dynamic (i.e., real-time) report.

The attendance module 134 can be configured to process the attendance event data to generate logging event data (as described hereinbefore), or other corresponding data, to record the attendance of the student in the monitoring area. In some embodiments, the detection server 120 can be configured to execute the reporting process of step 812 without the identification of any abnormality, such as for example to perform attendance detection for students within the monitoring area.

As described hereinbefore, the physical and/or behavioural detection data generated by the detection server 120 can be utilised to selectively update the corresponding physical and/or behavioural profiles for one or more individuals (i.e., at step 814). In the described embodiments, the detection data is not used to update the biometric profile data if the detection data indicates an abnormality for the individual (as determined in step 810 hereinbefore). For example, if a student's heart rate was sufficiently abnormal to trigger an alert, the reading would not be used to update the profile.

In other embodiments, the ADS 102 can be configured to perform an update of the biometric profile in cases where the detection data was found to indicate an abnormality. In such cases, the relative influence of the detection data values on the biometric profile parameters may be adjusted when performing the update (such as, for example, by attributing a reduced weight to those values).

The detection server 120 is configured to transmit biometric update data to the BPMS server 130 representing the updated physical and/or behavioural profiles of one or more students, as generated by the detection server 120. The biometric update data is processed by the profile management component 132 to generate corresponding biometric data representing the updated profiles, and to store the generated biometric data in the profile database 131.

[Application 2: Cruise Ships]

Passengers and crews of ships are prone to infection, as they spend much of their time in a close environment with other passengers and crews. In addition, passengers that have health issues may board undetected, for example by providing false information regarding their health condition, thereby exposing other passengers and crews to potential infection.

The system and method provided in this disclosure may be used to monitor health indicators of passengers and crews of ships, for example, by monitoring their biometric characteristics such as body temperature and/or heart rate.

For example, monitoring devices may be installed at embarkation points, to monitor the body temperature and heart rate of each boarding person. As the system can compare the person's body temperature and heart rate with the average level of a group of passengers or crew, it may effectively reduce false alarms, especially in the circumstance that the passenger's body temperature has been affected by the terminal's condition, e.g., the departure hall is hot, or a group of passengers has just alighted from a stifling bus. If the person with the elevated reading is representative of the general cohort, then that person will not be signalled by the system as being at risk. If the body temperature of a passenger is significantly higher than the average of other passengers, the system may trigger an alert or send a notification to a doctor on the ship for investigation.

The system may provide additional functions, including one or more of the following:
a) identification upon embarkation and disembarkation at the port;
b) providing access to their cabin and to restricted areas on the ship; and
c) authorising the passenger's on-board purchases and/or managing their account for on-board purchases.

This may allow the system to replace existing boarding cards (such as the SeaPass card) that have been used on cruise ships.

Embarkation

During the embarkation/disembarkation process, the system identifies the passenger, e.g., by using facial recognition or biometric identification techniques, and may retrieve relevant information of that passenger.

For example, at embarkation points, the passenger's name and photo may be retrieved and displayed on a screen at the check-in point, to allow the check-in staff to welcome the passenger by their name. If the passenger cannot be identified from the database, the facial photo acquired by the monitoring device may be displayed on the screen for the check-in staff to confirm and verify the identity of the passenger, and subsequently link their face to their personal information pre-recorded in the database if their identity is verified. Other indicators such as lights may be used. For example, during embarking or disembarking, a green light may indicate to the crew member that the passenger's identification has been confirmed and their embarkation/disembarkation has been recorded, while red light may indicate a problem. An alarm may be triggered if a person is not identified, enabling them to be apprehended.

In this way, the embarkation/disembarkation process may be expedited, as the passengers do not need to locate and present their boarding cards or identity documents when carrying their luggage at the same time. Further, fewer crew are required at the embarkation points, as the device can automatically identify each passenger. The security of the ship may also be improved.

At the same time of registering the embarkation/disembarkation, the system monitors the biomedical characteristics of the passenger, such as body temperature and heart rate, and determines whether the passenger's health condition is suitable for the travel. Any abnormal readings from the initial scan may appear as an alert on the screen, prompting the check-in staff to have the passenger removed to a separate area for more detailed examination by a doctor on the ship.

The facial recognition and the temperature checking may be instantaneous, while the heart rate check may last for a predetermined period of time, e.g., 15 seconds.

Using the identity information and the biometric information collected from the check-in point, the system may start building up a biometric profile for each passenger.

Further monitoring devices may be installed in different areas on the ship, so as to provide additional monitoring of the passenger's health conditions, based on each passenger's biometric profile.

The passenger's biometric profile may be stored in the database and may be reused in the passenger's future cruise travel.

The system may also be used for monitoring and tracking the health condition of ship crews, whose biometric profiles may be recorded and used in different ship trips.

Authorising Access

With additional monitoring devices installed on the ship, for example at entrances to each stateroom door and to restricted areas, the system may be used for providing a passenger access to their cabin and providing selected passengers or ship crew access to restricted areas on the ship, such as a VIP area, a business-class area, or a "ship within a ship" area on large ships for passengers in premium accommodations. This access control may use facial recognition or other biometric identification techniques.

The system may further be configured to unlock or open a door when it is detected that an authorised passenger is approaching it. On the other hand, when a passenger or crewmember enters an unauthorised area, an alert may be triggered.

By this arrangement, passengers no longer need to carry their boarding cards or other identification documents while they are on cruise ships. This will not only reduce the cost for manufacturing the boarding cards, but also avoid the inconvenience brought by a boarding card being lost or forgotten. Furthermore, by providing accurate and automatic control of access to different areas of the ship, the security of the ship may be improved.

Authorising On-Board Purchases

The system may further be used for authorising the passenger's on-board purchases and/or managing their account for on-board purchases.

A shipboard account may be set up for each passenger during the initial shoreside check-in process. The account may be associated with the passenger's facial features, which may be stored in the database of the system, or may have been acquired or updated during the embarkation process by the monitoring device. The facial features of a minor (e.g., a child of a passenger) may be associated with the parent's account, if the parent permits it.

When processing an on-board purchase, the steward is provided with a hand-held device that can take a photo of the passenger's face. The facial photo is sent from the device to the system to identify the passenger's shipboard account associated with that face. The shipboard account is charged accordingly to make the payment for the purchase. The passenger's further personal information may be sent to the hand-held device, such as the passenger's name, to allow the steward to address the passenger by their name.

Further, if the passenger is not authorised to make the purchase, a notification may be sent by the system to the hand-held device that the purchase cannot proceed. For example, if a passenger is under the minimum legal drinking age, the system may reject the purchase request from that passenger.

When a passenger places an order for purchasing a good or a service with the steward, the order may be recorded by the hand-held device and sent automatically to a relevant supply staff, such as a bartender if the passenger is ordering a drink. This may reduce the turnaround time, as the supply staff may start the preparation of the good or service immediately. The actual charge to the passenger's account may be triggered when the good is supplied to the passenger, with a receipt printed for the passenger.

Alternatively, instead of a hand-held device, the passenger's photo may be acquired by a device installed at a counter or a bar where the order can be placed.

Further, the system may detect biometric characteristics of the passenger, and determine whether to authorise the purchase.

For example, the system may monitor the passenger's physical or behavioural characteristic, to detect whether the passenger is intoxicated. If the passenger is detected to be intoxicated, the system may not authorise the purchase, or a notification may be sent to the steward or bartender to reject or terminate the order. In another example, if the passenger is detected to be intoxicated, a crew member may be notified to ensure the safety of the passenger.

In some further examples, the behavioural characteristics of crew members may be monitored to ensure that they provide proper service to the passengers.

In this way, passengers do not have to bring their cash, payment card, boarding card, or other identification document when making the purchase on the ship, and the on-board purchase experience may be enhanced. It may also prevent or reduce the likelihood of a passenger's identity being misappropriated.

[Application 3: Hospitals and Clinics]

The provided method and system may be used for monitoring staff in hospitals, medical centres and clinics.

Front-line staff in these facilities are more prone than the general population to catch infections or infectious disease, and are at higher risk of passing on infections or infectious disease to patients.

Monitoring devices may be installed at multiple locations in these premises to monitor the biometric characteristics of each medical staff, and a server that receives data from the monitors may instantly check the data obtained against the profile of a person associated with it. Variations outside an acceptable range for that person may trigger an alert, allowing the person identified as ill to be pulled from duty immediately.

[Application 4: Factories]

The provided method and system may be used to monitor machine operators in factories, detecting potential health issues or fatigue in them.

Machinery workers need to be alert at all times, both for the safety of themselves and their co-workers, and to ensure that there are no disruptions to the production process.

Existing monitoring devices may monitor a machine operator for signs of weariness. However, in some circumstances, it is normal for a worker to gradually tire over the day within an acceptable extent, without adding significant risk to the operation.

The system provided in the present disclosure can reference the machine operator's detected behaviour to their usual pattern of behaviour at various times of the day, so that an alarm will sound only if the behaviour is abnormal for that person.

A device focusing on each operator or a group of operators may be provided to monitor their biomedical and behaviour characteristics. The system server collects and analyses this data in real time, comparing it with the individual's own biometric profile or biometric pattern associated with that time. For example, it may be normal for an employee to become slightly tired towards the end of their shift, and the system may only trigger an alert if this tiredness becomes excessive.

As the system can build up a profile for each individual, it may self-tune to accept that certain behaviours are normal for that individual. For example, some workers may exhibit signs of stress or fatigue because of excessive fidgeting, while for some other workers these behaviours may be normal. Accordingly, the system may learn that some behaviours are normal for a particular person and avoid sending alert signals in these situations, but only triggers the alarm when a genuine abnormality is detected.

The same or similar system may be provided for production line workers as well. Further, in production lines, a large number of workers are usually working in close proximity to each other, and are therefore more likely to pass infectious diseases to other workers. Accordingly, the system may be configured to also monitor the physical characteristics of the workers, and to alert for any potential health issues that are detected.

In some embodiments, the system may be used to monitor machine operators or production line workers to check whether they are performing the work properly, e.g., to detect whether any worker is not working or not following a predetermined working process.

[Application 5: Aeroplane Pilots]

The provided method and system may be used to monitor pilots for unusual physical or behavioural variations.

The system may be configured to take into account predetermined factors related to physical or behavioural variations. For example, it would be normal for the heart rate of a pilot to increase while the plane is taking off or landing. However, if the heart rate rises mid-flight, the system may recognise it as an abnormality and therefore trigger an alert. The system may also be configured to determine whether a pilot is suitable to fly before the plane leaves the terminal, based on the pilot's physical condition or behaviour.

[Application 6: Drivers]

The provided method and system may be used to monitor a driver's behaviour, and to further detect whether a driver is fatigued based on his or her behaviour. This may apply to car, truck, bus, train or tram drivers.

Compared to some existing driver monitoring systems, the system and method provided in the present disclosure are configured to take into account an individual's specific behaviour patterns. For example, some drivers tend to make more movement during driving than other drivers. Using the system provided herein, frequent movement of this driver can be recognised as his or her normal behaviour, thereby effectively reducing false alarms. At the same time, out-of-character behaviour of the driver can be accurately detected to alert for situations such as fatigue driving or drunk driving. The system may further inhibit the vehicle to be started if the driver is detected to be fatigued or drunk.

The system may further include the function of facial recognition, so that a separate profile can be created for each driver, to cater for the situation that a same vehicle may be driven by different drivers at different times. The system may further provide driver authorisation based on the result of facial recognition, so that the vehicle will not start if the driver is an unauthorised person, with the exception of allowing parking attendants, service personnel and the like to drive the vehicle if so authorised.

[Application 7: Childcare Centres]

The provided method and system may be used in childcare centres to monitor health conditions and behaviours of children, for example, their body temperatures. This may facilitate preventing or mitigating the spread of infectious diseases in these facilities.

For example, the system may be used to monitor the children entering a shared space, such as the playroom and may alert the staff of the childcare centre that a child is sick before he or she enters the playroom.

The system may also monitor all the children in the childcare centre during the day, and detect signs of medical issues before they become apparent or for behavioural anomalies that the staff may not have noticed.

As the system provides personalised standards for judging what is abnormal, the accuracy and reliability of the detection may be enhanced compared to conventional devices or systems.

In addition, the system may also be used to monitor the health and/or behaviour of staff, e.g., whether they have a health issue, or whether they are treating the children appropriately.

[Application 8: Nursing Homes]

The provided method and system may be used for nursing homes or other aged care facilities. Similar functions to those for childcare centres may be provided.

[Application 9: Baby Monitoring]

The provided method and system may be used to provide continuous and remote monitoring of one or more of the following biometric characteristics of a baby:
  a) body temperature;
  b) sleep patterns;
  c) movements/gestures;
  d) heart rate; and
  e) breathing patterns.

When an abnormality is detected, e.g., the baby's movements, heart rate or temperature go beyond a range that is normal for the baby, an alarm may be triggered to notify the parents or care giver.

[Application 10: Terror Alerts]

The provided method may be used for detecting an abnormal event such as a terrorist attack. For example, the system may be configured to trigger an alert if it detects someone is conducting an abnormal behaviour, such as holding a gun or a knife. A group of people (students in a classroom) moving erratically may also signify a terrorist situation.

[Application 11: Intelligent Security Systems]

The provided method can be used in an Intelligent Security Systems (ISS). The system may automatically detect abnormal behaviour. It may also be used for tracing a particular individual. For example, if stock has been stolen by an employee in a business or store, the stored identity data or biometric data of a particular person may be used to automatically find in the recorded video all footage that includes the person, rather than manually looking through the whole video recording.

The system may also check a person's identity and monitor whether that person is authorised to conduct a pre-determined behaviour or enters a restricted area. If the person conducts an unauthorised behaviour, the system may trigger an alert. For example, if it is detected that a cleaner has opened a cash drawer in a shop, or a customer has entered a staff-only area in a restaurant, an alarm may be triggered.

[Interpretation]

The reference in this specification to any prior publication (or information derived from it), or to any matter which is known, is not, and should not be taken as an acknowledgement or admission or any form of suggestion that that prior publication (or information derived from it) or known matter forms part of the common general knowledge in the field of endeavour to which this specification relates.

Many modifications will be apparent to those skilled in the art without departing from the scope of the present invention as hereinbefore described with reference to the accompanying drawings.

The invention claimed is:

1. An abnormality determination system for determining an abnormality of an individual within a learning environment, including:
   a monitor, including one or more imaging devices, said imaging devices configured to generate imaging signals; and
   at least one abnormality detection server device, including:
   a communications interface to receive data;
   at least one computer processor to execute program instructions; and
   a memory, coupled to the at least one computer processor, storing program instructions for execution by the at least one computer processor to automatically:
   receive imaging signals from the monitor;
   process the imaging signals to generate imaging data;
   process the imaging data to detect the individual, and to generate corresponding identity data representing the identity of the individual; and
   identify an abnormality of the individual based on:
      physical detection data representing the detection of a physical characteristic of the individual from the imaging data, and a corresponding physical profile of the individual; or
      behavioural detection data representing the detection of a behavioural characteristic of the individual from the imaging data, and a corresponding behavioural profile of the individual; and
      context data representing a context of the detected behavioural or physical characteristic within the learning environment, wherein the context includes one or more influencing factors that influence the physical characteristic or behavioural characteristic of the individual;
   wherein identifying the abnormality of the individual includes:
      adjusting the corresponding physical profile or behavioural profile of the individual based on the context data.

2. The abnormality determination system of claim 1, wherein the imaging signals include: video signals and thermal imaging signals, the thermal imaging signals including a series of thermal images that are associated with corresponding images of the video signals, and
   where the video signals and thermal imaging signals are generated by a first imaging device and a second imaging device respectively, said video signals and thermal imaging signals being processed by the abnormality detection server device to generate one or more video and thermal image frames including the individual.

3. The abnormality determination system of claim 1, wherein the identifying of an abnormality of the individual based on behavioural detection data includes:
   processing the behavioural detection data to determine that the behavioural characteristic is one of a behaviour type including: a gesture; and a facial expression;
   comparing the behavioural detection data to one or more behavioural characteristic models of the determined behaviour type; and
   selecting a particular behavioural characteristic based on a result of the comparison,
   where the behavioural characteristics are specific to the learning environment and include:
   for the gesture behaviour type: (i) Head-scratching; (ii) Hitting/striking; (iii) Nodding; (iv) Hand-raising; (v) Waving; and (vi) Thumbs up/down; and
   for the facial expression behaviour type: (i) Smiling; (ii) Frowning; and (iii) Crying.

4. The abnormality determination system of claim 3, wherein the behavioural characteristics include: for the gesture behaviour type: (vii) one or more user-defined gestures, said user-defined gestures being gestures that are customised and/or configured specifically for the abnormality determination system.

5. The abnormality determination system of claim 1, wherein the abnormality detection server device is configured to selectively update the physical profile of the individual based on corresponding physical detection data or the behavioural profile of the individual based on corresponding behavioural detection data.

6. The abnormality determination system of claim 1, wherein the abnormality detection server device is configured to:
   transmit, to a management system device of the learning environment, an indication of the identity of the individual;
   transmit, to the management system device, an indication of an abnormality identified for the individual; and
   receive, from the management system device, context data representing a context for detected behavioural or physical characteristics of the individual.

7. The abnormality determination system of claim 1, wherein the context data indicates one or more of:
   the types of learning activities being undertaken by the individual; and
   the highest degree of physical activity in which the individual has engaged n within a particular time period.

8. The abnormality determination system of claim 1, wherein the identification of an abnormality of the individual includes comparing the physical detection data to a physical model of the corresponding physical profile of the individual, said physical model being determined based on the context of the detected physical characteristics within the learning environment.

9. The abnormality determination system of claim 8, wherein the physical profile of the individual includes at least one of:
   a heart rate profile; and
   a temperature profile,
   and wherein said heart rate and temperature profiles each having one or more physical models representing the respective nominal heart rate and temperature levels of the individual for a particular context.

10. The abnormality determination system of claim 9, wherein the heart rate profile of the individual includes physical models each representing: i) a "resting state", which represents the heart rate of the individual when they have not undertaken vigorous physical activity; and ii) a "high activity" state which represents the heart rate of the individual when they have engaged in physical activity within the particular time period.

11. The abnormality determination system of claim 8, wherein the abnormality detection server device is configured to:
    transmit, to a management system device of the learning environment, an indication of the identity of the individual;
    transmit, to the management system device, an indication of an abnormality identified for the individual; and
    receive, from the management system device, context data representing a context for detected behavioural or physical characteristics of the individual.

12. The abnormality determination system of claim 8, wherein the imaging signals include: video signals and thermal imaging signals, the thermal imaging signals including a series of thermal images that are associated with corresponding images of the video signals, and
    where the video signals and thermal imaging signals are generated by a first imaging device and a second imaging device respectively, said video signals and thermal imaging signals being processed by the abnormality detection server device to generate one or more video and thermal image frames including the individual.

13. The abnormality determination system of claim 1, wherein the identification of an abnormality of the individual includes comparing the behavioural detection data to a behavioural model of the corresponding behavioural profile of the individual, said behavioural model being determined based on the context of the detected behavioural characteristics within the learning environment.

14. The abnormality determination system of claim 13, wherein the behavioural model of the individual includes, at least, behavioural tendency data representing the tendency of the individual to exhibit one or more of the detected behavioural characteristics relative to the context.

15. The abnormality determination system of claim 14, wherein the behavioural tendency data for a particular behavioural characteristic includes an indication of the frequency with which the individual nominally exhibits the particular behavioural characteristic within a time period.

16. The abnormality determination system of claim 13, wherein the abnormality detection server device is configured to:
    transmit, to a management system device of the learning environment, an indication of the identity of the individual;
    transmit, to the management system device, an indication of an abnormality identified for the individual; and
    receive, from the management system device, the context data representing a context for detected behavioural or physical characteristics of the individual.

17. The abnormality determination system of claim 13, wherein the imaging signals include: video signals and thermal imaging signals, the thermal imaging signals including a series of thermal images that are associated with corresponding images of the video signals, and
    where the video signals and thermal imaging signals are generated by a first imaging device and a second imaging device respectively, said video signals and thermal imaging signals being processed by the abnormality detection server device to generate one or more video and thermal image frames including the individual.

18. An abnormality determination method for determining an abnormality of an individual within a learning environment, including:
    receiving imaging signals from a monitor including one or more imaging devices, said imaging devices configured to generate the imaging signals;
    processing the imaging signals to generate imaging data;
    processing the imaging data to detect the individual, and to generate corresponding identity data representing the identity of the individual; and
    identifying an abnormality of the individual based on:
        physical detection data representing the detection of a physical characteristic of the individual from the imaging data, and a corresponding physical profile of the individual and context data representing a context of the detected physical characteristics within the learning environment; or
        behavioural detection data representing the detection of a behavioural characteristic of the individual from the imaging data, and a corresponding behavioural profile of the individual and context data representing a context of the detected behavioural characteristics within the learning environment; and
        context data representing a context of the detected behaviour or physical characteristic within the learning environment, wherein the context includes one or more influencing factors that influence the physical characteristic or behavioural characteristic of the individual;
    wherein identifying the abnormality of the individual includes:
        adjusting the corresponding physical profile or behavioural profile of the individual based on the context data.

* * * * *